US009950059B2

(12) United States Patent
Yu et al.

(10) Patent No.: US 9,950,059 B2
(45) Date of Patent: Apr. 24, 2018

(54) IMMUNOGENIC COMPOSITION

(71) Applicant: THE UNITED STATES OF AMERICA, AS REPRESENTED BY THE SECRETARY OF AGRICULTURE, Washington, DC (US)

(72) Inventors: Qingzhong Yu, Athens, GA (US); Stephen J. Spatz, Athens, GA (US); Laszlo Zsak, Athens, GA (US)

(73) Assignee: The United States of America, as represented by the Secretary of Agriculture., Washington, DC (US)

( * ) Notice: Subject to any disclaimer, the term of this patent is extended or adjusted under 35 U.S.C. 154(b) by 0 days.

(21) Appl. No.: 15/120,237

(22) PCT Filed: Feb. 13, 2015

(86) PCT No.: PCT/US2015/015848
§ 371 (c)(1),
(2) Date: Aug. 19, 2016

(87) PCT Pub. No.: WO2015/130492
PCT Pub. Date: Sep. 3, 2015

(65) Prior Publication Data

US 2017/0072046 A1 Mar. 16, 2017

Related U.S. Application Data

(60) Provisional application No. 61/944,143, filed on Feb. 25, 2014.

(51) Int. Cl.

| | |
|---|---|
| ***A61K 39/17*** | (2006.01) |
| ***A61K 39/245*** | (2006.01) |
| ***C12N 7/00*** | (2006.01) |
| ***C12N 15/86*** | (2006.01) |
| ***A61K 39/12*** | (2006.01) |
| ***A61K 39/00*** | (2006.01) |

(52) U.S. Cl.
CPC .............. *A61K 39/17* (2013.01); *A61K 39/12* (2013.01); *A61K 39/245* (2013.01); *C12N 7/00* (2013.01); *C12N 15/86* (2013.01); *A61K 2039/525* (2013.01); *A61K 2039/552* (2013.01); *C12N 2710/16034* (2013.01); *C12N 2760/18034* (2013.01); *C12N 2760/18043* (2013.01); *C12N 2760/18121* (2013.01); *C12N 2760/18134* (2013.01); *C12N 2760/18143* (2013.01)

(58) Field of Classification Search
CPC .............. A61K 39/12; A61K 2039/552; A61K 2039/5256; A61K 2300/00; A61K 2039/70; A61K 39/17; A61K 2039/5254; A61K 2039/6075; A61K 2039/5258; A61K 39/245; A61K 39/295; A61K 2039/53; A61K 39/155; A61K 2039/525; A61K 35/76; A61K 38/162; A61K 39/255; C12N 7/00; C12N 15/86; C12N 2760/18134; C12N 2710/16343; C12N 2710/16334; C12N 2760/18143; C12N 2760/18334; C12N 2760/18534; C12N 2710/16034; C12N 2710/16043; C12N 2710/16321; C12N 2760/18034; C12N 2760/18171; C12N 15/869; C12N 2760/18121; C12N 2710/16311; C12N 2760/18111; C12N 2310/11
See application file for complete search history.

(56) References Cited

U.S. PATENT DOCUMENTS

| | | | |
|---|---|---|---|
| 6,146,642 A | 11/2000 | Garcia-Sastre | |
| 7,029,681 B2 | 4/2006 | Kuo | |
| 2017/0049880 A1* | 2/2017 | Samal | .................. A61K 39/245 |

FOREIGN PATENT DOCUMENTS

| | | | |
|---|---|---|---|
| WO | 0015853 A1 | | 3/2000 |
| WO | WO2000061736 A3 | * | 4/2000 |
| WO | 2012030720 A1 | | 3/2012 |
| WO | 2013-057236 A1 | | 4/2013 |

OTHER PUBLICATIONS

Spatz SJ, Volkening JD, Keeler CL, Kutish GF, Riblet SM, Boettger CM, Clark KF, Zsak L, Afonso CL, Mundt ES, Rock DL, Garcia M. Comparative full genome analysis of four infectious laryngotracheitis virus (Gallid herpesvirus-1) virulent isolates from the United States. Virus Genes. Apr. 2012;44(2):273-85. Epub Dec. 16, 2011.*
Spatz S. US6 protein [Gallid alphaherpesvirus 1]. GenBank: AFD36775.1. Dep. Apr. 23, 2012.*
Spatz S. Gallid herpesvirus 1 strain 63140/C/08/BR, complete genome. GenBank: JN542536.1. Dep. Apr. 23, 2012.*
Lu Y, ZhaoH, He CQ. Newcastle disease virus strain LaSota, complete genome. GenBank: JF950510.1. Aug. 10, 2011.*
Oldoni I, Garcia M. Envelope glycoprotein B [Gallid alphaherpesvirus 1]. GenBank: ABX59522.1. Dec. 31, 2007.*
(Continued)

*Primary Examiner* — Rachel B Gill

(74) *Attorney, Agent, or Firm* — John D. Fado; David L. Marks

(57) ABSTRACT

Recombinant chimeric viruses based on NDV LaSota strain and containing either ILTV gB or gD are produced. Administration of the chimeric viruses to chickens induces an immune response in the animal against both NDV and ILTV. Immunogenic compositions, plasmids, kits and methods are described.

13 Claims, 6 Drawing Sheets

(56) References Cited

OTHER PUBLICATIONS

Gao Q, Park Ms, Palese P. Expression of transgenes from newcastle disease virus with a segmented genome. J Virol. Mar. 2008; 82(6):2692-8. Epub Jan. 16, 2008.*
Khattar, Sunil K. et al., "Immunization of cattle with recombinant Newcastle disease virus expressing bovine herpesvirus-1 (BHV-1) glycoprotein D induces muscosal and serum antibody responses and provides partial protection againt BHV-1", Vaccine, vol. 28, Issue 18, pp. 3159-3170, 2010.
NCBI, GenBank Accession No. JF795531.1, Apr. 25, 2013.
Brun, Alejandro et al., "Antigen delivery systems for veterinary vaccine development: viral-vector based delivery systems", Vaccine, vol. 26, Issue 51, pp. 6508-6528, 2008.
NCBI, GenBank accession No. EU104975.1, Dec. 31, 2007.
NCBI, GenBank accession No. ABX59522.1, Dec. 31, 2007.
NCBI, GenBank accession No. JN542536.1, Apr. 23, 2012.
NCBI, GenBank accession No. AAC55100.1, Aug. 9, 1996.
Zhao, Wei et al., "Newcastle disease virus (NDV) recombinants expressing infectious laryngotracheitis virus (ILTV) glycoproteins gB and gD protect chickens against ILTV and NDV challenges", Journal of Virology, vol. 88, No. 15, pp. 3397-8406, Epub. May 14, 2014.
Basavarajappa, Mallikarjuna Kanabagatte et al., "A recombinant Newcastle disease virus (NDV) expressing infetious laryngotracheitis virus (ILTV) surface glycoprotein D protects against highly viruletn ILTV and NDV challenges in chickens", Vaccine, vol. 32, Issue 28, pp. 3555-3563, Epub. Apr. 30, 2014.
Bukreyev, Aalexander, et al. "Recombinant Newcastle Disease Virus Expressing a Foreign Viral Antigen Is Attenuated and Highly Immunogenic in Primates", (2005) Journal of Virology, 79(21), 13275-13284.
NCBI, GenBank: JF795531.1 "Newcastle disease virus strain HX01, complete genome", Apr. 25, 2013, 36 pgs.
Brun, Alejandro, et al. "Antigen delivery systems for veterinary vaccine development Viral-vector based delivery systems", (2008), Vaccine 26, 6508-6528.
NCBI, GenBank: EU104975.1 "Gallid herpesvirus 1 isolate 205/J/06/BR envelope glycoprotein B gene, complete cds", Dec. 31, 2007, 15 pgs.
NCBI, GenBank: ABX59522.1 "envelope glycoprotein B [Gallid herpesvirus 1]", Dec. 31, 2007, 9 pgs.
NCBI, GenBank: JN542536.1 "Gallid herpesvirus 1 strain 63140/C/08/BR, complete genome", Apr. 23, 2012, 54 pgs.
NCBI, GenBank: AAC55100 "glycoprotein D [Gallid herpesvirus 1]", Aug. 9, 1996, 8 pgs.
Zhao, Wei, et al. "Newcastle Disease Virus (NDV) Recombinants Expressing Infectiuous Laryngotracheitis Virus (ILTV) Glycoproteins gB and gD Protect Chickens against ILTV and NDV Challenges", (2014), Journal of Virology, 88 (15), 8397-8406.
Dinapoli, Joshua M., "Newcastle disease virus, a host range-restricted virus, as a vaccine vector for intranasal mmunization against emerging pathogens", (2007), The National Academy of Sciences of the USA, 104(23), 9788-9793.
Dinapoli, Joshua M. et al., "Delivery to the lower respiratory tract is required for effective immunization with Newcastle disease virus-vectored vaccines intended for humans", (2009), Vaccine, 27(10), 1530-1539.
Ge, Jinying, et al., "Newcastle Diseae Virus-Based Live Attenuated Vaccine Completely protects Chickens and Mice from Lethal Challenge of Homologous and Heterologous H5N1 Avian Influenza Viruses", (2007), Journal of Virology, 81(1), 150-158.
Ge, Jinying, et al. "Generation and Evaluation of a Newcastle Disease Virus-Based H9 Avian Influenza Live Vaccine", (2010), Avian Diseases, 54, 294-296.
Hu, Haixia, et al. "Genration and evaluation of a recombinant Newcastle disease virus expressing the glycoprotein (G) of avian metapneumovirus subgroup C as a bivalent vaccine in turkeys", (2011), Vaccine, 29, 8624-8633.
Basavarajappa, Mallikarjuna Kanabagatte, et al. "A recombinant Newcastle disease virus (NDV) expressing nfectious laryngotracheitis virus (ILTV) surface glycoprotein D protects against highly virulent ILTV and NDV challenges in chickens", (2014), Vaccine, 32, 3555-3563.
Nakaya, Takaaki, et al. "Recombiant Newcastle Disease Virus as a Vaccine Vector", (2001), Journal of Virology, 75(23), 11868-11873.
Nayak, Baibaswata, et al., "Immunization of Chickens with newcastle Disease Virus Expressing H5 Hemagglutinin Protects against Highly Pathogenic H5N1 Avian Influenza Viruses", (2009), PLos One, 4(8), 1-10.
Park, Man-Seong, et al. "Engineered virial vaccine constructs with dual specificity: Avian influenza and Newcastle lisease", (2006), PNAS, 103(21), 8203-8208.
Spatz, S.J., et al. "Comparative full genome analysis of four infectious laryngotracheitis virus (Gallid herpesvirus-1) virulent isolates from the United States", (2012), Virus Genes, 44, 273-285.
Swayne, D.E., et al. "Rcombinant Paramyxovirus Type 1-Avian Influenza-H-7 Virus as a Vaccine for Protection of chickens Against Influenza and Newcastle Disease", (2003), Avian Diseases, 47, 1047-1050.
Zhao, Wei, et al. "Newcastle Disease Virus (NDV) Recombinants Expressing Infectious Laryngotracheitis Virus (ILTV) Glycoproteins gB and gD Protect Chickens against ILTV and NDV Challenges", (2014), Journal of Virology, 88(15), 8397-8406.
Zhao, Wei, et al."Application of the ligation-independent cloning (LIC) method for rapid construction of a minigenome rescue system for Newcastle disease virus VG/GA strain", (2013), Plasmid, 70, 314-320.

* cited by examiner

Total clinical sign scores after ILTV challenge at 21 DPV

— PBS
— rLS-GFP
— rLS/ILTV-gB
— rLS/ILTV-gD

Total clinical sign scores after chllenge at 28 DPV

— rLS-GFP
— rLS/ILTV-gB
— rLS/ILTV-gD

| | eyes 21 pv | eyes 28 pv | trachea 21 pv | trachea 28 pv |
|---|---|---|---|---|
| gB | 6.60 | 37.54 | 12.52 | 8.85 |
| gD | 16.82 | 22.75 | 3.75 | 2.72 |

| | D2 | D3 | D4 | D5 | D6 | D7 | D8 | D9 |
|---|---|---|---|---|---|---|---|---|
| PBS | 0 | 16 | 69 | 123 | 90 | 59 | 33 | 15 |
| rLS-GFP | 0 | 11 | 50 | 101 | 60 | 22 | 13 | 12 |
| rLS/ILTV-gB | 0 | 1 | 1 | 1 | 1 | 1 | 0 | 0 |
| CEO | 0 | 2 | 1 | 1 | 1 | 1 | 1 | 0 |
| TCO | 0 | 0 | 0 | 0 | 0 | 0 | 0 | 0 |

| | rLS/ILTV-gB | CEO | TCO |
|---|---|---|---|
| Trachea | 16.84 | 155.61 | 520.47 |

| | | | | | | |
|---|---|---|---|---|---|---|
| t-Test | *P*<0.05 | *P*<0.05 | *P*>0.05 | *P*>0.05 | *P*>0.05 | |

IMMUNOGENIC COMPOSITION

This is a National Phase Application filed under 35 U.S.C. 371 as a national stage of PCT/US2015/015848, filed Feb. 13, 2015, an application claiming the benefit of U.S. Provisional Application No. 61/944,143, filed Feb. 25, 2014, the content of each of which is hereby incorporated by reference in its entirety.

BACKGROUND OF THE INVENTION

Field of Invention

This invention relates to a novel chimeric virus and immunogenic compositions containing the chimeric virus which, when administered to an animal, can induced an immune response to both NDV and ILTV. This invention relates more specifically to NDV LaSota strain expressing ILTV gB or gD antigens, immunogenic compositions containing one or both chimeric viruses, and methods of use thereof.

The Sequence Listing submitted in text format (.txt) filed on Feb. 13, 2015, named "Sequence_Listing.txt", (created on Feb. 25, 2014, 161 KB), is incorporated herein by reference.

Description of the Prior Art

Infectious laryngotracheitis (ILT), classified as a disease requiring notification to the World Organization for Animal Health (OIE), is a highly contagious acute respiratory disease that has become a major problem in the U.S. poultry industry in recent years and is caused by infectious laryngotracheitis virus (ILTV), formally called Gallid herpesvirus type 1 (GaHV-1). For protection, chickens are vaccinated multiple times with live strains that were attenuated by either multiple passages in embryonated eggs (chicken embryo origin [CEO] or in tissue culture (tissue culture origin) [TCO]). Although these vaccines protect against clinical disease, they have residual virulence which is exacerbated by continued infections of naive birds from productively infected animals and latent carriers. Moreover, the CEO vaccine strain has been demonstrated to mutate and become more virulence simply by bird-to-bird passage. Because of this characteristic, it is believed that U.S. vaccine strains have mutated to become more virulent and these "revertants" have become the dominant field strains in the poultry population. As a result of this increased virulence in the circulating virus and the use of high-density poultry housing, there is a continuous reservoir of viruses (both virulent and vaccinal) in flocks that is capable of evolving to higher levels of virulence.

To overcome problems associated with live attenuated ILTV vaccine strains, inactivate whole-virus vaccines and turkey herpesvirus (HVT)- and fowl poxvirus (FPV)-vectored constructs containing ILTV antigens have been developed and tested in protection studies. Although these vaccines are completely safe when administered at different ages, they induce only partial protection when compared with that induced by a live-attenuated ILTV vaccine. As such, a significant need exists for a new ILT vaccine strategy, particularly regarding the development of next generation vaccines or immunogenic compositions that are inexpensive, incapable of virulent reversion, and unable to transfer horizontally to naïve birds, in order to control the disease and prevent devastating losses.

ILTV, an alphaherpesvirus, possesses at least ten envelope glycoprotein genes, including glycoprotein B (gB) and glycoprotein D (gD) which are the most highly conserved herpesvirus structural glycoproteins. Glycoprotein B is essential for infectivity and is involved in membrane fusion and virus penetration. Glycoprotein D is essential for most herpesviruses and functions as a receptor for virus binding to susceptible cells. In addition, gB elicits high titers of neutralizing antibodies and cell-mediated immune responses, and has been shown to be a strong candidate antigen for recombinant subunit vaccines.

Newcastle disease (ND), caused by infection of virulent Newcastle disease virus (NDV), is one of the most serious infectious diseases in poultry. It has been classified into one serotype and three different pathotypes: velogenic (highly virulent), mesogenic (moderately virulent), and lentogenic (low virulence) viruses. Velogenic strains can cause severe disease, characterized by extensive lesions and high mortality in both the laboratory and field, and such outbreaks require reporting to the World Organization for Animal Health (OIE) by member nations.

Vaccination combined with strict biosecurity practices have been recommended for controlling NDV outbreaks for over 60 years. The NDV LaSota strain, a naturally-occurring low virulence NDV strain, has been routinely used as a live vaccine throughout the world for more than fifty years to prevent ND. This vaccine strain induces strong immunity both locally and systemically and can be readily administered through drinking water supplies or by directly spraying the birds. The LaSota vaccine has been proven to be safe and stable, and there are no reports of virulence reversion or recombination for this vaccine strain to generate new virulent strains.

NDV is a negative-sense single-strand RNA virus which contains a negative-sense RNA inside its capsid. After entry into a cell, the virus/cell makes positive-sense RNAs (mRNA and anti-genomic RNA) which are used to generate viral proteins and nascent negative-sense single-strand RNAs which are packaged into virions. The negative-sense ssRNA sequence of NDV is the reverse complement of the cDNA sequence of the viral RNA.

Others have explored using recombinant Newcastle disease virus (rNDV) LaSota strain (rLS) as a vector for presenting heterologous antigens to an animal's immune system. Much of this work involved the use of rNDV vector for combating human diseases, although some involved vaccines for avain pathogenic microorganisms. See, Bukreyev and Collins, *Curr. Opin. Mol. Ther.* 10(1):46-55 (2008) using of rNDV as a vector for respiratory tract disease antigens for humans; Bukreyev, et al., *J. Virology* 79(21):13275-84 (2005) examining use of rNDV expressing human parainfluenza virus type 3 hemagglutinin-neuraminidase protein; DiNapoli, et al., *Proc. Natl. Acad. Sci.,* 104 (23):9788-93 (2007) examining rNDV as vector for severe acute respiratory syndrome-associated coronavirus spike S glycoprotein; DiNapoli, et al., *Vaccine* 27(10):1530-9 (2009) examining efficacy of various routes of administration of rNDV-vectored vaccines; Ge, et al., *J. Virol.* 81:150-158 (2007) examining rNDV expressed an H5 subtype avian influenza virus hemagglutinin; Ge, et al., *Avian Dis.* 54:294-296 (2010) examining rNDV expressed an H9 subtype avian influenza virus hemagglutinin; Huang, et al., *Poultry Science* 82:899-906 (2003) reviews rNDV as vaccine vector for veterinary use; Nakaya, et al., *Virol.* 75:11868-11873 (2001) examining rNDV expressing influenza virus hemagglutinin; Nayak, et al., *PloS One* 4(8) e6509 (2009) examining rNDV expressing H5 influenza hemagglutinin; Park, et al., *Proc. Natl. Acad. Sci.* 103:8203-8208 (2006) examining rNDV expressing ectodomain of an H7 avian influenza virus hemagglutinin; and Swayne, et al., *Avian Dis.* 47:1047-1050 (2003) examining expression of avian influenza virus H7 hemagglutinin in rNDV.

Previously, a chimeric virus of NDV LaSota strain and a heterologous antigen (glycoprotein from three separate strains of avian metapneumovirus (aMPV)) was generated and evaluated as an immunogenic composition to generate a protective immune response against both NDV and aMPV (aMPV-A, aMPV-B, or aMPV-C) (Hu, et al., *Vaccine* 29:8624-8633 (2011) and Yu, et al., *World J. of Vaccines* 3:130-139 (2013)). The DNA sequence of the heterologous antigen was placed between the F gene and HN gene of the NDV LaSota strain. In these three cases, the chimeric virus failed to induce a sufficiently robust immune response in the inoculated animal to protect the inoculated animal against the disease caused by aMPV (turkey rhinotracheitis), even when the animal was exposed to the aMPV strain from which the glycoprotein (heterologous antigen) was obtained. While not wishing to be bound to any hypothesis, the incomplete protection could have resulted from one or more factors including, but not limited to, the use of a weak antigen which was unable to stimulate a sufficiently robust immune response to protect the inoculated animal, low production of the foreign antigen by the cell because of the location the sequences encoding the heterologous antigen were inserted into NDV's genomic RNA, and poor replication of the chimeric virus in the inoculated animal.

To overcome numerous problems associated with live attenuated ILTV strains, a recombinant NDV LaSota strain is used as a live vaccine vector to express ILTV's gB or gD genes (a chimeric virus). This chimeric vaccine is an immunogenic composition that, after administration to an animal, induces an immune response in the recipient to both NDV and ILTV and prevents both diseases. In light of prior failures of a chimeric virus of NDV LaSota strain and a heterologous antigen, it is surprising and unexpected result that the animals inoculated with the chimeric virus of the present invention generate a sufficiently robust immune response to be protected from ILTV and the disease it causes.

BRIEF DESCRIPTION OF THE INVENTION

It is an object of this invention to have a novel, chimeric virus that is a NDV LaSota strain and contains a heterologous antigen from ILTV. It is a further object of this invention that the heterologous antigen be either gB or gD. It is another object of this invention that chimeric viruses of this invention induces an immune response in an animal to both NDV and ILTV after administration of the chimeric virus to the animal. It is a further object of this invention to have immunogenic compositions containing one or both of these chimeric viruses. It is another object of this invention to have a method of generating an immune response to NDV and ILTV in an animal by administering an immunogenic effective amount of this immunogenic composition to an animal. It is yet another object of this invention to have a method of preventing ILTV disease and NDV disease in an animal by administering an immunogenic effective amount of the immunogenic compositions of this invention to an animal in need thereof. It is still a further object of this invention to have a method of reducing shedding of ILTV and NDV by an animal capable of being infected with ILTV and/or NDV by administering an immunogenic effective amount of the immunogenic composition of this invention to the animal.

It is an object of this invention to have a novel, chimeric virus that is a NDV LaSota strain and contains ILTV gB. It is a further object of this invention that the DNA sequence of gB is the sequence in SEQ ID NO: 1, or a sequence that has at least 95%, 96%, 97%, 98% or 99% identity to the sequence in SEQ ID NO: 1. It is another object of this invention that the chimeric virus of this invention induces an immune response in an animal to both NDV and ILTV after administration of the chimeric virus to the animal. It is a further object of this invention to have an immunogenic composition containing this chimeric virus, one or more diluents, optionally an adjuvant, and optionally a carrier. It is another object of this invention to have a method of generating an immune response to NDV and ILTV in an animal by administering an immunogenic effective amount of this immunogenic composition to an animal. It is yet another object of this invention to have a method of preventing ILTV disease and NDV disease in an animal by administering an immunogenic effective amount of the immunogenic composition of this invention to an animal in need thereof. It is still a further object of this invention to have a method of reducing shedding of ILTV and NDV by an animal capable of being infected with ILTV and/or NDV by administering an immunogenic effective amount of the immunogenic composition of this invention to the animal.

It is an object of this invention to have a novel, chimeric virus that is a NDV LaSota strain and contains ILTV gB. It is a further object of this invention that the amino acid sequence of gB is the sequence in SEQ ID NO: 2, or a sequence that has at least 95%, 96%, 97%, 98% or 99% identity to the sequence in SEQ ID NO: 2. It is another object of this invention that the chimeric virus of this invention induces an immune response in an animal to both NDV and ILTV after administration of the chimeric virus to the animal. It is a further object of this invention to have an immunogenic composition containing this chimeric virus, one or more diluents, optionally an adjuvant, and optionally a carrier. It is another object of this invention to have a method of generating an immune response to NDV and ILTV in an animal by administering an immunogenic effective amount of this immunogenic composition to an animal. It is yet another object of this invention to have a method of preventing ILTV disease and NDV disease in an animal by administering an immunogenic effective amount of the immunogenic composition of this invention to an animal in need thereof. It is still a further object of this invention to have a method of reducing shedding of ILTV and NDV by an animal capable of being infected with ILTV and/or NDV by administering an immunogenic effective amount of the immunogenic composition of this invention to the animal.

It is an object of this invention to have a novel, chimeric virus that is a NDV LaSota strain and contains ILTV gB. It is a further object of this invention that the chimeric virus contains a negative-strand RNA having an RNA sequence that is (i) the equivalent of the reverse complement of SEQ ID NO: 14, (ii) a sequence that has at least 95%, 96%, 97%, 98%, or 99% identity to SEQ ID NO: 14, (iii) SEQ ID NO: 15, or (iv) a sequence that has at least 95%, 96%, 97%, 98%, or 99% identity to SEQ ID NO: 15. It is another object of this invention that the chimeric virus of this invention induces an immune response in an animal to both NDV and ILTV after administration of the chimeric virus to the animal. It is a further object of this invention to have an immunogenic composition containing this chimeric virus, one or more diluents, optionally an adjuvant, and optionally a carrier. It is another object of this invention to have a method of generating an immune response to NDV and ILTV in an animal by administering an immunogenic effective amount of this immunogenic composition to an animal. It is yet another object of this invention to have a method of preventing ILTV disease and NDV disease in an animal by administering an immunogenic effective amount of the immunogenic composition of this invention to an animal in need thereof. It is still a further object of this invention to have a method of reducing shedding of ILTV and NDV by an animal capable of being infected with ILTV and/or NDV by administering an immunogenic effective amount of the immunogenic composition of this invention to the animal.

It is an object of this invention to have a novel, chimeric virus that is a NDV LaSota strain and contains ILTV gD. It is a further object of this invention that the DNA sequence of gD is the sequence in SEQ ID NO: 3, or a sequence that has at least 95%, 96%, 97%, 98% or 99% identity to the sequence in SEQ ID NO: 3. It is another object of this invention that the chimeric virus of this invention induces an immune response in an animal to both NDV and ILTV after administration of the chimeric virus to the animal. It is a further object of this invention to have an immunogenic composition containing this chimeric virus, one or more diluents, optionally an adjuvant, and optionally a carrier. It is another object of this invention to have a method of generating an immune response to NDV and ILTV in an animal by administering an immunogenic effective amount of this immunogenic composition to an animal. It is yet another object of this invention to have a method of preventing ILTV disease and NDV disease in an animal by administering an immunogenic effective amount of the immunogenic composition of this invention to an animal in need thereof. It is still a further object of this invention to have a method of reducing shedding of ILTV and NDV by an animal capable of being infected with ILTV and/or NDV by administering an immunogenic effective amount of the immunogenic composition of this invention to the animal.

It is an object of this invention to have a novel, chimeric virus that is a NDV LaSota strain and contains ILTV gD. It is a further object of this invention that the amino acid sequence of gD is the sequence in SEQ ID NO: 4, or a sequence that has at least 95%, 96%, 97%, 98% or 99% identity to the sequence in SEQ ID NO: 4. It is another object of this invention that the chimeric virus of this invention induces an immune response in an animal to both NDV and ILTV after administration of the chimeric virus to the animal. It is a further object of this invention to have an immunogenic composition containing this chimeric virus, one or more diluents, optionally an adjuvant, and optionally a carrier. It is another object of this invention to have a method of generating an immune response to NDV and ILTV in an animal by administering an immunogenic effective amount of this immunogenic composition to an animal. It is yet another object of this invention to have a method of preventing ILTV disease and NDV disease in an animal by administering an immunogenic effective amount of the immunogenic composition of this invention to an animal in need thereof. It is still a further object of this invention to have a method of reducing shedding of ILTV and NDV by an animal capable of being infected with ILTV and/or NDV by administering an immunogenic effective amount of the immunogenic composition of this invention to the animal.

It is an object of this invention to have a novel, chimeric virus that is a NDV LaSota strain and contains ILTV gD. It is a further object of this invention that the chimeric virus contains a negative-strand RNA having an RNA sequence that is (i) the equivalent of the reverse complement of SEQ ID NO: 17, (ii) a sequence that has at least 95%, 96%, 97%, 98%, or 99% identity to SEQ ID NO: 17, (iii) SEQ ID NO: 18, or (iv) a sequence that has at least 95%, 96%, 97%, 98%, or 99% identity to SEQ ID NO: 18. It is another object of this invention that the chimeric virus of this invention induces an immune response in an animal to both NDV and ILTV after administration of the chimeric virus to the animal. It is a further object of this invention to have an immunogenic composition containing this chimeric virus, one or more diluents, optionally an adjuvant, and optionally a carrier. It is another object of this invention to have a method of generating an immune response to NDV and ILTV in an animal by administering an immunogenic effective amount of this immunogenic composition to an animal. It is yet another object of this invention to have a method of preventing ILTV disease and NDV disease in an animal by administering an immunogenic effective amount of the immunogenic composition of this invention to an animal in need thereof. It is still a further object of this invention to have a method of reducing shedding of ILTV and NDV by an animal capable of being infected with ILTV and/or NDV by administering an immunogenic effective amount of the immunogenic composition of this invention to the animal.

It is an object of this invention to have a novel, purified expression vector has the polynucleotide sequence in SEQ ID NO: 13 or SEQ ID NO: 16, or a polynucleotide sequence that has at least 95%, 96%, 97%, 98% or 99% identity to SEQ ID NO: 13 or SEQ ID NO: 16.

It is an object of this invention to have a kit containing one or more of the immunogenic compositions described herein; optionally an adjuvant; and instructions on administration of the immunogenic composition to an animal.

It is another object of this invention to have an immunogenic composition that contains a first novel chimeric virus, a second novel chimeric virus, one or more diluents, optionally an adjuvant, and optionally a carrier, such that the first novel chimeric virus is a NDV LaSota strain containing ILTV gB (as described supra and infra) and the second novel chimeric virus is a NDV LaSota strain and ILTV gD (as described supra and infra). It is another object of this invention to have a method of generating an immune response to NDV and ILTV in an animal by administering an immunogenic effective amount of this immunogenic composition to an animal. It is yet another object of this invention to have a method of preventing ILTV disease and NDV disease in an animal by administering an immunogenic effective amount of the immunogenic composition of this invention to an animal in need thereof. It is still a further object of this invention to have a method of reducing shedding of ILTV and NDV by an animal capable of being infected with ILTV and/or NDV by administering an immunogenic effective amount of the immunogenic composition of this invention to the animal.

It is a further object of this invention to have an immunogenic composition that contains a first novel chimeric virus, a second novel chimeric virus, one or more diluents, optionally an adjuvant, and optionally a carrier, such that the first novel chimeric virus is a NDV LaSota strain containing ILTV gB (as described supra and infra) and the second novel chimeric virus is a NDV LaSota strain and ILTV gD (as described supra and infra), and such that the first novel chimeric virus has a concentration ranging from approximately 1% to approximately 99%; and the second novel chimeric virus has a concentration ranging from approximately 1% to approximately 99%. It is another object of this invention to have a method of generating an immune response to NDV and ILTV in an animal by administering an immunogenic effective amount of this immunogenic composition to an animal. It is yet another object of this invention to have a method of preventing ILTV disease and NDV disease in an animal by administering an immunogenic effective amount of the immunogenic composition of this invention to an animal in need thereof. It is still a further object of this invention to have a method of reducing shedding of ILTV and NDV by an animal capable of being infected with ILTV and/or NDV by administering an immunogenic effective amount of the immunogenic composition of this invention to the animal.

It is another object of the invention to have a kit containing a first container containing a first novel chimeric virus and at least one diluents, a second container containing the second novel chimeric virus and at least one diluents, optionally a third container containing an adjuvant, and instructions on administration of the first novel chimeric virus and the second novel chimeric virus to an animal, such that the first novel chimeric virus is a NDV LaSota strain containing ILTV gB (as described supra and infra) and the second novel chimeric virus is a NDV LaSota strain and ILTV gD (as described supra and infra).

It is an object of this invention to have a kit containing an immunogenic composition that contains a first novel chimeric virus, a second novel chimeric virus, one or more diluents, optionally an adjuvant, and optionally a carrier, such that the first novel chimeric virus is a NDV LaSota strain containing ILTV gB (as described supra and infra) and the second novel chimeric virus is a NDV LaSota strain and ILTV gD (as described supra and infra), and such that the first novel chimeric virus has a concentration ranging from approximately 1% to approximately 99%; and the second novel chimeric virus has a concentration ranging from approximately 1% to approximately 99%.

DETAILED DESCRIPTION OF THE INVENTION

Figure 1:
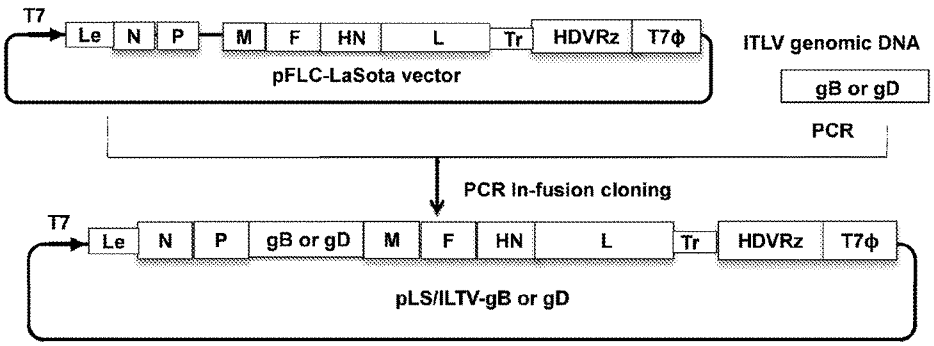
FIG. 1 illustrates the construction of pLS/ILTV-gB and pLS/ILTV-gD. The ORF of the ILTV gB gene or ILTV gD gene is inserted into the plasmid encoding NDV LaSota genes between the P and M genes as an additional transcription unit using the In-Fusion® PCR cloning kit. The direction of the T7 promoter is indicated by an arrow. HDVRz and T7Φ represent the site of the Hepatitis delta virus ribozyme and the T7 terminator sequences, respectively.

This invention involves a chimeric virus of NDV LaSota strain carrying polynucleotides encoding a heterologous protein, namely either glycoprotein B (gB) or glycoprotein D (gD) of ILTV. This chimeric virus, when administered to an animal, can induce an immune response in the animal to both NDV and to gB or gD. Further, it is a surprising and unexpected result based on prior work by the inventor that the immune response generated by this chimeric virus can protect the animal from infection by and/or diseases caused by NDV and ILTV. In this present invention, the polynucleotides encoding the heterologous antigen is placed between the coding sequences for NDV P and M proteins (see FIG. 1). This invention involves immunogenic compositions containing the chimeric virus, method of using the immunogenic compositions, the polynucleotide sequences of the chimeric viruses, and the expression vectors or plasmid used to generate the chimeric viruses.

In addition, an immunogenic composition can contain a mixture of rLS/ILTV-gB and rLS/ILTV-gD. One can produce each chimeric virus (rLS/ILTV-gB and rLS/ILTV-gD) independently of each other, storing one or both batches if necessary, and then mixing the two chimeric viruses together with proportions ranging from approximately 1% to approximately 99% for one chimeric virus and from approximately 1% to approximately 99% for the other chimeric virus prior to administering both chimeric viruses to the animal. Alternatively, an immunogenic composition containing rLS/ILTV-gB and an immunogenic composition containing rLS/ILTV-gD could be mixed together prior to administering the combined immunogenic composition to the animal. In another embodiment, one can infect cells in tissue culture with both rLS/ILTV-gB and rLS/ILTV-gD and then purify the chimeric viruses produced. For this alternatively embodiment, it may possibly be difficult to control, from batch to batch, the quantity of each chimeric virus in the immunogenic product; but that does not negate the ability to produce an immunogenic composition containing both chimeric viruses.

While combination vaccines which generate an immune response in an animal to NDV and to another virus are being sold commercially, these vaccines are simply a mixture of the two viruses, administered together. In contrast, the present invention is a chimeric virus of NDV encoding and expressing a heterologous protein (or antigen) from a different virus; in particular gB or gD of ILTV.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

Because this invention involves production and purification of recombinant virus expressing a heterologous antigen (a chimeric virus) that may be administered to an animal, the following definitions are provided to assist in describing this invention. The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein that gives rise to essentially one band in gel after being subjected to electrophoresis. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in daltons (Da), kilodaltons (kDa) or amino acid residue numbers. Proteins sizes are estimated from gel electrophoresis, from sequenced proteins, from derived amino acid sequences, or from published protein sequences.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98(1994)).

In addition to the degenerate nature of the nucleotide codons which encode amino acids, alterations in a polynucleotide that result in the production of a chemically equivalent amino acid at a given site, but do not affect the functional properties of the encoded polypeptide, are well known in the art. "Conservative amino acid substitutions" are those substitutions that are predicted to interfere least with the properties of the reference polypeptide. In other words, conservative amino acid substitutions substantially conserve the structure and the function of the reference protein. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide. Table 1 provides a list of exemplary conservative amino acid substitutions. Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

TABLE 1

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Glu | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Len, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

As contemplated herein, a polypeptide, protein, or peptide may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a non-enzymatic attachment of sugars, polysialylation (e.g., the addition of polysialic acid), glypiation (e.g., glycosylphosphatidylinositol (GPI) anchor formation), hydroxylation, iodination (e.g., of thyroid hormones), and phosphorylation (e.g., the addition of a phosphate group, usually to serine, tyrosine, threonine or histidine) are possible.

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes that are not found within the native (non-recombinant or wild-type) form of the cell or express native genes that are otherwise abnormally expressed—over-expressed, under-expressed or not expressed at all.

The terms "transgenic", "transformed", "transformation", and "transfection" are similar in meaning to "recombinant". "Transformation", "transgenic", and "transfection" refer to the transfer of a polynucleotide into the genome of a host organism (including a virus) or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of transferred polynucleotide in order for the transgenic organism or cell to live and/or grow. Polynucleotides that are transformed into a cell but are not integrated into the host's chromosome remain as an expression vector within the cell. One may need to grow the cell under certain conditions in order for the expression vector to remain in the cell or the cell's progeny. Further, for expression to occur the organism or cell may need to be kept under certain conditions. Host organisms or cells containing the recombinant polynucleotide can be referred to as "transgenic" or "transformed" organisms or cells or simply as "transformants", as well as recombinant organisms or cells. A virus containing polynucleotides encoding a foreign gene is referred to as a "chimeric virus".

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, *J. Chrom.* 255:137-149 (1983).

This invention utilizes routine techniques in the field of molecular biology. Basic texts disclosing the general methods of use in this invention include Green and Sambrook, 4th ed. 2012, Cold Spring Harbor Laboratory; Kriegler, *Gene Transfer and Expression: A Laboratory Manual* (1993); and Ausubel et al., eds., *Current Protocols in Molecular Biology,* 1994—current, John Wiley & Sons. Unless otherwise noted, technical terms are used according to conventional usage. Definitions of common terms in molecular biology maybe found in e.g., Benjamin Lewin, *Genes IX*, published by Oxford University Press, 2007 (ISBN 0763740632); Krebs, et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature; etc. There are various types of vectors including virus, plasmid, bacteriophages, cosmids, and bacteria. As used herein, a "viral vector" refers to recombinant viral nucleic acid that has been engineered to express a heterologous polypeptide (e.g., ILTV gB or ILTV gD or antigenic fragments thereof). The viral vector may include cis-acting elements for expression of the heterologous polypeptide. The recombinant viral nucleic acid typically is capable of being packaged into a helper virus that is capable of infecting a host cell. For example, the recombinant viral nucleic acid may include cis-acting elements for packaging. The chimeric virus maybe replication incompetent, attenuated, or at least does not cause disease. The chimeric virus may also induce an immune response against antigens normally present on the virus or encoded by the viral vector. The viral vector may be genetically altered by modern molecular biological methods (e.g., restriction endonuclease and ligase treatment, and rendered less virulent than wild type), typically by deletion of specific genes. For example, the recombinant viral nucleic acid may lack a gene essential for production of infectious or virulent virus.

The recombinant viral nucleic acid may function as a vector for an immunogenic ILTV protein by virtue of the recombinant viral nucleic acid containing polynucleotides which encoding for ILTV antigen(s). The recombinant viral nucleic acid, packaged in a chimeric virus, may be introduced into a subject by standard methods for inoculation of immunogenic compositions containing a live virus. An immunogenic composition of the invention can be administered at, for example, approximately $10^4$ to approximately $10^8$ viruses/dose, or approximately $10^6$ to approximately $10^9$ pfu/dose. Actual dosages of such an immunogenic composition can be readily determined by one of ordinary skill in the field of vaccine technology.

The transgene expressed in the chimeric virus disclosed herein may have the native polynucleotide sequence of ILTV gB and/or gD or may have a polynucleotide sequence that has been modified. For example, the presently disclosed chimeric virus may express polypeptides from polynucleotides that have been codons optimized, that is changed for enhanced expression in a particular host. For example, presently disclosed chimeric virus may include one or more polypeptides from ILTV where the encoding polynucleotide sequence is optimized to include codons that are most prevalent in an avian, such as a chicken. Codon usage for the chicken genome has been reported. (See Rao, et al., *DNA Res.,* 18(6):499-512 (2011)).

"Antibody" or "antibodies" encompass polyclonal and monoclonal antibody preparations, as well as preparations including hybrid antibodies; altered antibodies; chimeric antibodies; humanized antibodies (see, e.g., Riechmann, et al., *Nature* 332:323-327 (1988); Verhoeyan, et al., *Science* 239:1534-1536 (1988); and U.K. Patent Publication No. GB 2,276,169, published 21 Sep. 1994); hybrid antibody molecules (see, for example, Winter, et al., *Nature* 349:293-299 (1991); and U.S. Pat. No. 4,816,567); $F(ab')_2$ and F(ab) fragments; Fv molecules (noncovalent heterodimers, see, for example, Inbar, et al., *Proc. Natl. Acad. Sci. USA* 69:2659-2662 (1972); and Ehrlich, et al., *Biochem.* 19:4091-4096 (1980)); single-chain Fv molecules (sFv) (see, e.g., Huston, et al., *Proc. Natl. Acad. Sci. USA* 85:5879-5883 (1988)); dimeric and trimeric antibody fragment constructs; minibodies (see, e.g., Pack, et al., *Biochem.* 31:1579-1584 (1992); Cumber, et al., *J. Immunology* 149B:120-126 (1992)); and, any functional fragments obtained from such molecules, wherein such fragments retain specific-binding properties of the parent antibody molecule.

An "immunogenic composition" is a composition that contains one or more antigens such that the administration of the immunogenic composition to an animal results in an immune response to the antigen(s). Such an immune response in the animal may be a humoral and/or a cellular immune response to the antigen(s). The antigen(s) is also referred herein as an "immunogenic agent". A humoral response involves an antibody response; an immunized subject is induced to produce antibodies against an administered antigen (e.g., IgY, IgA, IgM, IgG, or other antibody isotypes). A cellular response or cell-mediated response may involve a cytotoxic T-cell response against cells expressing the peptides derived from an administered antigen in the context of a major histocompatibility complex (MHC) class I molecule. A cellular response is mediated by T-lymphocytes and/or other white blood cells. An "immunological response" or "immune response" to an antigen or immunogenic composition is, in an animal, the development, increase, or decrease of a humoral and/or a cellular immune response to the antigen or antigen present in the immunogenic composition. The immune response may be an increased or enhanced immune response (immuno-stimulatory) or a decrease or suppression of an immune response (immuno-suppressant). The immune response may be a systemic and/or localized immune response. As used herein, "potentiating" or "enhancing" an immune response means increasing the magnitude and/or the breadth of the immune response. For example, the number of cells that recognize a particular epitope may be increased ("magnitude") and/or the numbers of epitopes that are recognized may be increased ("breadth").

"Vaccination", "vaccinate", "immunization", "immunize", and "inoculate" are synonymous and are the administration of the antigens or immunogenic composition to the animal. These terms can also include removing immunological cells from the animal, allowing such immunological cells to interact with an antigen in-vitro, and then returning those immunological cells or their progeny back to the animal's body. Exemplary routes of administration of the antigens or immunogenic composition of this invention include, but not limited to, intramuscular injection, intraperitoneal injection, subdermal injection, intradermal injection, subcutaneous injection, intravenous injection, oral administration, sublingual administration, vaginal administration, rectal administration, transmucosally, transcutaneous adsorption, intranodal administration, intracoronary administration, intraarterial administration, intratracheal administration, intraarticular administration, intraventricular administration, intracranial administration, intraspinal administration, intraocular administration, aural administration, inhalation, eye drop administration, and intranasal administration. For this invention, oral administration may involve an animal eating a plant or plant cells which contain the antigen; or ingesting animal feed containing the antigens or immunogenic composition; or ingesting water containing the antigens or immunogenic composition. Such oral administration may result in mucosal immunity to the pathogens against which the antigens are directed. Another mode of administration is spraying the immunogenic composition on the animal. Vaccination and immunization involves inducing an immune response in the animal receiving the antigens or immunogenic composition. The immunogenic composition could be administered once to an animal. Alternatively, one can administer two or more dosages to the animal under a prime-boost regimen.

The immunogenic compositions may be administered prophylactically or therapeutically. In prophylactic administration, the immunogenic composition may be administered in an amount sufficient to induce immune responses for protecting against infection of the organism(s) which contain the antigen (i.e., a "immunogenic effective dose" or a "prophylactically effective dose"). In therapeutic administration, the immunogenic composition may be administered in an amount sufficient to induce immune responses for treating the disease or condition for which the subject suffers and for which the therapeutic agent being administered to the subject is designed to treat.

A prophylactic antigen or prophylactic immunogenic composition can be administered to the animal, especially to the young of the animal, to pregnant animals, and to elderly animals. The age of the young animal will vary depending on the animal's lifespan and if the young has maternal antibodies upon birth or, if the animal is a mammal, obtains maternal antibodies during nursing. Administering a prophylactic immunogenic composition to a pregnant animal may help stimulate the immune response of the fetus or baby animal prior to and shortly after birth. It may also stimulate the pregnant animal's immune system thereby improving the pregnant animal's health. Of course, administering prophylactic compositions to an elderly animal may boost the elderly animal's immune system to the antigen contained with the composition and thus help prevent the elderly animal from being infected with the bacteria, virus, or parasite containing the antigen. Administering an immunosuppressant composition would be considered a prophylactic administration in that one desires to reduce the animal's response to the antigen contained in the immunosuppressant composition prior to the animal's next expose to the antigen.

For immunogenic compositions and antigens, "treatment" refers to any of (i) the prevention of infection or reinfection, as in a traditional vaccine, (ii) the reduction or elimination of symptoms, (iii) the substantial or complete elimination of the pathogen in question, (iv) an enhanced immune response to the antigen or immunogenic composition administered to the animal, and/or (v) the reduction of a hypersensitive immune response in the animal. Treatment may be effected prophylactically (prior to infection or exposure to the antigen or infectious agent) or therapeutically (following infection or exposure to the antigen or infectious agent).

The immunogenic compositions disclosed herein may be formulated for administration to a subject in need thereof. Such immunogenic compositions can be formulated and/or administered in dosages and by techniques well-known to those skilled in the medical/veterinarian arts. The appropriate dose of the immunogenic composition of the present invention depends on several variables, such as but not limited to, the formulation, the route of administration, the animal's age, the animal's sex, the animal's weight, the time of administration, the excretion rate, reaction irritability, and condition of the particular subject and the route of administration. The immunogenic compositions may include carriers, diluents, or excipients as known in the art. Further, the compositions may include preservatives (e.g., anti-microbial or anti-bacterial agents such as benzalkonium chloride) or adjuvants. One of ordinary skill in the art can determine the appropriate dose by administering the antigen to the animal and assaying for an increase or, if applicable, a decrease in the immune response.

One method of assessing efficacy of an immunogenic composition involves monitoring an infection after administration of the immunogenic composition. One method of assessing efficacy of prophylactic administration of the immunogenic composition involves monitoring immune responses against the antigens in the immunogenic composition after administration of the immunogenic composition. Another method of assessing the immunogenicity of the antigens of the immunogenic composition is to express the antigens recombinantly and to screen an animal's sera or mucosal secretions by immunoblot. A positive reaction between the antigen and the animal's serum indicates that the animal previously mounted an immune response to the antigen in question—that is, the antigen is an immunogen. This method may also be used to identify immunodominant proteins and/or epitopes.

Another method involves intentionally infecting the vaccinated animal or allowing the vaccinated animal to be in the presence of infected, non-vaccinated animals and monitoring for symptoms of illness. Alternatively, one may monitor immune responses both systemically (such as monitoring the level of $IgG_1$ and $IgG_{2a}$ production) and mucosally (such as monitoring the level of IgA production) against the antigens in the immunogenic composition after administration of the immunogenic composition. Typically, serum specific antibody responses are determined post-immunization but pre-challenge, whereas mucosal specific antibody body responses are determined post-immunization and post-challenge.

Immunogenic compositions of the present invention may be used either alone or in combination with other antigens and/or optionally with an immunoregulatory agent ("adjuvant"). An adjuvant is a compound or mixture that enhances the immune response to an antigen. An adjuvant can serve as a tissue depot that slowly releases the antigen and also as a lymphoid system activator that non-specifically enhances the immune response. Examples of adjuvants which may be employed include MPL-TDM adjuvant (monophosphoryl Lipid A/synthetic trehalose dicorynomycolate, e.g., available from GSK Biologics). Another suitable adjuvant is the immunostimulatory adjuvant AS021/AS02 (GSK). These immunostimulatory adjuvants are formulated to give a strong T cell response and include QS-21, a saponin from *Quillay saponaria*, the TL4 ligand, a monophosphoryl lipid A, together in a lipid or liposomal carrier. Other adjuvants include, but are not limited to, *E. coli* LT (or LT-B, native or toxoid), squalene and squalene-like compounds, nonionic block co-polymer adjuvants (e.g., CRL1005), aluminum phosphates (e.g., $AlPO_4$), R-848 (a Th1-like adjuvant), imiquimod, PAM3CYS, poly (LC), loxoribine, potentially useful human adjuvants such as BCG (bacille Calmette-Guerin) and *Corynebacterium parvum*, CpG oligodeoxynucleotides (ODN), cholera toxin derived antigens (e.g., CTA1-DD), lipopolysaccharide adjuvants, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), water-in-oil-in-water emulsion, keyhole limpet hemocyanins, and dinitrophenol. Adjuvants which are capable of preferential stimulation of the Th1 cell response are described in International Patent Application No. WO 94/00153 and WO 95/17209.

The immunogenic composition may be prepared for administration by formulating an effective immunization dosage of the antigen(s) (chimeric virus) with a pharmaceutically acceptable carrier or diluent, such as physiological saline or tissue culture medium. The expression "effective immunization dosage" is that amount which will induce immunity in an animal against challenge using the infectious agent or that amount which will induce immunity in an animal against a challenge with the infectious agent against which the antigen is directed Immunity is considered as having been induced in an animal when the level of protection for the animal is significantly higher than that of an unvaccinated control group.

The immunogenic composition of this invention may contain one or more pharmaceutically acceptable carriers. Non-limited examples of such carriers include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxy benzoate, propyl hydroxy hydroxy benzoate, talc, stearic acid, magnesium, and mineral oils. In addition to the above ingredients of the pharmaceutical composition according to the present invention may further comprise lubricants, wetting agents, sweetening agents, flavoring agents, emulsifiers, suspending agents, preservatives, etc. Suitable pharmaceutically acceptable carriers and formulations are described in detail in *Remington's Pharmaceutical Sciences* (19th ed., 1995).

The invention also includes kits containing one or more containers of the immunogenic compositions and/or antigens of the invention. The immunogenic composition can be in liquid form or can be lyophilized; as can be the antigens. Suitable containers for the immunogenic compositions and/or antigens include, for example, bottles, jugs, vials, syringes, and test tubes. Containers can be formed from a variety of materials, including glass or plastic. A container may have a sterile access port (for example, the container may be an intravenous solution bag or a vial having a stopper pierceable by a hypodermic injection needle). The kit can also contain a second container inside of which is a pharmaceutically-acceptable buffer, such as phosphate-buffered saline, Ringer's solution, or dextrose solution. The kit can also contain other materials useful to the end-user, including other pharmaceutically acceptable formulating solutions such as buffers and/or diluents, filters, needles, and syringes or other delivery devices. The kit may optionally include an adjuvant in a container. The kit can also contain written instructions for administering the immunogenic composition and/or antigen and other contents of the kits to subjects. The written instructions may describe methods for inducing an immune reaction or methods for treating infections. The invention also includes a delivery device pre-filled with the immunogenic composition of the invention.

The invention also provides for the immunogenic composition described herein to be used as a medicament. A medicament is preferably able to generate an immune response in an animal. The invention also provides for the use of the immunogenic composition of the invention in the manufacture of a medicament for generating an immune response in an animal. In one embodiment, the medicament is a vaccine or an immunostimulatory composition or an immunosuppressant composition.

The invention provides methods for inducing or increasing an immune response using the immunogenic composition. The immune response is preferably protective and can include antibodies and/or cell-mediated immunity (including systemic and mucosal immunity). Immune responses include booster responses. The invention also provides methods for suppressing or decreasing an immune response in the animal to the antigen using an immunogenic composition. Such a suppression of an immune response may be useful if the animal is hypersensitive to the antigen.

As used herein, the terms "subject," "host," "animal" or "individual" typically refer to an avian at risk for acquiring an infection by infectious laryngotracheitis virus (ILTV). The terms "subject," "host," or "individual" may be used interchangeably. Suitable avian for the disclosed immunogenic composition, antigens, methods and kits may include poultry, ducks, game birds (including, but not limited to, quail, pheasants, and geese), ratites (including, but not limited to, ostrich) and other domesticated birds and avian pets. The term "poultry" denotes birds of the order Galliformes, such as, for example, ordinary domestic fowl (chicken, turkeys, ducks, etc.) and include the species *Gallus gallus* and the subspecies *Gallus gallus domesticus, Meleagris gallopavo, Meleagris gallopavo*, and *Meleagris ocellata.*

Having described the invention, below are examples illustrating the generation and efficacy of the invention.

Example 1 Construction of Recombinant LaSota cDNA Containing the gB or gD Gene of ILTV The previously generated full-length LaSota cDNA plasmid is used as a backbone (Hu, et al., *Vaccine* 29:8624-8633 (2011)) for generating the chimeric virus. This plasmid contains a T7 polymerase operably linked to cDNA encoding NDV genes (the reverse complement of NDV genes) followed by the hepatitis delta virus ribozyme gene and T7 terminator sequences. cDNA containing the coding sequence of ILTV gB (SEQ ID NO: 1), which encodes the amino acid sequence in SEQ ID NO: 2, or the coding sequence of ILTV gD (SEQ ID NO: 3), which encodes the amino acid sequence in SEQ ID NO: 4, is inserted into the LaSota plasmid between the phosphoprotein (P) and matrix (M) genes as an additional transcription unit using the In-Fusion® PCR cloning kit (Clontech, Mountain View, Calif.). Primers sets used to amplify the cDNA fragments and the linearized vector backbone are designed to contain a 15-nucleotide (nt) overlapping region of homology at their 5' end (see Table 1). The pfu Ultra™ II Fusion HS DNA polymerase (Stratagene, La Jolla, Calif.) is used for the PCR amplification of the cDNAs or plasmid, according to the manufacturer's instructions, throughout the cloning process unless otherwise indicated.

The full-length LaSota cDNA plasmid is linearized by PCR amplification with a pair of specific primers (Insert vec up and Insert vec down, Table 2) in the intergenic region between the P and M genes. The open reading frame (ORF) of the ILTV gB or ILTV gD gene flanked with the NDV gene start (GS) and gene end (GE) sequences are amplified by PCR from the genomic DNA of ILTV 63140 strain (Spatz, et al., *Virus Genes* 44:273-285 (2012)) with gene-specific primers (Plant-gB/GFP F and Plant-gB/GFP R for the gB; Plant-gD/GFP F and Plant-gD/GFP R for gD, Table 2). Subsequently the ILTV gB gene or ILTV gD gene ORF fragment is cloned into the linearized LaSota plasmid using the In-Fusion® PCR cloning kit (Clontech, Mountain View, Calif.). The resulting NDV and ILTV recombinant cDNA plasmids are designated as pLS/ILTV-gB and pLS/ILTV-gD, respectively (see FIG. 1). The entire DNA sequence of plasmid pLS/ILTV-gB (see FIG. 1) is in SEQ ID NO: 13. The cDNA sequence of the chimeric virus (rLS/ILTV-gB virus; aka NDV LaSota expressing ILTV gB) is in SEQ ID NO: 14. This cDNA sequence is the reverse complement of the chimeric virus' negative-strand RNA genome (see SEQ ID NO: 15). The entire DNA sequence of plasmid pLS/ILTV-gD (see FIG. 1) is in SEQ ID NO: 16. The cDNA sequence of the chimeric virus (rLS/ILTV-gD virus; aka NDV LaSota expressing ILTV gD) is in SEQ ID NO: 17. This cDNA sequence is the reverse complement of the chimeric virus' negative-strand RNA genome (see SEQ ID NO: 18).

TABLE 2

Primer sequences used in the study

| Primer | Primer Sequence[e] | Primer Name |
|---|---|---|
| 1[a] | 5'-GGTGGCTACAACTATCAACTAAACT-3' (SEQ ID NO: 5) | Insert vec Up |
| 2[a] | 5'-GTGTGTAACTACCGTGTACTAAGC-3' (SEQ ID NO: 6) | Insert vec Down |
| 3[b] | 5'-atagttgtagccaccATGCAATCCTACATCG-3' (SEQ ID NO: 7) | Plant-gB/GFP F |
| 4[b] | 5'-gtagttacacacagcTTATTCGTCTTCGCTTTC-3' (SEQ ID NO: 8) | Plant-gB/GFP R |
| 5[c] | 5-atagttgtagccaccATGCACCGTCCTCATC-3' (SEQ ID NO: 9) | Plant-gD/GFP F |
| 6[c] | 5'-gtagttacacacagcTTAGCTACGCGCGCAT-3' (SEQ ID NO: 10) | Plant-gD/GFP R |
| 7[d] | 5'-atagttgtagccaccATGGTGAGCAAGCAGATC-3' (SEQ ID NO: 11) | Plant-GFP F |
| 8[d] | 5'-acggtagttacacacTCACACCCACTCGTGCAG-3' (SEQ ID NO: 12) | Plant-GFP R |

[a]Primers 1 to 2 were used to PCR amplify or linearize the pFLC-LaSota vector.
[b]Primers 3 to 4 were used to amplify the cDNA fragments containing the ILTV gB gene ORF.
[c]Primers 5 to 6 were used to amplify the cDNA fragments containing the ILTV gD gene ORF.
[d]Primers 7 to 8 were used to amplify the cDNA fragments containing the GFP gene ORF.
[e]Nucleotides shown in lower case letters represent homology sequences with a vector backbone, which were used to facilitate the restriction endonuclease independent cloning using the In-Fusion ® PCR cloning kit (Clontech).

Example 2 Generation of Chimeric Viruses (Virus Rescue and Propagation)

Rescue of the recombinant NDV LaSota/ILTV-gB chimeric virus (rLS/ILTV-gB) and the NDV LaSota/ILTV-gD chimeric virus (rLS/ILTV-gD) is performed by transfection of the full-length plasmids (pLS/ILTV-gB and pLS/ILTV-gD, respectively) and supporting plasmids (three plasmids which express the NDV NP, P, and L proteins, respectively, in the transfected cells) into HEp-2 cells as described in Estevez, et al., *Virus Research* 129(2):182-190 (2007) and in Yu, et al., *World J. of Vaccines* 3:130-139 (2013). The rescued viruses, which are confirmed by a positive hemagglutination assay (see D. J. Alexander, "*Newcastle Disease Virus and Other Avian Paramyxoviruses*," pp. 156-163 In: Swayne, et al., (eds.), *A Laboratory Manual for the Isolation and Identification of Avian Pathogens,* 4$^{th}$ edition, American Association of Avian Pathologists, Kennett Square (1998)) are plaque purified three times in DF-1 cells and finally amplified in SPF chicken embryos three times. The allantoic fluid is harvested, aliquoted, and stored at −80° C. as a stock. The complete genomic sequences of the rescued viruses are determined by direct sequencing of the RT-PCR products amplified from the viral genomic RNA as described previously in Hu, et al., *Vaccine* 29(47):8624-8633 (2011) and are set forth in SEQ ID NO: 15 for rLS/ILTV-gB and SEQ ID NO: for rLS/ILTV-gD.

In addition to the generation of rLS/ILTV-gB chimeric virus and rLS/ILTV-gD chimeric virus, a recombinant NDV LaSota virus containing the green fluorescent protein (GFP) as a control is generated. The open reading frame of the ILTV gB gene in the pLS/ILTV-gB plasmid is replaced with the open reading frame of GFP gene using the In-Fusion® PCR cloning kit (Clontech, Mountain View, Calif.) with paired specific primers (Insert vec up and Insert vec down for linearizing the vector, and Plant-GFP F and Plant-GFP R for amplifying the GFP open reading frame from the pAAV-hrGFP plasmid, see Table 2). Subsequently the resulting plasmid, designated as pLS-GFP, is used to rescue the rLS-GFP chimeric virus as described previously (Hu, et al. (2011)).

Example 3 Virus Titration, Pathogenicity, and Growth Dynamics Assays

Analysis of the chimeric viral stock titers, rLS/ILTV-gB and rLS/ILTV-gB, are completed using the standard hemagglutination assay test described in Example 2 in a 96-well microplate, the 50% tissue infectious dose ($TCID_{50}$) assay on DF-1 cells, and the 50% egg infective dose ($EID_{50}$) assay in 9-day-old SPF chicken embryos and compared to the parental NDV LaSota strain. The $TCID_{50}$ assay and the $EID_{50}$ assay are performed using the protocols set forth in Alexander (1998). Pathogenicity of the recombinant viruses is assessed by performing the standard mean death time (MDT) and intracerebral pathogenicity index (ICPI) tests and also compared to the parental NDV LaSota strain. See, Alexander (1998) for the protocols for the MDT assay and the ICPI assay. Cytopathic effects (CPE) and growth dynamics of the recombinant viruses are examined in DF-1 cells and compared to the parental virus as described in Hu, et al. (2011).

Example 4 IFA for gB and gD Expressed by Chimeric Viruses

To examine expression of the ILTV-gB or ILTV-gD protein by the recombinant viruses, DF-1 cells are grown in a 12-well plate and are infected with rLS/ILTV-gB, rLS/ILTV-gD (produced above in Examples 1 and 2), or the parental NDV LaSota strain (negative control) at a multiplicity of infection (MOI) of 0.01. At 24 hours post-infection, the infected cells are washed three times with 1×PBS and fixed with 10% zinc formalin (Fisher Scientific, Pittsburgh, Pa.) for 15 minutes at room temperature, followed by adding 0.5% Triton X-100 (Sigma-Aldrich, St. Louis, Mo.) to permeabilize the DF-1 cells at room temperature for 10 minutes. The permeabilized DF-1 cells are blocked with 5% goat serum (SouthernBiotech, Birmingham, Ala.) for 30 minutes at 37° C. using manufacturer's suggested protocol. After blocking, the DF-1 cells are incubated with chicken anti-ILTV serum (a gift of Dr. Maricarmen Garcia from the University of Georgia, Athens, Ga.) and/or mouse anti-NDV HN monoclonal antibody (Mab, a gift of Dr. Ron Iorio from University of Massachusetts Medical School, Boston, Mass.), then with fluorescein (FITC) conjugated goat anti-chicken IgG (H+L) (SouthernBiotech, Birmingham, Ala.) and/or Alexa Fluor® 568 labeled goat anti-mouse IgG (H+L) (Life Technologies, Carlsbad, Calif.) for 30 minutes for each incubation at 37° C. according to manufacturers' suggested protocol. The cells are washed three times with 1×PBS after each treatment. Finally, the cells are mounted with Fluoromount-G® (SouthernBiotech, Birmingham, Ala.). Fluorescence is examined and digitally photographed using an inverted fluorescence microscope at 100× magnifications with a matching wavelength filter for FITC or Alexa Fluor® 568 (Nikon, Eclipse Ti, Melville, N.Y.).

The DF-1 cells infected with parental NDV LaSota virus (negative control) fluoresce red when exposed to mouse anti-NDV HN monoclonal antibody and Alexa Fluor® 568 labeled goat anti-mouse IgG, but did not fluoresce when exposed to chicken anti-ILTV serum and FITC-conjugated goat anti-chicken IgG. Thus, the parental NDV LaSota virus infected DF-1 cells do not express ILTV gB or gD. DF-1 cells infected with the chimeric virus, rLS/ILTV-gB, fluoresce green when exposed to chicken anti-ILTV serum and FITC-conjugated goat anti-chicken IgG and red when exposed to mouse anti-NDV HN monoclonal antibody and Alexa Fluor® 568 labeled goat anti-mouse IgG. When exposed to both labels, many DF-1 cells fluoresce a combination of red and green. Similarly, DF-1 cells infected with the chimeric virus, rLS/ILTV-gD, fluoresce green when exposed to chicken anti-ILTV serum and FITC-conjugated goat anti-chicken IgG and red when exposed to mouse anti-NDV HN monoclonal antibody and Alexa Fluor® 568 labeled goat anti-mouse IgG. When exposed to both labels, many DF-1 fluoresce a combination of red and green.

Example 5 Inoculation of Leghorn Chickens with Immunogenic Composition

To evaluate immune response generated by the chimeric viruses (immunogenic compositions) and if any protective immunity is generated against infectious laryngotracheitis, SPF Leghorn chickens are inoculated with the chimeric viruses (rLS/ILTV-gB or rLS/ILTV-gD). One hundred and five 1-day-old SPF Leghorn chickens are randomly divided into seven groups of 15 birds. Each bird in group 1 is inoculated with 100 μl of phosphate buffered saline (PBS) via intranasal (IN) and eye drop (ED) routes as unvaccinated controls. Birds in groups 2 and 3 are vaccinated with 100 μl of rLS-GFP ($1.0\times10^7$ $TCID_{50}$/ml) per bird via IN/ED routes as NDV LaSota vector controls; birds in groups 4 and 5 are vaccinated with 100 μl of rLS/ILTV-gB ($1.0\times10^7$ $TCID_{50}$/ml) produced per Example 1 and 2 per bird via IN/ED routes; and birds in groups 6 and 7 are vaccinated with 100 μl of rLS/ILTV-gD ($1.0\times10^7$ $TCID_{50}$/ml) produced per Example 1 and 2 per bird via IN/ED routes. At 21 days post-vaccination (DPV), the birds in groups 1, 2, 4 and 6 are challenged with virulent ILTV at a dose of $10^4$ $TCID_{50}$/ml per birds (see FIG. 2A). The birds in groups 3, 5, and 7 are challenged with the virulent ILTV at the same dose at 28 DPV (see FIG. 2B). Blood samples are collected from each bird immediately before challenge for detection of antibody responses by the hemagglutination inhibition assay (as described above). Tracheal and ocular swabs are collected from each of the birds at 4 days post-challenge (DPC) for detection of ILT virus shedding by quantitative real-time PCR (qPCR) using the protocol indicated below.

Tracheal swabs are suspended in 1.0 mL of sterile phosphate buffered saline containing 2% antibiotic-antimycotic (Invitrogen, Carlsbad, Calif.) and 2% newborn calf serum (Invitrogen, Carlsbad, Calif.). All samples are stored at −20° C. until further processed. Total DNA of the clinical samples is purified using the PBS/mucus eluent and the MagaZorb® DNA Mini-Prep Kit (Promega Corp., Madison, Wis.) in a 96-well format according to the manufacturer's instructions. All buffers used in the DNA purification procedure are supplied with the kit. Briefly, 200 μL PBS/mucus eluent is transferred to a 96-well plate. 20 μL Proteinase K solution (20 mg/ml) are added to each suspension and mixed by manual swirling. Cells are lysed with the addition of 200 μL of Lysis Buffer. The plate is covered with adhesive film and is pulse-vortex mixed until the mixture is homogenous. Samples are incubated for 10 minutes at 56° C. To bind DNA, 500 μL of Binding Buffer are added to each sample and thoroughly mixed. Next, 20 μL MagaZorb® Reagent is added. Samples are then incubated at room temperature for 10 minutes, with manual mixing every 2 minutes. MagaZorb® particles are pelleted for more than 10 minutes using a magnetic rack (Ambion, Life Technologies, Carlsbad, Calif.). Supernatants are removed by aspiration. Samples are washed twice with 1 mL Wash Buffer. Plates are inverted several times to ensure adequate washing. The particles are again pelleted using a magnetic rack. Supernatants are removed by aspiration, and the particles containing DNA are suspended in 200 μL of Elution Buffer and incubated at room temperature for 10 minutes, with manual mixing every 2 minutes. Particles are again pelleted using the magnetic rack. Finally, the supernatant containing the purified DNA is transferred to a fresh 96 well plate and is stored at −20° C. until further processed.

qPCR is performed on an Applied Biosystems 7500 Fast Real-Time PCR System (Life Sciences, Carlsbad, Calif.). The multiplex reaction contained specific primers and probes for the detection of the $U_L44$ gene of infectious laryngotracheitis virus (encoding glycoprotein C) and the endogenous control gene (avian α2-collagen gene) (reference). The nucleotide sequences of these primers and probes are in Table 3. The $U_L44$ forward primer and $U_L44$ reverse primer generate a 103 by amplicon (SEQ ID NO: 22). The α2-collagen forward primer and α2-collagen reverse primer generates a 96 by amplicon (SEQ ID NO: 26). Multiplex qPCR reactions are set up in a final volume of 25 μL as follows: 1× Universal TaqMan Master Mix with UNG (Life Technologies, Carlsbad, Calif.), 500 nM of $U_L44$ forward primer, 500 nM of $U_L44$ reverse primer, 500 nM of α2-collagen forward primer, 500 nM of α2-collagen reverse primer, 100 nM of $U_L44$-FAM-TAMRA probe, 100 nM of α2-collagen-VIC®-TAMRA probe, and 5.0 μL of DNA template (approximately 10-300 ng). The reaction is carried out in a thermal cyclical program with the following parameters: 50° C. for 2 minutes followed by 95° C. for 10 minutes; followed by a two-step PCR with 40 cycles of denaturation at 95° C. for 15 seconds and annealing/extension at 60° C. for 1 minute. A threshold value of 0.05 is used for evaluation of multiple 96-well plates. Samples with any recorded threshold cycle number (Ct) value are considered positive and samples with no recorded Ct value are considered negative.

TABLE 3

| Primer/Probe Name | Sequence |
|---|---|
| $U_L44$ forward primer | 5'-CCTTGCGTTTGAATTTTTCTGT-3' (SEQ ID NO: 19) |
| $U_L44$ reverse primer | 5'-TTCGTGGGTTAGAGGTCTGT-3' (SEQ ID NO: 20) |
| $U_L44$-FAM-TAMRA probe | 6-FAM-5'-CAGCTCGGTGACCCCATTCTA-3'-TAMRA (SEQ ID NO: 21) |
| α2-collagen forward primer | 5'-GGGAACTGGAGAACCCAATTTT-3' (SEQ ID NO: 23) |
| α2-collagen reverse primer | 5'-CGTGCCGCTGTCTCTACCAT-3' (SEQ ID NO: 24) |
| α2-collagen-VIC-TAMRA probe | 6-VIC-5'-CCCTTAACTGAGTTCCCCAGCTACTGCAG-3'-TAMRA (SEQ ID NO: 25) |

6-FAM ™-6-carboxyfluorescein
TAMRA-carboxytetramethylrhodamine
6-VIC ®-Life Technologies' proprietary fluorescent compound After vaccination, all birds appear healthy without any signs of vaccine induced side-effects. Detection of NDV antibody response show that all of the LaSota vector immunized birds, the rLS/ILTV-gB immunized birds, the rLS/ILTV-gD immunized birds, and the rLS-GFP immunized birds seroconvert and became seropositive, whereas the PBS control birds contained no NDV antibodies (see Table 4). This result demonstrates that the immunogenic compositions (the chimeric viruses) induced a comparable antibody response as strong as that of the parental NDV vaccine. Because it is well documented that the ILTV antibody response does not necessarily correlate with the disease protection, the ILTV antibody response is not measured.

TABLE 4

| | Antibody responses | |
|---|---|---|
| Inoculant | Seropositive birds | NDV HI titer[a] |
| PBS | 0/15 | 0 |
| rLS-GFP | 30/30 | 3.83 ± 0.95 |

TABLE 4-continued

| | Antibody responses | |
|---|---|---|
| Inoculant | Seropositive birds | NDV HI titer[a] |
| rLS/ILTV-gB | 30/30 | 3.33 ± 0.66 |
| rLS/ILTV-gD | 30/30 | 3.47 ± 1.25 |

[a]Hemagglutination inhibition (HI) titer is expressed as $\log_2$ of the mean ± standard deviation.

Figure 2A:
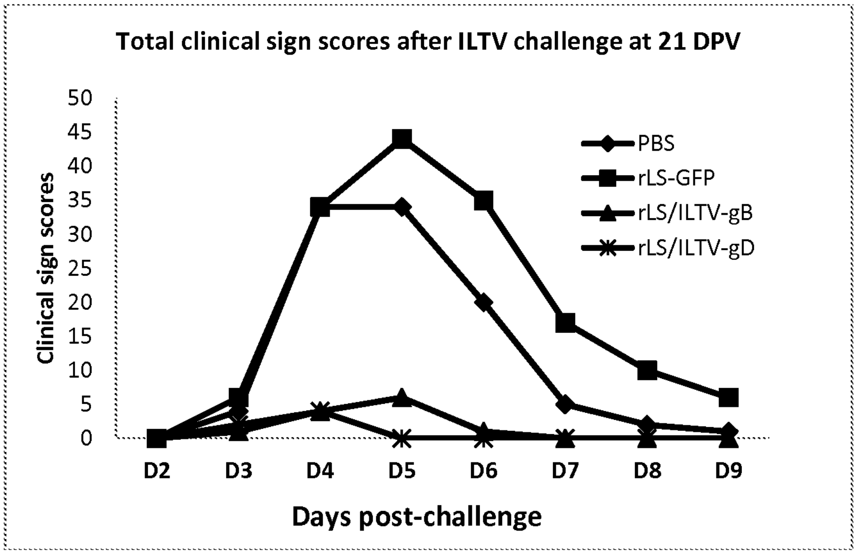
FIG. 2A illustrates the total clinical sign scores of specific-pathogen-free (SPF) chickens after ILTV challenge at 21 days post-inoculation with rLS-GFP (squares), rLS/ILTV-gB (triangles), rLS/ILTV-gD (asterisks), or mock inoculation (phosphate buffered solution (PBS)) (diamonds).
Figure 2B:
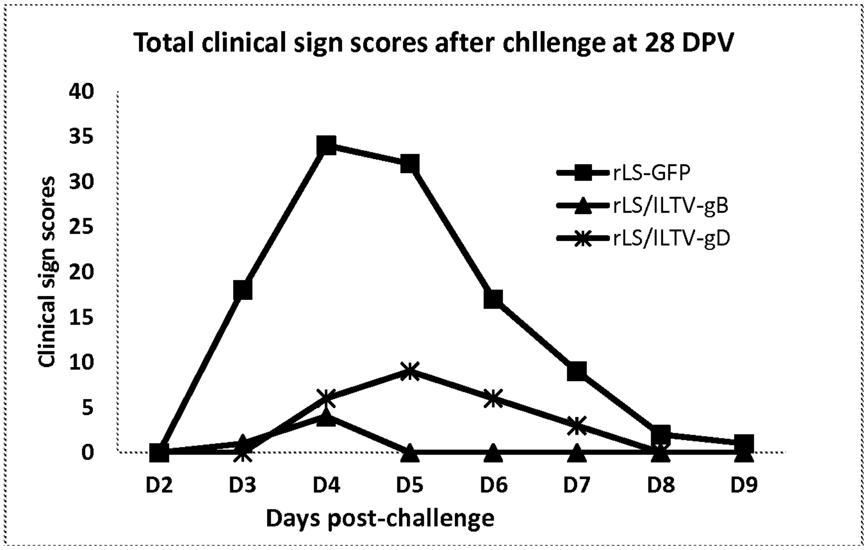
FIG. 2B illustrates the total clinical signs of specific-pathogen-free chickens after ILTV challenge at 28 days post-inoculation with rLS-GFP (squares), rLS/ILTV-gB (triangles), and rLS/ILTV-gD (asterisks).

From day 3 DPC, all of the birds in the unvaccinated (inoculated with PBS) and the LaSota vector (rLS-GFP) vaccinated groups display typical disease signs, showing conjunctivitis, depression or dyspnea, which are scored 1-3 depending on the severity of disease signs (see FIG. 2A and FIG. 2B). The infected birds show peak clinical signs between 4-6 DPC with 10-20% mortality, and gradually decrease in severity thereafter. In contrast, more than 90% of the rLS/ILTV-gB vaccinated chickens and the rLS/ILTV-gD vaccinated chickens show no disease signs, and only 2-5 birds display very mild clinical signs at 4-7 DPC (see FIG. 2A and FIG. 2B) in the chimeric virus groups.

Figure 3:
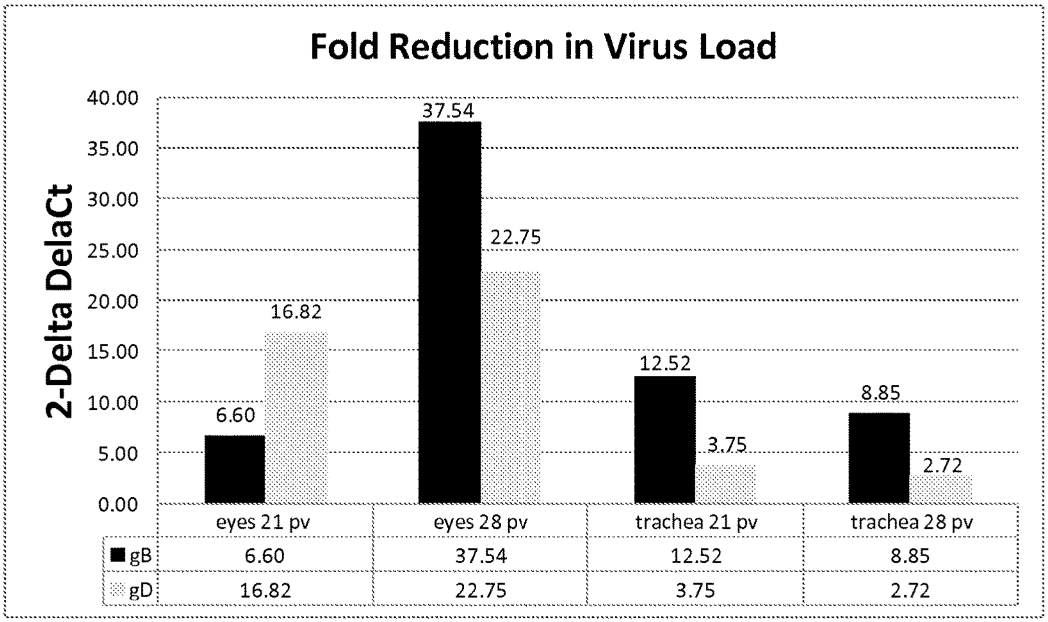
FIG. 3 shows the reduction in relative ILTV shedding load in tracheal lumen and tears of ILTV-challenged (strain 63140) birds at 4 days post-challenge, where challenge occurred at 21 and 28 days post-inoculation with rLS/ILTV-gB (black bars) or rLS/ILTV-gD (grey bars) as compared to the shedding of ILTV from rLS-GFP inoculated birds (control). Ct values for the gC amplicon are compared to Ct values of the endogenous control (collagen amplicon) using the relative $2^{-DeltaDelta}$ method.

Detection of the presence of the challenge virus in the tears as measured by the presence of viral DNA show that the chickens immunized with the rLS/ILTV-gB shed significantly less ILT challenge virus; 6-fold reduction in ILTV load (P<0.01) in tears collected 21 days post-immunization, and 37-fold reduction in ILTV load (P<0.01) in tears collected 28 days post-immunization than in the same time samples from birds in the control group (inoculated with rLS-GFP) (see FIG. 3). In tear samples collected 21 and 28 days post-immunization a 16- and 22-fold reduction of ILTV load, respectively (P<0.01) is quantified in chickens innoculated with the rLS/ILTV-gD. This reduction in virus shedding is in agreement with the clinical sign observations.

Detection of the presence of the challenge virus in the tracheal lumen as measured by the presence of viral DNA show that the chickens innoculated with the rLS/ILTV-gB shed significantly less ILT challenge virus, 12-fold reduction in ILTV load (P<0.01) in tears collected 21 days post-immunization and 8.8-fold reduction in ILTV load (P<0.01) in tracheal samples collected 28 days post-inoculation than in the same time samples from birds in control group (inoculated with rLS-GFP) (see FIG. 3). In tracheal samples collected 21 and 28 days post-inoculation a 3.75- and 2.72-fold reduction of ILTV load, respectively, (P<0.01) is quantified in chickens inoculated with the rLS/ILTV-gD. This reduction in virus shedding is in agreement with the clinical sign observations.

Example 6 Chimeric Virus Expressing ILTV gB v CEO and TCO ILTV Vaccines

One hundred and twenty 3-week-old commercial broilers are randomly divided into six groups of 20 birds. Each bird in groups 1-3 is inoculated via IN/ED routes with 100 µl of PBS, rLS-GFP ($1.0\times10^7$ $TCID_{50}$/ml), or rLS/ILTV-gB ($1.0\times10^7$ $TCID_{50}$/ml), respectively. Birds in groups 4 and 5 are vaccinated with one dose of commercial ILTV vaccine, either chicken embryo origin ILTV vaccine (CEO) or with tissue culture origin ILTV vaccine (TCO), per bird via the eye-drop route. Birds in group 6 are untreated and serve as body-weight gain controls. At 21 DPV, the birds in groups 1-5 are challenged with virulent ILTV in a dose of $10^4$ $TCID_{50}$/ml per bird. The serum samples are collected immediately before vaccination and challenge. The tracheal and ocular swab samples are collected at 4 DPC. All serum and swab samples are examined as described in Example 5 above.

After vaccination, all birds appear healthy without any signs of vaccine induced side-effects. Detection of NDV antibody response from the sera collected immediately before challenge show that all of the LaSota vector inoculated birds and rLS/ILTV-gB inoculated birds become NDV seropositive (see Table 5). As expected, the unvaccinated (PBS control), and the ILTV CEO and TCO inoculated birds do not have detectable anti-NDV antibodies (Table 4).

TABLE 5

| | Antibody responses | |
|---|---|---|
| Inoculant | Seropositive birds | NDV HI titer[a] |
| PBS | 0/20 | 0 |
| rLS-GFP | 20/20 | 3.85 ± 0.93 |
| rLS/ILTV-gB | 20/20 | 3.05 ± 0.83 |
| CEO | 0/20 | 0 |
| TCO | 0/20 | 0 |

Figure 4:
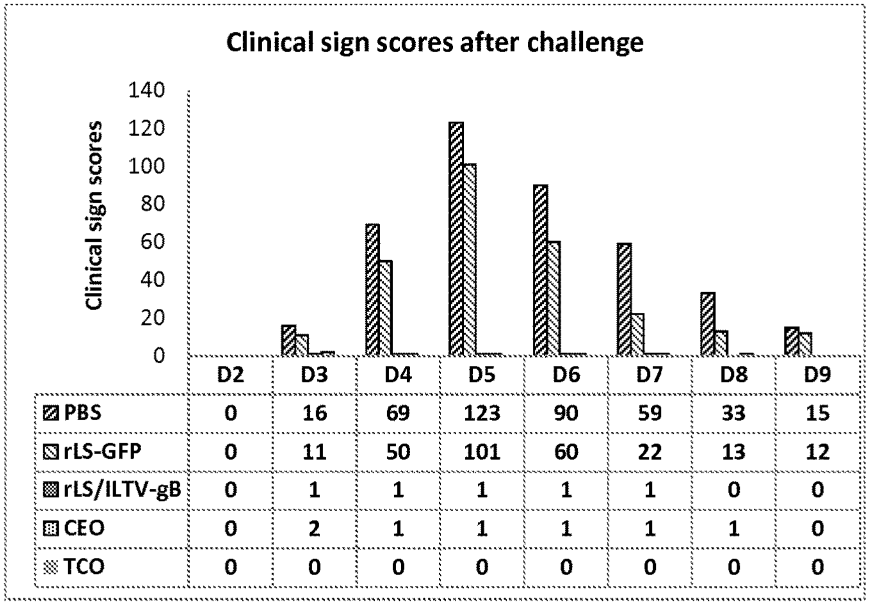
FIG. 4 shows the total clinical sign scores of broilers after three days post-challenge with virulent ILTV at 21 days post-inoculation with rLS-GFP, rLS/ILTV-gB, CEO, TCO, or mock inoculation (PBS).

[a]Hemagglutination inhibition (HI) titer was expressed as $\log_2$ of the mean ± standard deviation From day 3 post challenge, all of the birds in the unvaccinated group (inoculated with PBS) and the LaSota vector (rLS-GFP) vaccinated group display typical signs of disease. The infected birds show peak clinical signs between 4-6 DPC and gradually decrease in severity thereafter (see FIG. 4). There are 50% mortality for birds in the PBS group and 5% mortality in the LaSota vector group, respectively. In contrast, there is only one bird from the rLS/ILTV-gB inoculated broiler group and one from the CEO inoculated broiler group which show any clinical signs at 4-5 DPC. They are scored as very mild clinical signs (see FIG. 4).

Figure 5:
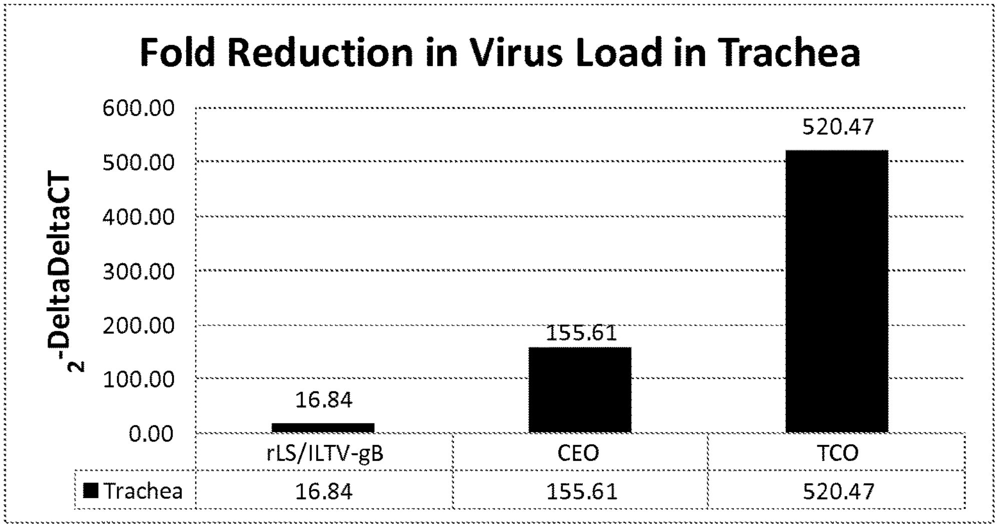
FIG. 5 shows the relative reduction in viral shedding (ILTV) in trachea of ILTV-challenged (strain 63140) birds at 4 days post-challenge. Birds are inoculated with either rLS/ILTV-gB, rLS-GFP, mock inoculation (PBS), or the ILTV vaccine strains CEO or TCO. Ct values for the gC amplicon are compared to Ct values of the endogenous control (collagen amplicon) using the relative $2^{-DeltaDelta}$ method.

Detection of the presence of the challenge virus in the tracheal lumen using the multiplex qPCR protocol described above shows that the chickens vaccinated with the rLS/ILTV-gB shed significant less ILTV (16-fold reduction in ILTV load, P<0.01) than the birds inoculated with rLS-GFP (control group) (see FIG. 5). As expected, the birds vaccinated with the CEO or TCO commercial vaccines also shed significant less ILTV (P<0.01) than the control birds. The level of virus shedding is in accordance with the clinical sign observations.

Detection of the presence of the challenge virus in tears using the multiplex qPCR protocol described above shows that the chickens that received rLS/ILTV-gB shed significant less ILTV, 18-fold reduction in ILTV load (P<0.01), than the birds in control group inoculated with rLS-GFP (see FIG. 5). As expected, the birds vaccinated with the CEO or TCO commercial vaccines also shed significant less ILTV (P<0.01) than the control birds. The level of virus shedding is in accordance with the clinical sign observations.

Figure 6:
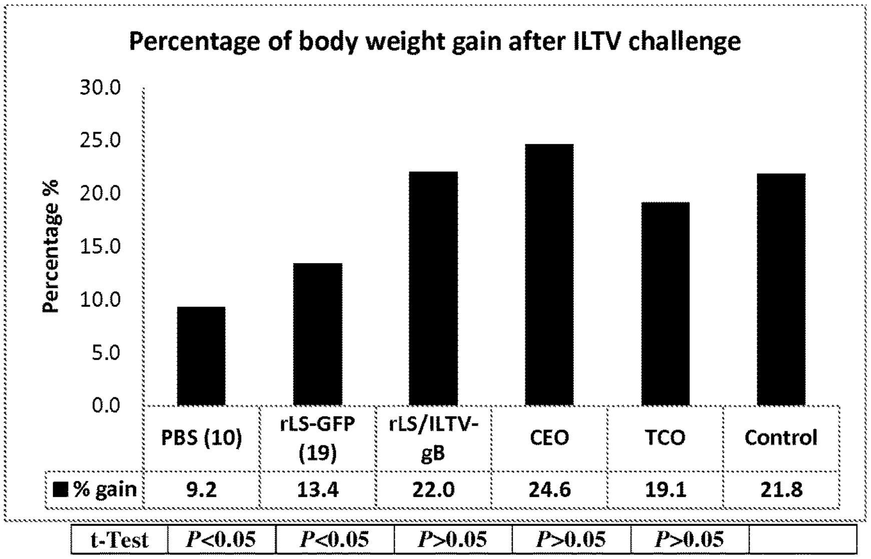
FIG. 6 illustrates that the body-weight gains between inoculated (mock inoculation (PBS), rsLS-GFP, rLS/ILTV-gB, CEO, or TCO) and control birds from age of 42 to 51 days after challenge. The body-weight gain rate of inoculated birds is compared with that of the control (unvaccinated/non-challenged) broilers using the student t-Test. Statistically significant difference occurs when P value is $<0.05$; P value $>0.05$ is not statistically significant.
Figure 7:
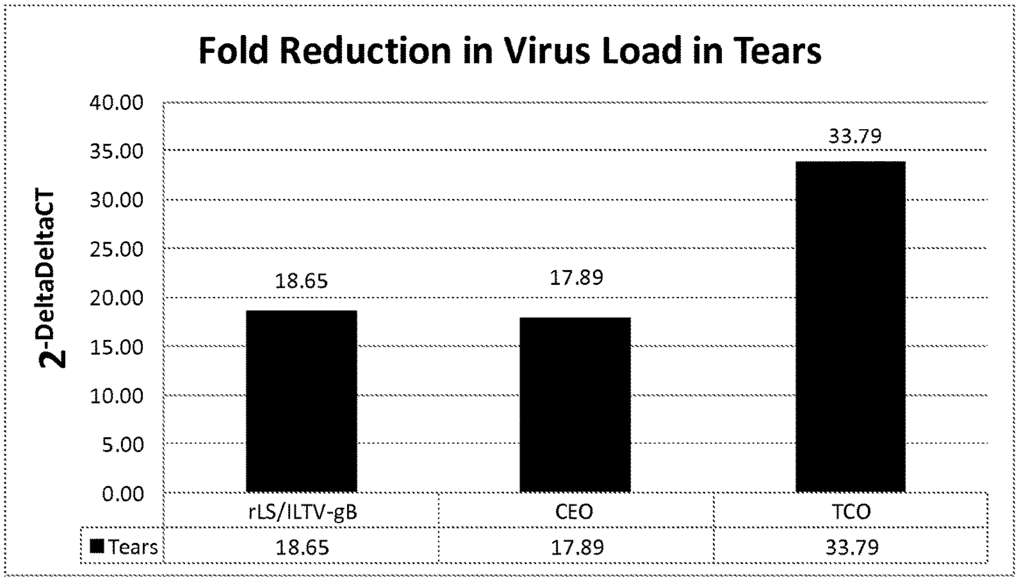
FIG. 7 shows the relative reduction in viral shedding (ILTV) in tears of ILTV-challenged (strain 63140) birds at 4 days post-challenge. Birds are vaccinated with either rLS/ILTV-gB, rLS-GFP, mock inoculation (PBS), or the ILTV vaccine strains CEO or TCO. Ct values for the gC amplicon are compared to Ct values of the endogenous control (collagen amplicon) using the relative $2^{-DeltaDelta}$ method.

In addition to causing the typical clinical signs, ILTV infection of broilers will also decrease body-weight gains. As such, the body-weight of the broilers is measured just prior to being challenged (age of 42 days) and at termination of the experiment (age of 51 days) to evaluate the efficacy of the chimeric vaccine to protecting against disease symptoms. The rate of body-weight gains of the birds from the rLS/ILTV-gB inoculated group is similar to that of the birds from the unvaccinated/unchallenged control and the commercial vaccine groups (CEO and TCO ILTV vaccines) (P>0.05), but significantly higher than that from the PBS and LaSota vector groups (P<0.05). See FIG. 6.

Example 7 Immune Response and Protection Against Virulent NDV Challenge

To evaluate protective efficacy conferred by the chimeric viruses of the present invention against Newcastle disease, forty-one day-old SPF chickens are randomly divided into four groups of 10 birds. Birds in groups 1-4 are inoculated with 100 μl of PBS, the NDV LaSota vaccine, rLS/ILTV-gB ($1.0\times10^7$ $TCID_{50}$/ml), or rLS/ILTV-gD ($1.0\times10^7$ $TCID_{50}$/ml), respectively, via IN/ED routes. At 14 DPV, the birds are challenged with a lethal dose of the NDV/CA02 virus. Serum samples are collected immediately before challenge for anti-NDV antibody detection.

As shown in Table 6, all of the chickens inoculated with the NDV LaSota vaccine or the chimeric viruses are completely protected against NDV challenge without showing any signs of disease. In contrast, all of the birds in the unvaccinated control group (inoculated with PBS) display disease signs with conjunctivitis and severe depression from 2 to 4 DPC and 100% mortality at 5 DPC. The HA inhibition assay of the serum samples collected immediately before the challenge showed that immunization of chickens with either the recombinant chimeric viruses or the parental LaSota vaccine induced NDV-specific serum antibody responses and conferred protection against the virulent NDV challenge.

TABLE 6

| Inoculant | Antibody responses | | Survivors |
|---|---|---|---|
| | Seropositive birds | NDV HA inhibition titer[a] | |
| PBS | 0/10 | 0 | 0/10 |
| NDV LaSota | 10/10 | 4.8 ± 1.4 | 10/10 |
| rLS/ILTV-gB | 10/10 | 3.4 ± 1.3 | 10/10 |
| rLS/ILTV-gD | 10/10 | 3.8 ± 1.2 | 10/10 |

[a]Hemagglutination (HA) inhibition titer is expressed as $\log_2$ of the mean ± standard deviation.

Example 8 Protection Against ILTV of 3-Day-Old Commercial Broiler Chickens Having NDV Maternally Derived Antibodies To determine the efficacy of the recombinant chimeric vaccine in chicks having maternal antibodies to NDV, two groups, each containing fifteen 3-day-old commercial broiler chicks with NDV maternally derived antibody (mean HI titer of 7.1 ($Log_2$)), are vaccinated, via IN/ED routes, with one of the two chimeric vaccines—rLS/ILTV-gB ($1.0\times10^6$ $EID_{50}$/bird) or rLS/ILTV-gD ($1.0\times10^6$ $EID_{50}$/ml). A third group of fifteen chicks receive rLS/GFP vector control as a control, and a fourth group of fifteen chicks are not vaccinated. At 21 days post-vaccination, all groups are challenged with virulent ILTV ($10^4$ $TCID_{50}$/ml per bird). A fifth group of fifteen chicks are used as an unvaccinated and non-challenge control for body-weight gain comparison purposes. Prior to challenge, none of the vaccinated birds display side-effects from the chimeric vaccine. At day 21 post-vaccination (24 days of age), the NDV maternal antibody HI titer declines to 1.00 ($Log_2$), but the HI titers in NDV chimeric vaccine groups slightly increased to 1.53-2.00 ($Log_2$). Birds vaccinated with rLS/ILTV-gB or rLS/ILTV-gD are significantly protected against ILTV challenge with less than 30% of the birds showing mild clinical signs, whereas 100% birds in the rLS/GFP vector control and unvaccinated groups display typical clinical signs or died. There is no significant difference in body weight gains between the vaccinated groups and the non-challenge control group of chickens. At 21 days post-vaccination, tracheal and ocular swabs are collected for a real time qPCR assay using primers listed in Table 3 in order to determine the copy number of the chimeric virus in vaccinated birds. Relative to the control group vaccinated with rLS/GFP, a 51.30% and 42.26% reduction in chimeric virus copy numbers in tracheal swabs for rLS/gB and rLS/gD, respectively, could be demonstrated. Likewise there is a 92.6% and 94.8% reduction in chimeric virus copy numbers in ocular swabs for rLS/gB and rLS/gD, respectively relative to the control group vaccinated with rLS/GFP. While maternally derived NDV antibody moderately suppresses the immunoresponse to the NDV vector, the ILTV antigens expressed from the NDV vector are still sufficient to elicit a significant and protective antibody response in vaccinates and provide protection against ILTV clinical disease.

Example 9 Safety of Recombinant Chimeric Vaccine in 1-Day Old Chicks

Two groups of twenty SPF 1-day old chicks are vaccinated via IN/ED routes, with one of the two chimeric vaccines, either rLS/ILTV-gB ($1.0\times10^7$ $EID_{50}$/bird) or rLS/ILTV-gD ($1.0\times10^7$ $EID_{50}$/bird) at ten times (10×) the recommended dosage. (A standard dose of NDV vaccine strain La Sota is typically given at $1.0\times10^6$ $EID_{50}$/bird (Zoetis, Inc., Florham Park, N.J.)). Two additional groups of twenty SPF 1-day old chicks are vaccinated with either of two commercial NDV vaccines (LaSota strain purchased from Merial (Duluth, Ga.) and Hitchner B1 strain purchased from Zoetis (Florham Park, N.J.). A fifth group of twenty chicks are used as an unvaccinated control. At day 3 and 5 post vaccination, five birds from each group euthanized, and eye eyelid, larynx and trachea of the euthanized birds are collected for examination of histropathology changes and virus replication. The remaining birds in each group are observed for clinical signs for two weeks. None of the birds exhibit clinical signs or vaccine side-effects, even those receiving the higher dosage of the chimeric virus. The chimeric vaccines (rLS/ILTV-gB and rLS/ILTV-gD) given at 10× recommended dosage cause mild lymphocytic inflammation, epithelial proliferation, and minimal to mild deciliation in vaccinated chicken. However, these histopathology changes are similar to the changes observed in chickens vaccinated with the commercial vaccines administered at the lower 1× recommended dosage. Vaccine virus replication is noted in the eyelid, larynx and trachea of vaccinated chickens. In tracheal samples, the titers of the commercial LaSota vaccine and the chimeric vaccines rLS/ILTV-gB and rLS/ILTV-gD are approximately a $\log_{10}$ higher than those in tracheal samples from chickens vaccinated with the commercial NDV Hitchner B1 vaccine. Thus, the chimeric vaccines, rLS/ILTV-gB and rLS/ILTV-gD, are safe to use in day-old SPF chickens and commercial broilers.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

Recitation of ranges of values herein are merely intended to serve as a shorthand method of referring individually to each separate value falling within the range, unless otherwise indicated herein, and each separate value is incorporated into the specification as if it is individually recited herein. For example, if the range 10-15 is disclosed, then 11, 12, 13, and 14 are also disclosed. All numeric values provided herein include a 10% increase and a 10% decrease of that value. So, "ten" includes all numbers between "nine" and "eleven"; "one hundred" includes all numbers between "ninety" and "one-hundred ten". All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. All publications cited in this application are herein incorporated by reference.

We, the inventors, claim:

1. A chimeric virus comprising a Newcastle disease virus (NDV) LaSota strain and a heterologous antigen from infectious laryngotracheitis virus (ILTV), wherein said heterologous antigen is gB and wherein said chimeric virus has a cDNA sequence of SEQ ID NO: 14.

2. The chimeric virus of claim 1, wherein said chimeric virus contains a negative-strand RNA having the RNA sequence of SEQ ID NO: 15.

3. A chimeric virus comprising a Newcastle disease virus (NDV) LaSota strain and a heterologous antigen from infectious laryngotracheitis virus (ILTV), wherein said heterologous antigen is gD and wherein said chimeric virus has a cDNA sequence of SEQ ID NO: 17.

4. The chimeric virus of claim 3, wherein said chimeric virus contains a negative-strand RNA having the RNA sequence of SEQ ID NO: 18.

5. An immunogenic composition comprising the chimeric virus of claim 1, one or more diluents, optionally an adjuvant, and optionally a carrier.

6. A method of generating an immune response to NDV and ILTV in an avian animal comprising administering an immunogenic effective amount of the immunogenic composition of claim 5 to said avian animal.

7. A method of preventing ILTV disease and NDV disease in an avian animal comprising administering an immunogenic effective amount of the immunogenic composition of claim 5 to said avian animal in need thereof.

8. A method of reducing shedding of ILTV and NDV by an avian animal capable of being infected with ILTV and/or NDV comprising administering an immunogenic effective amount of the immunogenic composition of claim 5 to said avian animal.

9. A novel, purified expression vector comprising a polynucleotide sequence selected from the group consisting of SEQ ID NO: 13, and SEQ ID NO: 16.

10. An immunogenic composition comprising the chimeric virus of claim 3, one or more diluents, optionally an adjuvant, and optionally a carrier.

11. A method of generating an immune response to NDV and ILTV in an avian animal comprising administering an immunogenic effective amount of the immunogenic composition of claim 10 to said avian animal.

12. A method of preventing ILTV disease and NDV disease in an avian animal comprising administering an immunogenic effective amount of the immunogenic composition of claim 10 to said avian animal in need thereof.

13. A method of reducing shedding of ILTV and NDV by an avian animal capable of being infected with ILTV and/or NDV comprising administering an immunogenic effective amount of the immunogenic composition of claim 10 to said avian animal.

* * * * *

```
                          SEQUENCE LISTING

<160> NUMBER OF SEQ ID NOS: 26

<210> SEQ ID NO 1
<211> LENGTH: 2649
<212> TYPE: DNA
<213> ORGANISM: Infectious laryngotracheitis virus (ILTV)

<400> SEQUENCE: 1

atgcaatcct acatcgccgt gaacattgac atggctagct tgaaaatgct gatctgcgtg      60

tgcgtggcaa tcctgatccc atctacccta tctcaagatt cacacggaat tgctggaata     120

atagaccctc gtgatacagc cagcatggat gttggaaaaa tctctttctc cgaagccatt     180

gggtcggggg caccgaaaga accccagatt agaaacagaa tttttgcgtg ctcatctcca     240

actggcgcca gtgttgcgag gcttgcccag ccacgacatt gtcaccgaca tgccgattcg     300

actaacatga ctgaaggaat tgccgtagtc ttcaagcaaa acattgcccc gtacgtcttt     360

aatgtgactc tatactataa acatataacc acagttacta cgtgggcatt attctcaaga     420

ccccaaataa caaatgagta cgtgaccagg gttccaatag actatcatga aattgtcagg     480

attgatcgat cgggagaatg ctcatccaaa gcaacgtatc ataaaaattt catgtttttt     540

gaagcttacg acaatgatga agcagaaaaa aaattgcccc tggttccatc actgttaaga     600

tcaactgtct ccaaggcgtt tcatacaact aactttacta agcgacatca aaccctggga     660

taccgaacgt ctacatcggt cgactgtgtt gtggaatatc tacaggctag atctgtatac     720

ccgtatgatt actttggaat ggcgacaggt gatacagtag aaatttctcc tttttatacc     780

aaaaacacga ccggaccaag gcgtcacagt gtctacagag actatagatt tctcgaaatc     840

gcaaattatc aagtcaggga tttggaaacc ggacaaataa gaccccctaa aaaaagaaac     900

tttctaacag atgaacaatt cactataggc tgggatgcaa tggaagaaaa ggaatctgta     960

tgtactctca gtaaatggat tgaagtcccg gaagcagttc gtgtttcgta caaaaacagt    1020

taccactttt cacttaaaga tatgactatg acgttctcgt ccggaaaaca acctttaac     1080

atcagcaggc ttcatttggc tgaatgcgtt cctaccatag cctcggaggc catagatggc    1140

atctttgcca gaaagtatag ttcgactcat gtccgttctg gggacatcga atactatctc    1200

ggtagtggcg gatttctgat cgcatttcag aaactcatga gccatggctt ggctgaaatg    1260

tacctagaag aggcacaaag acaaaatcat ctcccgagag ggagagagcg tcgccaagcc    1320

gcaggtcgcc gcacggcgtc gctgcagtct ggacctcagg gtgatagaat tactacccac    1380

agttctgcaa catttgccat gttacaattt gcatacgaca aaatccaagc ccatgttaac    1440

gagcttatcg gaaatttgtt ggaagcgtgg tgtgagcttc agaaccgcca actgattgta    1500

tggcatgaga tgaagaaact aaacccgaac tcactgatga catctttgtt cggacaacct    1560

gtaagcgcca ggctattggg agacatcgta gcggtatcaa aatgtataga aattccaatc    1620

gaaaatatta ggatgcagga ttccatgcgc atgccagggg acccaaccat gtgctatacc    1680

agaccagtac ttattttcag gtattcgtcc tcccctgagt cacagttttc tgcgaactca    1740
```

-continued

```
acagaaaacc acaatcttga catattaggc caactcggag aacataatga aattttacaa   1800
gggcggaatt tgatagaacc atgcatgatc aatcacagac ggtactttct gttgggagaa   1860
aactaccttc tttacgaaga ctatacattt gttagacaag taaatgcttc cgagatcgaa   1920
gaagtgagca cattcatcaa cttgaacgcc actatactag aagatttgga ctttgtgccc   1980
gtcgaagtat acactcgcga ggaactcaga gatactggga ctttaaacta tgatgatgtg   2040
gtcagatatc aaaatattta taacaaaagg ttcagagaca ttgacactgt aatacgtgga   2100
gataggggag atgcaatctt tagagcaata gcagattttt ttggcaacac tcttggagaa   2160
gtaggaaagg cattgggaac tgtagtgatg acagccgcgg cagcagtaat ttctacagta   2220
tctggcatcg cctcatttct ttctaacccg ttcgccgcac tcggaattgg gatagcggtg   2280
gtggtgagca ttattttagg actgctggcg ttcaaatatg taatgaacct gaaatcaaac   2340
ccagttcagg ttctgttccc aggcgcagtt cccccggccg gaactcctcc acgaccctct   2400
agacgttact acaaggatga ggaggttgag gaggatagtg atgaggacga caggatactt   2460
gccaccagag ttctgaaagg ccttgagctt ctacacaagg atgaacagaa agctcgaaga   2520
cagaaagcgc ggttttctgc ttttgctaaa aatatgagaa acctatttcg cagaaaaccc   2580
cgaaccaagg aagatgacta ccccctgctc gaatacccct cgtgggcaga agaaagcgaa   2640
gacgaataa                                                           2649
```

<210> SEQ ID NO 2
<211> LENGTH: 882
<212> TYPE: PRT
<213> ORGANISM: Infectious laryngotracheitis virus (ILTV)

<400> SEQUENCE: 2

```
Met Gln Ser Tyr Ile Ala Val Asn Ile Asp Met Ala Ser Leu Lys Met
1               5                   10                  15

Leu Ile Cys Val Cys Val Ala Ile Leu Ile Pro Ser Thr Leu Ser Gln
            20                  25                  30

Asp Ser His Gly Ile Ala Gly Ile Ile Asp Pro Arg Asp Thr Ala Ser
        35                  40                  45

Met Asp Val Gly Lys Ile Ser Phe Ser Glu Ala Ile Gly Ser Gly Ala
    50                  55                  60

Pro Lys Glu Pro Gln Ile Arg Asn Arg Ile Phe Ala Cys Ser Ser Pro
65                  70                  75                  80

Thr Gly Ala Ser Val Ala Arg Leu Ala Gln Pro Arg His Cys His Arg
                85                  90                  95

His Ala Asp Ser Thr Asn Met Thr Glu Gly Ile Ala Val Val Phe Lys
            100                 105                 110

Gln Asn Ile Ala Pro Tyr Val Phe Asn Val Thr Leu Tyr Tyr Lys His
        115                 120                 125

Ile Thr Thr Val Thr Thr Trp Ala Leu Phe Ser Arg Pro Gln Ile Thr
    130                 135                 140

Asn Glu Tyr Val Thr Arg Val Pro Ile Asp Tyr His Glu Ile Val Arg
145                 150                 155                 160

Ile Asp Arg Ser Gly Glu Cys Ser Ser Lys Ala Thr Tyr His Lys Asn
                165                 170                 175

Phe Met Phe Phe Glu Ala Tyr Asp Asn Asp Glu Ala Glu Lys Lys Leu
            180                 185                 190

Pro Leu Val Pro Ser Leu Leu Arg Ser Thr Val Ser Lys Ala Phe His
        195                 200                 205
```

-continued

```
Thr Thr Asn Phe Thr Lys Arg His Gln Thr Leu Gly Tyr Arg Thr Ser
    210                 215                 220

Thr Ser Val Asp Cys Val Val Glu Tyr Leu Gln Ala Arg Ser Val Tyr
225                 230                 235                 240

Pro Tyr Asp Tyr Phe Gly Met Ala Thr Gly Asp Thr Val Glu Ile Ser
                245                 250                 255

Pro Phe Tyr Thr Lys Asn Thr Thr Gly Pro Arg Arg His Ser Val Tyr
            260                 265                 270

Arg Asp Tyr Arg Phe Leu Glu Ile Ala Asn Tyr Gln Val Arg Asp Leu
        275                 280                 285

Glu Thr Gly Gln Ile Arg Pro Pro Lys Lys Arg Asn Phe Leu Thr Asp
    290                 295                 300

Glu Gln Phe Thr Ile Gly Trp Asp Ala Met Glu Glu Lys Glu Ser Val
305                 310                 315                 320

Cys Thr Leu Ser Lys Trp Ile Glu Val Pro Glu Ala Val Arg Val Ser
                325                 330                 335

Tyr Lys Asn Ser Tyr His Phe Ser Leu Lys Asp Met Thr Met Thr Phe
            340                 345                 350

Ser Ser Gly Lys Gln Pro Phe Asn Ile Ser Arg Leu His Leu Ala Glu
        355                 360                 365

Cys Val Pro Thr Ile Ala Ser Glu Ala Ile Asp Gly Ile Phe Ala Arg
    370                 375                 380

Lys Tyr Ser Ser Thr His Val Arg Ser Gly Asp Ile Glu Tyr Tyr Leu
385                 390                 395                 400

Gly Ser Gly Gly Phe Leu Ile Ala Phe Gln Lys Leu Met Ser His Gly
                405                 410                 415

Leu Ala Glu Met Tyr Leu Glu Glu Ala Gln Arg Gln Asn His Leu Pro
            420                 425                 430

Arg Gly Arg Glu Arg Arg Gln Ala Ala Gly Arg Arg Thr Ala Ser Leu
        435                 440                 445

Gln Ser Gly Pro Gln Gly Asp Arg Ile Thr Thr His Ser Ser Ala Thr
    450                 455                 460

Phe Ala Met Leu Gln Phe Ala Tyr Asp Lys Ile Gln Ala His Val Asn
465                 470                 475                 480

Glu Leu Ile Gly Asn Leu Leu Glu Ala Trp Cys Glu Leu Gln Asn Arg
                485                 490                 495

Gln Leu Ile Val Trp His Glu Met Lys Lys Leu Asn Pro Asn Ser Leu
            500                 505                 510

Met Thr Ser Leu Phe Gly Gln Pro Val Ser Ala Arg Leu Leu Gly Asp
        515                 520                 525

Ile Val Ala Val Ser Lys Cys Ile Glu Ile Pro Ile Glu Asn Ile Arg
    530                 535                 540

Met Gln Asp Ser Met Arg Met Pro Gly Asp Pro Thr Met Cys Tyr Thr
545                 550                 555                 560

Arg Pro Val Leu Ile Phe Arg Tyr Ser Ser Ser Pro Glu Ser Gln Phe
                565                 570                 575

Ser Ala Asn Ser Thr Glu Asn His Asn Leu Asp Ile Leu Gly Gln Leu
            580                 585                 590

Gly Glu His Asn Glu Ile Leu Gln Gly Arg Asn Leu Ile Glu Pro Cys
        595                 600                 605

Met Ile Asn His Arg Arg Tyr Phe Leu Leu Gly Glu Asn Tyr Leu Leu
    610                 615                 620
```

-continued

```
Tyr Glu Asp Tyr Thr Phe Val Arg Gln Val Asn Ala Ser Glu Ile Glu
625                 630                 635                 640

Glu Val Ser Thr Phe Ile Asn Leu Asn Ala Thr Ile Leu Glu Asp Leu
                645                 650                 655

Asp Phe Val Pro Val Glu Val Tyr Thr Arg Glu Glu Leu Arg Asp Thr
            660                 665                 670

Gly Thr Leu Asn Tyr Asp Asp Val Val Arg Tyr Gln Asn Ile Tyr Asn
        675                 680                 685

Lys Arg Phe Arg Asp Ile Asp Thr Val Ile Arg Gly Asp Arg Gly Asp
    690                 695                 700

Ala Ile Phe Arg Ala Ile Ala Asp Phe Phe Gly Asn Thr Leu Gly Glu
705                 710                 715                 720

Val Gly Lys Ala Leu Gly Thr Val Val Met Thr Ala Ala Ala Ala Val
                725                 730                 735

Ile Ser Thr Val Ser Gly Ile Ala Ser Phe Leu Ser Asn Pro Phe Ala
            740                 745                 750

Ala Leu Gly Ile Gly Ile Ala Val Val Val Ser Ile Ile Leu Gly Leu
        755                 760                 765

Leu Ala Phe Lys Tyr Val Met Asn Leu Lys Ser Asn Pro Val Gln Val
    770                 775                 780

Leu Phe Pro Gly Ala Val Pro Pro Ala Gly Thr Pro Pro Arg Pro Ser
785                 790                 795                 800

Arg Arg Tyr Tyr Lys Asp Glu Glu Val Glu Glu Asp Ser Asp Glu Asp
                805                 810                 815

Asp Arg Ile Leu Ala Thr Arg Val Leu Lys Gly Leu Glu Leu Leu His
            820                 825                 830

Lys Asp Glu Gln Lys Ala Arg Arg Gln Lys Ala Arg Phe Ser Ala Phe
        835                 840                 845

Ala Lys Asn Met Arg Asn Leu Phe Arg Arg Lys Pro Arg Thr Lys Glu
    850                 855                 860

Asp Asp Tyr Pro Leu Leu Glu Tyr Pro Ser Trp Ala Glu Glu Ser Glu
865                 870                 875                 880

Asp Glu


<210> SEQ ID NO 3
<211> LENGTH: 1305
<212> TYPE: DNA
<213> ORGANISM: Infectious laryngotracheitis virus (ILTV)

<400> SEQUENCE: 3

atgcaccgtc ctcatctcag acggcactcg cgttactacg cgaaaggaga ggtgcttaac     60

aaacacatgg attgcggtgg aaaacggtgc tgctcaggcg cagctgtatt cactcttttc    120

tggacttgtg tcaggattat gcgggagcat atctgctttg tacgcaacgc tatggaccgc    180

catttatttt tgaggaatgc tttttggact atcgtactgc tttcttcctt cgctagccag    240

agcaccgccg ccgtcacgta cgactacatt ttaggccgtc gcgcgctcga cgcgctaacc    300

ataccggcgg ttggcccgta taacagatac ctcactaggg tatcaagagg ctgcgacgtt    360

gtcgagctca acccgatttc taacgtggac gacatgatat cggcggccaa agaaaaagag    420

aagggggggcc ctttcgaggc ctccgtcgtc tggttctacg tgattaaggg cgacgacggc    480

gaggacaagt actgtccaat ctatagaaaa gagtacaggg aatgtggcga cgtacaactg    540

ctatctgaat gcgccgttca atctgcacag atgtgggcag tggactatgt tcctagcacc    600

cttgtatcgc gaaatggcgc gggactgact atattctccc ccactgctgc gctctctggc    660
```

```
caatacttgc tgaccctgaa aatcgggaga tttgcgcaaa cagctctcgt aactctagaa    720

gttaacgatc gctgtttaaa gatcgggtcg cagcttaact ttttaccgtc gaaatgctgg    780

acaacagaac agtatcagac tggatttcaa ggcgaacacc tttatccgat cgcagacacc    840

aatacacgac acgcggacga cgtatatcgg ggatacgaag atattctgca gcgctggaat    900

aatttgctga ggaaaaagaa tcctagcgcg ccagaccctc gtccagatag cgtcccgcaa    960

gaaattcccg ctgtaaccaa gaaagcggaa gggcgcaccc cggacgcaga aagcagcgaa   1020

aagaaggccc ctccagaaga ctcggaggac gacatgcagg cagaggcttc tggagaaaat   1080

cctgccgccc tccccgaaga cgacgaagtc cccgaggaca ccgagcacga tgatccaaac   1140

tcggatcctg actattacaa tgatatgccc gccgtgatcc cggtggagga gactactaaa   1200

agttctaatg ccgtctccat gcccatattc gcggcgttcg tagcctgcgc ggtcgcgctc   1260

gtggggctac tggtttggag catcgtaaaa tgcgcgcgta gctaa                   1305


<210> SEQ ID NO 4
<211> LENGTH: 434
<212> TYPE: PRT
<213> ORGANISM: Infectious laryngotracheitis virus (ILTV)

<400> SEQUENCE: 4

Met His Arg Pro His Leu Arg Arg His Ser Arg Tyr Tyr Ala Lys Gly
1               5                   10                  15

Glu Val Leu Asn Lys His Met Asp Cys Gly Gly Lys Arg Cys Cys Ser
            20                  25                  30

Gly Ala Ala Val Phe Thr Leu Phe Trp Thr Cys Val Arg Ile Met Arg
        35                  40                  45

Glu His Ile Cys Phe Val Arg Asn Ala Met Asp Arg His Leu Phe Leu
    50                  55                  60

Arg Asn Ala Phe Trp Thr Ile Val Leu Leu Ser Ser Phe Ala Ser Gln
65                  70                  75                  80

Ser Thr Ala Ala Val Thr Tyr Asp Tyr Ile Leu Gly Arg Arg Ala Leu
                85                  90                  95

Asp Ala Leu Thr Ile Pro Ala Val Gly Pro Tyr Asn Arg Tyr Leu Thr
            100                 105                 110

Arg Val Ser Arg Gly Cys Asp Val Val Glu Leu Asn Pro Ile Ser Asn
        115                 120                 125

Val Asp Asp Met Ile Ser Ala Ala Lys Glu Lys Glu Lys Gly Gly Pro
    130                 135                 140

Phe Glu Ala Ser Val Val Trp Phe Tyr Val Ile Lys Gly Asp Asp Gly
145                 150                 155                 160

Glu Asp Lys Tyr Cys Pro Ile Tyr Arg Lys Glu Tyr Arg Glu Cys Gly
                165                 170                 175

Asp Val Gln Leu Leu Ser Glu Cys Ala Val Gln Ser Ala Gln Met Trp
            180                 185                 190

Ala Val Asp Tyr Val Pro Ser Thr Leu Val Ser Arg Asn Gly Ala Gly
        195                 200                 205

Leu Thr Ile Phe Ser Pro Thr Ala Ala Leu Ser Gly Gln Tyr Leu Leu
    210                 215                 220

Thr Leu Lys Ile Gly Arg Phe Ala Gln Thr Ala Leu Val Thr Leu Glu
225                 230                 235                 240

Val Asn Asp Arg Cys Leu Lys Ile Gly Ser Gln Leu Asn Phe Leu Pro
                245                 250                 255
```

```
Ser Lys Cys Trp Thr Thr Glu Gln Tyr Gln Thr Gly Phe Gln Gly Glu
            260                 265                 270

His Leu Tyr Pro Ile Ala Asp Thr Asn Thr Arg His Ala Asp Asp Val
        275                 280                 285

Tyr Arg Gly Tyr Glu Asp Ile Leu Gln Arg Trp Asn Asn Leu Leu Arg
    290                 295                 300

Lys Lys Asn Pro Ser Ala Pro Asp Pro Arg Pro Asp Ser Val Pro Gln
305                 310                 315                 320

Glu Ile Pro Ala Val Thr Lys Lys Ala Glu Gly Arg Thr Pro Asp Ala
                325                 330                 335

Glu Ser Ser Glu Lys Lys Ala Pro Pro Glu Asp Ser Glu Asp Asp Met
            340                 345                 350

Gln Ala Glu Ala Ser Gly Glu Asn Pro Ala Ala Leu Pro Glu Asp Asp
        355                 360                 365

Glu Val Pro Glu Asp Thr Glu His Asp Asp Pro Asn Ser Asp Pro Asp
    370                 375                 380

Tyr Tyr Asn Asp Met Pro Ala Val Ile Pro Val Glu Glu Thr Thr Lys
385                 390                 395                 400

Ser Ser Asn Ala Val Ser Met Pro Ile Phe Ala Ala Phe Val Ala Cys
                405                 410                 415

Ala Val Ala Leu Val Gly Leu Leu Val Trp Ser Ile Val Lys Cys Ala
            420                 425                 430

Arg Ser


<210> SEQ ID NO 5
<211> LENGTH: 25
<212> TYPE: DNA
<213> ORGANISM: Newcastle disease virus

<400> SEQUENCE: 5

ggtggctaca actatcaact aaact                                            25


<210> SEQ ID NO 6
<211> LENGTH: 24
<212> TYPE: DNA
<213> ORGANISM: Newcastle disease virus

<400> SEQUENCE: 6

gtgtgtaact accgtgtact aagc                                             24


<210> SEQ ID NO 7
<211> LENGTH: 31
<212> TYPE: DNA
<213> ORGANISM: Artificial Sequence
<220> FEATURE:
<223> OTHER INFORMATION: Primer

<400> SEQUENCE: 7

atagttgtag ccaccatgca atcctacatc g                                     31


<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8

gtagttacac acagcttatt cgtcttcgct ttc                                   33
```

-continued

<210> SEQ ID NO 9
<211> LENGTH: 31
<212> TYPE: DNA
<213> ORGANISM: Artificial Sequence
<220> FEATURE:
<223> OTHER INFORMATION: Primer

<400> SEQUENCE: 9
atagttgtag ccaccatgca ccgtcctcat c 31

<210> SEQ ID NO 10
<211> LENGTH: 31
<212> TYPE: DNA
<213> ORGANISM: Artificial Sequence
<220> FEATURE:
<223> OTHER INFORMATION: Primer

<400> SEQUENCE: 10
gtagttacac acagcttagc tacgcgcgca t 31

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
atagttgtag ccaccatggt gagcaagcag atc 33

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
acggtagtta cacactcaca cccactcgtg cag 33

<210> SEQ ID NO 13
<211> LENGTH: 21176
<212> TYPE: DNA
<213> ORGANISM: Artificial Sequence
<220> FEATURE:
<223> OTHER INFORMATION: Plasmid

<400> SEQUENCE: 13
ggcgccggct gggcaacatt ccgaggggac cgtcccctcg gtaatggcga atgggacgcg 60
gccgatccgg ctgctaacaa agcccgaaag gaagctgagt tggctgctgc caccgctgag 120
caataactag cataacccct tggggcctct aaacgggtct tgaggggttt tttgctgaaa 180
ggaggaacta tatccggatc ggccgatccg gctgctaaca aagcccgaaa ggaagctgag 240
ttggctgctg ccaccgctga gcaataacta gcataacccc ttggggcctc taaacgggtc 300
ttgaggggtt ttttgctgaa aggaggaact atatccggat ggccgccacc ggtgggcctt 360
gcagcacatc ccccttcgc cagctggcgt aatagcgaag aggcccgcac cgatcgccct 420
tcccaacagt tgcgtagcct gaatggcgaa tgggacgcgc cctgtagcgg cgcattaagc 480
gcggcgggtg tggtggttac gcgcagcgtg accgctacac ttgccagcgc cctagcgccc 540
gctcctttcg ctttcttccc ttcctttctc gccacgttcg ccggctttcc ccgtcaagct 600
ctaaatcggg ggctcccttt agggttccga tttagtgctt tacggcacct cgaccccaaa 660

-continued

```
aaacttgatt agggtgatgg ttcacgtagt gggccatcgc cctgatagac ggtttttcgc    720
cctttgacgt tggagtccac gttctttaat agtggactct tgttccaaac tggaacaaca    780
ctcaacccta tctcggtcta ttcttttgat ttataaggga ttttgccgat ttcggcctat    840
tggttaaaaa atgagctgat ttaacaaaaa tttaacgcga attttaacaa aatattaacg    900
tttacaattt caggtggcac ttttcgggga aatgtgcgcg gaacccctat ttgtttattt    960
ttctaaatac attcaaatat gtatccgctc atgagacaat aaccctgata aatgcttcaa   1020
taatattgaa aaaggaagag tatgagtatt caacatttcc gtgtcgccct tattcccttt   1080
tttgcggcat tttgccttcc tgtttttgct cacccagaaa cgctggtgaa agtaaaagat   1140
gctgaagatc agttgggtgc acgagtgggt tacatcgaac tggatctcaa cagcggtaag   1200
atccttgaga gttttcgccc cgaagaacgt tttccaatga tgagcacttt taaagttctg   1260
ctatgtggcg cggtattatc ccgtattgac gccgggcaag agcaactcgg tcgccgcata   1320
cactattctc agaatgactt ggttgagtac tcaccagtca cagaaaagca tcttacggat   1380
ggcatgacag taagagaatt atgcagtgct gccataagca tgagtgataa cactgcggcc   1440
aacttacttc tgacaacgat cggaggaccg aaggagctaa ccgctttttt tcacaacatg   1500
ggggatcatg taactcgcct tgatcgttgg gaaccggagc tgaatgaagc cataccaaac   1560
gacgagcgtg acaccacgat gcctgtagca atggcaacaa cgttgcgcaa actattaact   1620
ggcgaactac ttactctagc ttcccggcaa caattaatag actggatgga ggcggataaa   1680
gttgcaggac cacttctgcg ctcggccctt ccggctggct ggtttattgc tgataaatct   1740
ggagccggtg agcgtgggtc tcgcggtatc attgcagcac tggggccaga tggtaagccc   1800
tcccgtatcg tagttatcta cacgacgggc agtcaggcaa ctatggatga acgaaataga   1860
cagatcgctg agataggtgc ctcactgatt aagcattggt aactgtcaga ccaagtttac   1920
tcatatatac tttagattga tttaaaactt catttttaat ttaaaaggat ctaggtgaag   1980
atcctttttg ataatctcat gaccaaaatc ccttaacgtg agttttcgtt ccactgagcg   2040
tcagaccccg tagaaaagat caaaggatct tcttgagatc ctttttttct gcgcgtaatc   2100
tgctgcttgc aaacaaaaaa accaccgcta ccagcggtgg tttgtttgcc ggatcaagag   2160
ctaccaactc tttttccgaa ggtaactggc ttcagcagag cgcagatacc aaatactgtc   2220
cttctagtgt agccgtagtt aggccaccac ttcaagaact ctgtagcacc gcctacatac   2280
ctcgctctgc taatcctgtt accagtggct gctgccagtg gcgataagtc gtgtcttacc   2340
gggttggact caagacgata gttaccggat aaggcgcagc ggtcgggctg aacggggggt   2400
tcgtgcacac agcccagctt ggagcgaacg acctacaccg aactgagata cctacagcgt   2460
gagcattgag aaagcgccac gcttcccgaa gggagaaagg cggacaggta tccggtaagc   2520
ggcagggtcg gaacaggaga gcgcacgagg gagcttccag ggggaaacgc ctggtatctt   2580
tatagtcctg tcgggtttcg ccacctctga cttgagcgtc gatttttgtg atgctcgtca   2640
ggggggccga gcctatggaa aaacgccagc aacgcggcct ttttacggtt cctggccttt   2700
tgctggcctt ttgctcacat gttctttcct gcgttatccc ctgattctgt ggataaccgt   2760
attaccgcct ttgagtgagc tgataccgct cgccgcagcc gaacgaccga gcgcagcgag   2820
tcagtgagcg aggaagcgga agagcgccca atacgcaaac cgcctctccc cgcgcgttgg   2880
ccgattcatt aatgcagctg gcacgacagg tttcccgact ggaaagcggg cagtgagcgc   2940
aacgcaatta atgtgagtta cctcactcat taggcacccc aggctttaca ctttatgctt   3000
```

ccggctccta tgttgtgtgg aattgtgagc ggataacaat ttcacacagg aaacagctat 3060
gaccatgatt acgccaagct cggaagcggc cgctaatacg actcactata gggaccaaac 3120
agagaatccg tgagtcgcga taaaaggcga aagagcaatt gaagtcacac gggtagaagg 3180
tgtgaatctc gagtgcgagc ccgaagcaca aactcgagaa agccttctgc caacatgtct 3240
tccgtatttg atgagtacga acagctcctc gcggctcaga ctcgccccaa tggagctcat 3300
ggagggggag aaaaagggag taccttaaaa gtagacgtcc cggtattcac tcttaacagt 3360
gatgacccag aagatagatg gagctttgtg gtattctgcc tccggattgc tgttagcgaa 3420
gatgccaaca aaccactcag gcaaggtgct ctcatatctc ttttatgctc ccactcacag 3480
gtaatgagga accatgttgc ccttgcaggg aaacagaatg aagccacatt ggccgtgctt 3540
gagattgatg gctttgccaa cggcacgccc cagttcaaca ataggagtgg agtgtctgaa 3600
gagagagcac agagatttgc gatgatagca ggatctctcc ctcgggcatg cagcaacgga 3660
accccgttcg tcacagccgg ggccgaagat gatgcaccag aagacatcac cgataccctg 3720
gagaggatcc tctctatcca ggctcaagta tgggtcacag tagcaaaagc catgactgcg 3780
tatgagactg cagatgagtc ggaaacaagg cgaatcaata agtatatgca gcaaggcagg 3840
gtccaaaaga aatacatcct ctaccccgta tgcaggagca caatccaact cacgatcaga 3900
cagtctcttg cagtccgcat ctttttggtt agcgagctca agagaggccg caacacggca 3960
ggtggtacct ctacttatta taacctggta ggggacgtag actcatacat caggaatacc 4020
gggcttactg cattcttctt gacactcaag tacggaatca acaccaagac atcagccctt 4080
gcacttagta gcctctcagg cgacatccag aagatgaagc agctcatgcg tttgtatcgg 4140
atgaaaggag ataatgcgcc gtacatgaca ttacttggtg atagtgacca gatgagcttt 4200
gcgcctgccg agtatgcaca actttactcc tttgccatgg gtatggcatc agtcctagat 4260
aaaggtactg ggaaatacca atttgccagg gactttatga gcacatcatt ctggagactt 4320
ggagtagagt acgctcaggc tcagggaagt agcattaacg aggatatggc tgccgagcta 4380
aagctaaccc cagcagcaag gaggggcctg gcagctgctg cccaacgggt ctccgaggag 4440
accagcagca tagacatgcc tactcaacaa gtcggagtcc tcactgggct tagcgagggg 4500
gggtcccaag ctctacaagg cggatcgaat agatcgcaag ggcaaccaga agccggggat 4560
ggggagaccc aattcctgga tctgatgaga gcggtagcaa atagcatgag ggaggcgcca 4620
aactctgcac agggcactcc ccaatcgggg cctcccccaa ctcctgggcc atcccaagat 4680
aacgacaccg actgggggta ttgatggaca aaacccagcc tgcttccaca aaaacatccc 4740
aatgccctca cccgtagtcg acccctcgat ttgcggctct atatgaccac accctcaaac 4800
aaacatcccc ctctttcctc cctccccctg ctgtacaact ccgcacgccc tagataccac 4860
aggcacaatg cggctcacta acaatcaaaa cagagccgag ggaattagaa aaaagtacgg 4920
gtagaagagg gatattcaga gatcagggca agtctcccga gtctctgctc tctcctctac 4980
ctgatagacc aggacaaaca tggccacctt tacagatgca gagatcgacg agctatttga 5040
gacaagtgga actgtcattg acaacataat tacagcccag ggtaaaccag cagagactgt 5100
tggaaggagt gcaatcccac aaggcaagac caaggtgctg agcgcagcat gggagaagca 5160
tgggagcatc cagccaccgg ccagtcaagg caaccccgat cgacaggaca gatctgacaa 5220
acaaccatcc acacccgggc aaacgacccc gcatgacagc ccgccggcca catccgccga 5280
ccagcccccc acccaggcca cagacgaagc cgtcgacaca cagctcagga ccggagcaag 5340
caactctctg ctgttgatgc ttgacaagct cagcaataaa tcgtccaatg ctaaaaaggg 5400

-continued

```
cccatggtcg agcccccaag aggggaatca ccaacgtccg actcaacagc aggggagtca   5460
acccagtcgc ggaaacagtc aggaaagacc gcagaaccaa gtcaaggccg cccctggaaa   5520
ccagggcaca gacgtgaaca cagcatatca tggacaatgg gaggagtcac aactatcagc   5580
tggtgcaacc cctcatgctc tccgatcaag gcagagccaa gacaataccc ttgtatctgc   5640
ggatcatgtc cagccacctg tagactttgt gcaagcgatg atgtctatga tggaggcgat   5700
atcacagaga gtaagtaagg tcgactatca gctagatctt gtcttgaaac agacatcctc   5760
catccctatg atgcggtccg aaatccaaca gctgaaaaca tctgttgcag tcatggaagc   5820
caacttggga atgatgaaga ttctggatcc cggttgtgcc aacatttcat ctctgagtga   5880
tctacgggca gttgcccgat ctcacccggt tttagtttca ggccctggag acccctctcc   5940
ctatgtgaca caaggaggcg aaatggcact taataaactt tcgcaaccag tgccacatcc   6000
atctgaattg attaaacccg ccactgcatg cgggcctgat ataggagtgg aaaaggacac   6060
tgtccgtgca ttgatcatgt cacgcccaat gcacccgagt tcttcagcca agctcctaag   6120
caagttagat gcagccgggt cgatcgagga aatcaggaaa atcaagcgcc ttgctctaaa   6180
tggctaatta ctactgccac acgtagcggg tccctgtcca ctcggcatca cacggaatct   6240
gcaccgagtt ccccccgca gacccaaggt ccaactctcc aagcggcaat cctctctcgc   6300
ttcttcagcc ccactgaatg atcgcgtaac cgtaattaat ctagctacat taaggattaa   6360
gaaaaaatac gggtagaatt ggagtgcccc aattgtgagt ttagttgata gttgtagcca   6420
ccatgcaatc ctacatcgcc gtgaacattg acatggctag cttgaaaatg ctgatctgcg   6480
tgtgcgtggc aatcctgatc ccatctaccc tatctcaaga ttcacacgga attgctggaa   6540
taatagaccc tcgtgataca gccagcatgg atgttggaaa aatctctttc tccgaagcca   6600
ttgggtcggg ggcaccgaaa gaaccccaga ttagaaacag aatttttgcg tgctcatctc   6660
caactggcgc cagtgttgcg aggcttgccc agccacgaca ttgtcaccga catgccgatt   6720
cgactaacat gactgaagga attgccgtag tcttcaagca aaacattgcc ccgtacgtct   6780
ttaatgtgac tctatactat aaacatataa ccacagttac tacgtgggca ttattctcaa   6840
gaccccaaat aacaaatgag tacgtgacca gggttccaat agactatcat gaaattgtca   6900
ggattgatcg atcgggagaa tgctcatcca aagcaacgta tcataaaaat ttcatgtttt   6960
ttgaagctta cgacaatgat gaagcagaaa aaaaattgcc cctggttcca tcactgttaa   7020
gatcaactgt ctccaaggcg tttcatacaa ctaactttac taagcgacat caaaccctgg   7080
gataccgaac gtctacatcg gtcgactgtg ttgtggaata tctacaggct agatctgtat   7140
acccgtatga ttactttgga atggcgacag gtgatacagt agaaatttct ccttttata   7200
ccaaaaacac gaccggacca aggcgtcaca gtgtctacag agactataga tttctcgaaa   7260
tcgcaaatta tcaagtcagg gatttggaaa ccggacaaat aagacccccct aaaaaaagaa   7320
actttctaac agatgaacaa ttcactatag gctgggatgc aatggaagaa aaggaatctg   7380
tatgtactct cagtaaatgg attgaagtcc cggaagcagt tcgtgtttcg tacaaaaaca   7440
gttaccactt ttcacttaaa gatatgacta tgacgttctc gtccggaaaa caacctttta   7500
acatcagcag gcttcatttg gctgaatgcg ttcctaccat agcctcggag gccatagatg   7560
gcatctttgc cagaaagtat agttcgactc atgtccgttc tggggacatc gaatactatc   7620
tcggtagtgg cggatttctg atcgcatttc agaaactcat gagccatggc ttggctgaaa   7680
tgtacctaga agaggcacaa agacaaaatc atctcccgag agggagagag cgtcgccaag   7740
```

-continued

```
ccgcaggtcg ccgcacggcg tcgctgcagt ctggacctca gggtgataga attactaccc   7800
acagttctgc aacatttgcc atgttacaat ttgcatacga caaaatccaa gcccatgtta   7860
acgagcttat cggaaatttg ttggaagcgt ggtgtgagct tcagaaccgc caactgattg   7920
tatggcatga gatgaagaaa ctaaacccga actcactgat gacatctttg ttcggacaac   7980
ctgtaagcgc caggctattg ggagacatcg tagcggtatc aaaatgtata gaaattccaa   8040
tcgaaaatat taggatgcag gattccatgc gcatgccagg ggacccaacc atgtgctata   8100
ccagaccagt acttattttc aggtattcgt cctcccctga gtcacagttt tctgcgaact   8160
caacagaaaa ccacaatctt gacatattag gccaactcgg agaacataat gaaattttac   8220
aagggcggaa tttgatagaa ccatgcatga tcaatcacag acggtacttt ctgttgggag   8280
aaaactacct tctttacgaa gactatacat ttgttagaca agtaaatgct tccgagatcg   8340
aagaagtgag cacattcatc aacttgaacg ccactatact agaagatttg gactttgtgc   8400
ccgtcgaagt atacactcgc gaggaactca gagatactgg gactttaaac tatgatgatg   8460
tggtcagata tcaaaatatt tataacaaaa ggttcagaga cattgacact gtaatacgtg   8520
gagatagggg agatgcaatc tttagagcaa tagcagattt ttttggcaac actcttggag   8580
aagtaggaaa ggcattggga actgtagtga tgacagccgc ggcagcagta atttctacag   8640
tatctggcat cgcctcattt ctttctaacc cgttcgccgc actcggaatt gggatagcgg   8700
tggtggtgag cattatttta ggactgctgg cgttcaaata tgtaatgaac ctgaaatcaa   8760
acccagttca ggttctgttc ccaggcgcag ttcccccggc cggaactcct ccacgaccct   8820
ctagacgtta ctacaaggat gaggaggttg aggaggatag tgatgaggac gacaggatac   8880
ttgccaccag agttctgaaa ggccttgagc ttctacacaa ggatgaacag aaagctcgaa   8940
gacagaaagc gcggttttct gcttttgcta aaaatatgag aaacctattt cgcagaaaac   9000
cccgaaccaa ggaagatgac taccccctgc tcgaataccc ttcgtgggca gaagaaagcg   9060
aagacgaata agctgtgtgt aactaccgtg tactaagccc cactcaccca gatcatcatg   9120
acacaaaaaa ctaatcgtta cctctctcgc ttcctcagcc ccactgaatg atcgcgtaac   9180
cgtaattaat ctagctacat taaggattaa gaaaaaatac gggtagaatt ggagtgcccc   9240
aattgtgcca agatggactc atctaggaca attgggctgt actttgattc tgcccattct   9300
tctagcaacc tgttagcatt tccgatcgtc ctacaagaca caggagatgg gaagaagcaa   9360
atcgccccgc aatataggat ccagcgcctt gacttgtgga ctgatagtaa ggaggactca   9420
gtattcatca ccacctatgg attcatcttt caagttggga atgaagaagc cactgtcggc   9480
atgatcgatg ataaacccaa gcgcgagtta ctttccgctg cgatgctctg cctaggaagc   9540
gtcccaaata ccggagacct tattgagctg gcaagggcct gtctcactat gatagtcaca   9600
tgcaagaaga gtgcaactaa tgctgagaga atggttttct cagtagtgca ggcaccccaa   9660
gtgctgcaaa gctgtagggt tgtggcaaac aaatactcat cagtgaatgc agtcaagcac   9720
gtgaaagcgc cagagaagat tcccgggagt ggaaccctag aatacaaggt gaactttgtc   9780
tccttgactg tggtaccgaa gaaggatgtc tacaagatcc ctgctgcagt attgaaggtt   9840
tctggctcga gtctgtacaa tcttgcgctc aatgtcacta ttaatgtgga ggtagacccg   9900
aggagtcctt tggttaaatc tctgtctaag tctgacagcg gatactatgc taacctcttc   9960
ttgcatattg gacttatgac caccgtagat aggaaggggg agaaagtgac atttgacaag  10020
ctggaaaaga aaataaggag ccttgatcta tctgtcgggc tcagtgatgt gctcgggcct  10080
tccgtgttgg taaaagcaag aggtgcacgg actaagcttt tggcaccttt cttctctagc  10140
```

agtgggacag cctgctatcc catagcaaat gcttctcctc aggtggccaa gatactctgg 10200
agtcaaaccg cgtgcctgcg gagcgttaaa atcattatcc aagcaggtac ccaacgcgct 10260
gtcgcagtga ccgccgacca cgaggttacc tctactaagc tggagaaggg gcacacccctt 10320
gccaaataca atccttttaa gaaataagct gcgtctctga gattgcgctc cgcccactca 10380
cccagatcat catgacacaa aaaactaatc tgtcttgatt atttacagtt agttaacctg 10440
tctatcaagt tagaaaaaac acgggtagaa gattctggat cccggttggc gccctccagg 10500
tgcaagatgg gctccagacc ttctaccaag aacccagcac ctatgatgct gactatccgg 10560
gttgcgctgg tactgagttg catctgtccg gcaaactcca ttgatggcag gcctcttgca 10620
gctgcaggaa ttgtggttac aggagacaaa gccgtcaaca tatacacctc atcccagaca 10680
ggatcaatca tagttaagct cctcccgaat ctgcccaagg ataaggaggc atgtgcgaaa 10740
gccccccttgg atgcatacaa caggacattg accactttgc tcaccccccct tggtgactct 10800
atccgtagga tacaagagtc tgtgactaca tctggagggg ggagacaggg gcgccttata 10860
ggcgccatta ttggcggtgt ggctcttggg gttgcaactg ccgcacaaat aacagcggcc 10920
gcagctctga tacaagccaa acaaaatgct gccaacatcc tccgacttaa agagagcatt 10980
gccgcaacca atgaggctgt gcatgaggtc actgacggat tatcgcaact agcagtggca 11040
gttgggaaga tgcagcagtt tgttaatgac caacttaata aaacagctca ggaattagac 11100
tgcatcaaaa ttgcacagca agttggtgta gagctcaacc tgtacctaac cgaattgact 11160
acagtattcg gaccacaaat cacttcacct gctttaaaca agctgactat tcaggcactt 11220
tacaatctag ctggtggaaa tatggattac ttattgacta agttaggtgt agggaacaat 11280
caactcagct cattaatcgg tagcggctta atcaccggta accctattct atacgactca 11340
cagactcaac tcttgggtat acgggtaact ctaccttcag tcgggaacct aaataatatg 11400
cgtgccacct acttggaaac cttatccgta agcacaacca ggggatttgc ctcggcactt 11460
gtccccaaag tggtgacaca ggtcggttct gtgatagaag aacttgacac ctcatactgt 11520
atagaaactg acttagattt atattgtaca agaatagtaa cgttccctat gtcccctggt 11580
atttattcct gcttgagcgg caatacgtcg gcctgtatgt actcaaagac cgaaggcgca 11640
cttactacac catacatgac tatcaaaggt tcagtcatcg ccaactgcaa gatgacaaca 11700
tgtagatgtg taaacccccc gggtatcata tcgcaaaact atggagaagc cgtgtctcta 11760
atagataaac aatcatgcaa tgttttatcc ttaggcggga taactttaag gctcagtggg 11820
gaattcgatg taacttatca gaagaatatc tcaatacaag attctcaagt aataataaca 11880
ggcaatcttg atatctcaac tgagcttggg aatgtcaaca actcgatcag taatgctttg 11940
aataagttag aggaaagcaa cagaaaacta gacaaagtca atgtcaaact gactagcaca 12000
tctgctctca ttacctatat cgttttgact atcatatctc ttgtttttgg tatacttagc 12060
ctgattctag catgctacct aatgtacaag caaaaggcgc aacaaaagac cttattatgg 12120
cttgggaata atactctaga tcagatgaga gccactacaa aaatgtgaac acagatgagg 12180
aacgaaggtt tccctaatag taatttgtgt gaaagttctg gtagtctgtc agttcagaga 12240
gttaagaaaa aactaccggt tgtagatgac caaaggacga tatacgggta gaacggtaag 12300
agaggccgcc cctcaattgc gagccaggct tcacaacctc cgttctaccg cttcaccgac 12360
aacagtcctc aatcatggac cgcgccgtta gccaagttgc gttagagaat gatgaaagag 12420
aggcaaaaaa tacatggcgc ttgatattcc ggattgcaat cttattctta acagtagtga 12480

-continued

```
ccttggctat atctgtagcc tccctttat atagcatggg ggctagcaca cctagcgatc  12540
ttgtaggcat accgactagg aattccaggg cagaagaaaa gattacatct acacttggtt  12600
ccaatcaaga tgtagtagat aggatatata agcaagtggc ccttgagtct ccgttggcat  12660
tgttaaaaac tgagaccaca attatgaacg caataacatc tctctcttat cagattaatg  12720
gagctgcaaa caacagtggg tggggggcac ttatccatga cccagattat atagggggga  12780
taggcaaaga actcattgta gatgatgcta gtgatgtcac atcattctat ccctctgcat  12840
ttcaagaaca tctgaatttt atcccggcgc ctactacagg atcaggttgc actcgaatac  12900
cctcatttga catgagtgct acccattact gctacaccca taatgtaata ttgtctggat  12960
gcagagatca ctcacattca tatcagtatt tagcacttgg tgtgctccgg acatctgcaa  13020
cagggagggt attcttttct actctgcgtt ccatcaacct ggacgacacc caaaatcgga  13080
agtcttgcag tgtgagtgca actcccctgg gttgtgatat gctgtgctcg aaagtcacgg  13140
agacagagga agaagattat aactcagctg tccctacgcg gatggtacat gggaggttag  13200
ggttcgacgg ccagtaccac gaaaaggacc tagatgtcac aacattattc ggggactggg  13260
tggccaacta cccaggagta gggggtggat cttttattga cagccgcgta tggttctcag  13320
tctacggagg gttaaaaccc aattcaccca gtgacactgt acaggaaggg aaatatgtga  13380
tatacaagcg atacaatgac acatgcccag atgagcaaga ctaccagatt cgaatggcca  13440
ggtcttcgta taagcctgga cggtttggtg ggaaacgcat acagcaggct atcttatcta  13500
tcaaggtgtc aacatcctta ggcgaagacc cggtactgac tgtaccgccc aacacagtca  13560
cactcatggg ggccgaaggc agaattctca cagtagggac atctcatttc ttgtatcaac  13620
gagggtcatc atacttctct cccgcgttat tatatcctat gacagtcagc aacaaaacag  13680
ccactcttca tagtccttat acattcaatg ccttcactcg gccaggtagt atcccttgcc  13740
aggcttcagc aagatgcccc aacccgtgtg ttactggagt ctatacagat ccacatcccc  13800
taatcttcta tagaaaccac accttgcgag ggtattcgg gacaatgctt gatggtgtac  13860
aagcaagact taaccctgcg tctgcagtat tcgatagcac atcccgcagt cgcattactc  13920
gagtgagttc aagcagtacc aaagcagcat acacaacatc aacttgtttt aaagtggtca  13980
agactaataa gacctattgt ctcagcattg ctgaaatatc taatactctc ttcggagaat  14040
tcagaatcgt cccgttacta gttgagatcc tcaaagatga cggggttaga gaagccaggt  14100
ctggctagtt gagtcaatta taaaggagtt ggaaagatgg cattgtatca cctatcttct  14160
gcgacatcaa gaatcaaacc gaatgccggc gcgtgctcga attccatgtt gccagttgac  14220
cacaatcagc cagtgctcat gcgatcagat taagccttgt caatagtctc ttgattaaga  14280
aaaaatgtaa gtggcaatga gatacaaggc aaaacagctc atggtaaata atacgggtag  14340
aacatggcga gctccggtcc tgaaagggca gagcatcaga ttatcctacc agagtcacac  14400
ctgtcttcac cattggtcaa gcacaaacta ctctattact ggaaattaac tgggctaccg  14460
cttcctgatg aatgtgactt cgaccacctc attctcagcc gacaatggaa aaaaatactt  14520
gaatcggcct ctcctgatac tgagagaatg atagaactcg gaagggcagt acaccaaact  14580
cttaaccaca attccagaat aaccggagtg ctccacccca ggtgtttaga agaactggct  14640
aatattgagg tcccagattc aaccaacaaa tttcggaaga ttgagaagaa gatccaaatt  14700
cacaacacga gatatggaga actgttcaca aggctgtgta cgcatataga gaagaaactg  14760
ctggggtcat cttggtctaa caatgtcccc cggtcagagg agttcagcag cattcgtacg  14820
gatccggcat tctggtttca ctcaaaatgg tccacagcca agtttgcatg gctccatata  14880
```

```
aaacagatcc agaggcatct gatggtggca gctaggacaa ggtctgcggc caacaaattg  14940
gtgatgctaa cccataaggt aggccaagtc tttgtcactc ctgaacttgt cgttgtgacg  15000
catacgaatg agaacaagtt cacatgtctt acccaggaac ttgtattgat gtatgcagat  15060
atgatggagg gcagagatat ggtcaacata atatcaacca cggcggtgca tctcagaagc  15120
ttatcagaga aaattgatga cattttgcgg ttaatagacg ctctggcaaa agacttgggt  15180
aatcaagtct acgatgttgt atcactaatg gagggatttg catacggagc tgtccagcta  15240
ctcgagccgt caggtacatt tgcaggagat ttcttcgcat tcaacctgca ggagcttaaa  15300
gacattctaa ttggcctcct ccccaatgat atagcagaat ccgtgactca tgcaatcgct  15360
actgtattct ctggtttaga acagaatcaa gcagctgaga tgttgtgtct gttgcgtctg  15420
tggggtcacc cactgcttga gtcccgtatt gcagcaaagg cagtcaggag ccaaatgtgc  15480
gcaccgaaaa tggtagactt tgatatgatc cttcaggtac tgtctttctt caagggaaca  15540
atcatcaacg ggtacagaaa gaagaatgca ggtgtgtggc cgcgagtcaa agtggataca  15600
atatatggga aggtcattgg gcaactacat gcagattcag cagagatttc acacgatatc  15660
atgttgagag agtataagag tttatctgca cttgaatttg agccatgtat agaatatgac  15720
cctgtcacca acctgagcat gttcctaaaa gacaaggcaa tcgcacaccc caacgataat  15780
tggcttgcct cgtttaggcg gaaccttctc tccgaagacc agaagaaaca tgtaaaagaa  15840
gcaacttcga ctaatcgcct cttgatagag tttttagagt caaatgattt tgatccatat  15900
aaagagatgg aatatctgac gacccttgag taccttagag atgacaatgt ggcagtatca  15960
tactcgctca aggagaagga agtgaaagtt aatggacgga tcttcgctaa gctgacaaag  16020
aagttaagga actgtcaggt gatggcggaa gggatcctag ccgatcagat tgcacctttc  16080
tttcagggaa atggagtcat tcaggatagc atatccttga ccaagagtat gctagcgatg  16140
agtcaactgt cttttaacag caataagaaa cgtatcactg actgtaaaga aagagtatct  16200
tcaaaccgca atcatgatcc gaaaagcaag aaccgtcgga gagttgcaac cttcataaca  16260
actgacctgc aaaagtactg tcttaattgg agatatcaga cgatcaaatt gttcgctcat  16320
gccatcaatc agttgatggg cctacctcat ttcttcgagt ggattcacct aagactgatg  16380
gacactacga tgttcgtagg agaccctttc aatcctccaa gtgaccctac tgactgtgac  16440
ctctcaagag tccctaatga tgacatatat attgtcagtg ccagaggggg tatcgaagga  16500
ttatgccaga agctatggac aatgatctca attgctgcaa tccaacttgc tgcagctaga  16560
tcgcattgtc gtgttgcctg tatggtacag ggtgataatc aagtaatagc agtaacgaga  16620
gaggtaagat cagatgactc tccggagatg gtgttgacac agttgcatca agccagtgat  16680
aatttcttca aggaattaat ccatgtcaat catttgattg gccataattt gaaggatcgt  16740
gaaaccatca ggtcagacac attcttcata tacagcaaac gaatcttcaa agatggagca  16800
atcctcagtc aagtcctcaa aaattcatct aaattagtgc tagtgtcagg tgatctcagt  16860
gaaaacactg taatgtcctg tgccaacatt gcctctactg tagcacggct atgcgagaac  16920
gggcttccca aagacttctg ttactattta aactatataa tgagttgtgt gcagacatac  16980
tttgactctg agttctccat caccaacaat tcgcaccccg atcttaatca gtcgtggatt  17040
gaggacatct cttttgtgca ctcatatgtt ctgactcctg cccaattagg gggactgagt  17100
aaccttcaat actcaaggct ctacactaga aatatcggtg acccggggac tactgctttt  17160
gcagagatca agcgactaga agcagtggga ttactgagtc ctaacattat gactaatatc  17220
```

-continued

```
ttaactaggc cgcctgggaa tggagattgg gccagtctgt gcaacgaccc atactctttc  17280
aattttgaga ctgttgcaag cccaaatatt gttcttaaga aacatacgca aagagtccta  17340
tttgaaactt gttcaaatcc cttattgtct ggagtgcaca cagaggataa tgaggcagaa  17400
gagaaggcat tggctgaatt cttgcttaat caagaggtga ttcatccccg cgttgcgcat  17460
gccatcatgg aggcaagctc tgtaggtagg agaaagcaaa ttcaagggct tgttgacaca  17520
acaaacaccg taattaagat tgcgcttact aggaggccat taggcatcaa gaggctgatg  17580
cggatagtca attattctag catgcatgca atgctgttta gagacgatgt tttttcctcc  17640
agtagatcca accacccctt agtctcttct aatatgtgtt ctctgacact ggcagactat  17700
gcacggaata gaagctggtc acctttgacg ggaggcagga aaatactggg tgtatctaat  17760
cctgatacga tagaactcgt agagggtgag attcttagtg taagcggagg gtgtacaaga  17820
tgtgacagcg gagatgaaca atttacttgg ttccatcttc caagcaatat agaattgacc  17880
gatgacacca gcaagaatcc tccgatgagg gtaccatatc tcgggtcaaa gacacaggag  17940
aggagagctg cctcacttgc aaaaaatagct catatgtcgc cacatgtaaa ggctgcccta  18000
agggcatcat ccgtgttgat ctgggcttat ggggataatg aagtaaattg gactgctgct  18060
cttacgattg caaaatctcg gtgcaatgta aacttagagt atcttcggtt actgtcccct  18120
ttacccacgg ctgggaatct tcaacataga ctagatgatg gtataactca gatgacattc  18180
acccctgcat ctctctacag ggtgtcacct tacattcaca tatccaatga ttctcaaagg  18240
ctgttcactg aagaaggagt caaagagggg aatgtggttt accaacagat catgctcttg  18300
ggtttatctc taatcgaatc gatctttcca atgacaacaa ccaggacata tgatgagatc  18360
acactgcacc tacatagtaa atttagttgc tgtatcagag aagcacctgt tgcggttcct  18420
ttcgagctac ttggggtggt accggaactg aggacagtga cctcaaataa gtttatgtat  18480
gatcctagcc ctgtatcgga gggagacttt gcgagacttg acttagctat cttcaagagt  18540
tatgagctta atctggagtc atatcccacg atagagctaa tgaacattct ttcaatatcc  18600
agcgggaagt tgattggcca gtctgtggtt tcttatgatg aagatacctc cataaagaat  18660
gatgccataa tagtgtatga caatacccga aattggatca gtgaagctca gaattcagat  18720
gtggtccgcc tatttgaata tgcagcactt gaagtgctcc tcgactgttc ttaccaactc  18780
tattacctga gagtaagagg cctagacaat attgtcttat atatgggtga tttatacaag  18840
aatatgccag gaattctact ttccaacatt gcagctacaa tatctcatcc tgtcattcat  18900
tcaaggttac atgcagtggg cctggtcaac catgacggat cacaccaact tgcagatacg  18960
gattttatcg aaatgtctgc aaaactgtta gtatcttgca cccgacgtgt gatctccggc  19020
ttatattcag gaaataagta tgatctgctg ttcccatctg tcttagatga taacctgaat  19080
gagaagatgc ttcagctgat atcccggtta tgctgtctgt acacggtact ctttgctaca  19140
acaagagaaa tcccgaaaat aagaggctta actgcagaag agaaatgttc aatactcact  19200
gagtatttac tgtcggatgc tgtgaaacca ttacttagcc ccgatcaagt gagctctatc  19260
atgtctccta acataattac attcccagct aatctgtact acatgtctcg gaagagcctc  19320
aatttgatca gggaaaggga ggacagggat actatcctgg cgttgttgtt cccccaagag  19380
ccattattag agttcccttc tgtgcaagat attggtgctc gagtgaaaga tccattcacc  19440
cgacaacctg cggcattttt gcaagagtta gatttgagtg ctccagcaag gtatgacgca  19500
ttcacactta gtcagattca tcctgaactc acatctccaa atccggagga agactactta  19560
gtacgatact tgttcagagg gatagggact gcatcttcct cttggtataa ggcatcccat  19620
```

```
ctcctttctg tacccgaggt aagatgtgca agacacggga actccttata cttggctgaa  19680

ggaagcggag ccatcatgag tcttcttgaa ctgcatgtac cacatgaaac tatctattac  19740

aatacgctct tttcaaatga gatgaacccc ccgcaacgac atttcgggcc gaccccaact  19800

cagtttttga attcggttgt ttataggaat ctacaggcgg aggtaacatg caaggatgga  19860

tttgtccaag agttccgtcc attatggaga gaaaatacag aggaaagtga cctgacctca  19920

gataaagcag tggggtatat tacatctgca gtaccctaca gatctgtatc attgctgcat  19980

tgtgacattg aaattcctcc agggtccaat caaagcttac tagatcaact agctatcaat  20040

ttatctctga ttgccatgca ttctgtaagg gagggcgggg tagtaatcat caaagtgttg  20100

tatgcaatgg gatactactt tcatctactc atgaacttgt ttgctccgtg ttccacaaaa  20160

ggatatattc tctctaatgg ttatgcatgt cgaggggata tggagtgtta cctggtattt  20220

gtcatgggtt acctgggcgg gcctacattt gtacatgagg tggtgaggat ggcaaaaact  20280

ctggtgcagc ggcacggtac gcttttgtct aaatcagatg agatcacact gaccaggtta  20340

ttcacctcac agcggcagcg tgtgacagac atcctatcca gtcctttacc aagattaata  20400

aagtacttga ggaagaatat tgacactgcg ctgattgaag ccgggggaca gcccgtccgt  20460

ccattctgtg cggagagtct ggtgagcacg ctagcgaaca taactcagat aacccagatc  20520

atcgctagcc acattgacac agttatccgg tctgtgatat atatggaagc tgagggtgat  20580

ctcgctgaca cagtatttct atttacccct tacaatctct ctactgacgg gaaaaagagg  20640

acatcactta aacagtgcac gagacagatc ctagaggtta caatactagg tcttagagtc  20700

gaaaatctca ataaaatagg cgatataatc agcctagtgc ttaaaggcat gatctccatg  20760

gaggacctta tcccactaag gacatacttg aagcatagta cctgccctaa atatttgaag  20820

gctgtcctag gtattaccaa actcaaagaa atgtttacag acacttctgt actgtacttg  20880

actcgtgctc aacaaaaatt ctacatgaaa actataggca atgcagtcaa aggatattac  20940

agtaactgtg actcctaacg aaaatcacat attaataggc tcctttttttg gccaattgta  21000

ttcttgttga tttaattata ttatgttaga aaaaagttga actctgactc cttaggactc  21060

gaattcgaac tcaaataaat gtctttaaaa aaggttgcgc acaattattc ttgagtgtag  21120

tctcgtcatt caccaaatct ttgtttggtg gccggcatgg tcccagcctc ctcgct      21176
```

```
<210> SEQ ID NO 14
<211> LENGTH: 18036
<212> TYPE: DNA
<213> ORGANISM: Artificial Sequence
<220> FEATURE:
<223> OTHER INFORMATION: chimeric viral genome

<400> SEQUENCE: 14

accaaacaga gaatccgtga gtcgcgataa aaggcgaaag agcaattgaa gtcacacggg     60

tagaaggtgt gaatctcgag tgcgagcccg aagcacaaac tcgagaaagc cttctgccaa    120

catgtcttcc gtatttgatg agtacgaaca gctcctcgcg gctcagactc gccccaatgg    180

agctcatgga gggggagaaa aagggagtac cttaaaagta gacgtcccgg tattcactct    240

taacagtgat gacccagaag atagatggag ctttgtggta ttctgcctcc ggattgctgt    300

tagcgaagat gccaacaaac cactcaggca aggtgctctc atatctcttt tatgctccca    360

ctcacaggta atgaggaacc atgttgccct tgcagggaaa cagaatgaag ccacattggc    420

cgtgcttgag attgatggct ttgccaacgg cacgccccag ttcaacaata ggagtggagt    480
```

-continued

```
gtctgaagag agagcacaga gatttgcgat gatagcagga tctctccctc gggcatgcag    540
caacggaacc ccgttcgtca cagccggggc cgaagatgat gcaccagaag acatcaccga    600
taccctggag aggatcctct ctatccaggc tcaagtatgg gtcacagtag caaaagccat    660
gactgcgtat gagactgcag atgagtcgga aacaaggcga atcaataagt atatgcagca    720
aggcagggtc caaaagaaat acatcctcta ccccgtatgc aggagcacaa tccaactcac    780
gatcagacag tctcttgcag tccgcatctt tttggttagc gagctcaaga gaggccgcaa    840
cacggcaggt ggtacctcta cttattataa cctggtaggg gacgtagact catacatcag    900
gaataccggg cttactgcat tcttcttgac actcaagtac ggaatcaaca ccaagacatc    960
agcccttgca cttagtagcc tctcaggcga catccagaag atgaagcagc tcatgcgttt   1020
gtatcggatg aaaggagata atgcgccgta catgacatta cttggtgata gtgaccagat   1080
gagctttgcg cctgccgagt atgcacaact ttactccttt gccatgggta tggcatcagt   1140
cctagataaa ggtactggga aataccaatt tgccagggac tttatgagca catcattctg   1200
gagacttgga gtagagtacg ctcaggctca gggaagtagc attaacgagg atatggctgc   1260
cgagctaaag ctaaccccag cagcaaggag gggcctggca gctgctgccc aacgggtctc   1320
cgaggagacc agcagcatag acatgcctac tcaacaagtc ggagtcctca ctgggcttag   1380
cgaggggggg tcccaagctc tacaaggcgg atcgaataga tcgcaagggc aaccagaagc   1440
cggggatggg gagacccaat tcctggatct gatgagagcg gtagcaaata gcatgaggga   1500
ggcgccaaac tctgcacagg gcactcccca atcggggcct cccccaactc ctgggccatc   1560
ccaagataac gacaccgact gggggtattg atggacaaaa cccagcctgc ttccacaaaa   1620
acatcccaat gccctcaccc gtagtcgacc cctcgatttg cggctctata tgaccacacc   1680
ctcaaacaaa catcccccctc tttcctccct cccccctgctg tacaactccg cacgccctag   1740
ataccacagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaaggcaa ccccgatcga caggacagat   2100
ctgacaaaca accatccaca cccgggcaaa cgaccccgca tgacagcccg ccggccacat   2160
ccgccgacca gccccccacc caggccacag acgaagccgt cgacacacag ctcaggaccg   2220
gagcaagcaa ctctctgctg ttgatgcttg acaagctcag caataaatcg tccaatgcta   2280
aaaagggccc atggtcgagc cccaagaggg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aataccctttg   2520
tatctgcgga tcatgtccag ccacctgtag actttgtgca agcgatgatg tctatgatgg   2580
aggcgatatc acagagagta agtaaggtcg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
cctctcccta tgtgacacaa ggaggcgaaa tggcacttaa taaactttcg caaccagtgc   2880
```

-continued

```
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc ccccgcagac ccaaggtcca actctccaag cggcaatcct   3180
ctctcgcttc ttcagcccca ctgaatgatc gcgtaaccgt aattaatcta gctacattaa   3240
ggattaagaa aaaatacggg tagaattgga gtgccccaat tgtgagttta gttgatagtt   3300
gtagccacca tgcaatccta catcgccgtg aacattgaca tggctagctt gaaaatgctg   3360
atctgcgtgt gcgtggcaat cctgatccca tctaccctat ctcaagattc acacggaatt   3420
gctggaataa tagaccctcg tgatacagcc agcatggatg ttggaaaaat ctctttctcc   3480
gaagccattg ggtcgggggc accgaaagaa ccccagatta gaaacagaat tttgcgtgc   3540
tcatctccaa ctggcgccag tgttgcgagg cttgcccagc cacgacattg tcaccgacat   3600
gccgattcga ctaacatgac tgaaggaatt gccgtagtct tcaagcaaaa cattgccccg   3660
tacgtcttta atgtgactct atactataaa catataacca cagttactac gtgggcatta   3720
ttctcaagac cccaaataac aaatgagtac gtgaccaggg ttccaataga ctatcatgaa   3780
attgtcagga ttgatcgatc gggagaatgc tcatccaaag caacgtatca taaaaatttc   3840
atgtttttg aagcttacga caatgatgaa gcagaaaaaa aattgcccct ggttccatca   3900
ctgttaagat caactgtctc caaggcgttt catacaacta actttactaa gcgacatcaa   3960
accctgggat accgaacgtc tacatcggtc gactgtgttg tggaatatct acaggctaga   4020
tctgtatacc cgtatgatta ctttggaatg gcgacaggtg atacagtaga aatttctcct   4080
ttttatacca aaaacacgac cggaccaagg cgtcacagtg tctacagaga ctatagattt   4140
ctcgaaatcg caaattatca agtcagggat ttggaaaccg gacaaataag accccctaaa   4200
aaaagaaact ttctaacaga tgaacaattc actataggct gggatgcaat ggaagaaaag   4260
gaatctgtat gtactctcag taaatggatt gaagtcccgg aagcagttcg tgtttcgtac   4320
aaaaacagtt accacttttc acttaaagat atgactatga cgttctcgtc cggaaaacaa   4380
ccttttaaca tcagcaggct tcatttggct gaatgcgttc ctaccatagc ctcggaggcc   4440
atagatggca tctttgccag aaagtatagt tcgactcatg tccgttctgg ggacatcgaa   4500
tactatctcg gtagtggcgg atttctgatc gcatttcaga aactcatgag ccatggcttg   4560
gctgaaatgt acctagaaga ggcacaaaga caaaatcatc tcccgagagg gagagagcgt   4620
cgccaagccg caggtcgccg cacggcgtcg ctgcagtctg gacctcaggg tgatagaatt   4680
actacccaca gttctgcaac atttgccatg ttacaatttg catacgacaa aatccaagcc   4740
catgttaacg agcttatcgg aaatttgttg gaagcgtggt gtgagcttca gaaccgccaa   4800
ctgattgtat ggcatgagat gaagaaacta aacccgaact cactgatgac atctttgttc   4860
ggacaacctg taagcgccag gctattggga gacatcgtag cggtatcaaa atgtatagaa   4920
attccaatcg aaaatattag gatgcaggat tccatgcgca tgccagggga cccaaccatg   4980
tgctatacca gaccagtact tattttcagg tattcgtcct cccctgagtc acagttttct   5040
gcgaactcaa cagaaaacca caatcttgac atattaggcc aactcggaga acataatgaa   5100
attttacaag ggcggaattt gatagaacca tgcatgatca atcacagacg gtactttctg   5160
ttgggagaaa actaccttct ttacgaagac tatacatttg ttagacaagt aaatgcttcc   5220
```

-continued

```
gagatcgaag aagtgagcac attcatcaac ttgaacgcca ctatactaga agatttggac   5280
tttgtgcccg tcgaagtata cactcgcgag gaactcagag atactgggac tttaaactat   5340
gatgatgtgg tcagatatca aaatatttat aacaaaaggt tcagagacat tgacactgta   5400
atacgtggag ataggggaga tgcaatcttt agagcaatag cagatttttt tggcaacact   5460
cttggagaag taggaaaggc attgggaact gtagtgatga cagccgcggc agcagtaatt   5520
tctacagtat ctggcatcgc ctcatttctt tctaacccgt tcgccgcact cggaattggg   5580
atagcggtgg tggtgagcat tattttagga ctgctggcgt tcaaatatgt aatgaacctg   5640
aaatcaaacc cagttcaggt tctgttccca ggcgcagttc ccccggccgg aactcctcca   5700
cgaccctcta gacgttacta caaggatgag gaggttgagg aggatagtga tgaggacgac   5760
aggatacttg ccaccagagt tctgaaaggc cttgagcttc tacacaagga tgaacagaaa   5820
gctcgaagac agaaagcgcg gttttctgct tttgctaaaa atatgagaaa cctatttcgc   5880
agaaaacccc gaaccaagga agatgactac cccctgctcg aataccccttc gtgggcagaa   5940
gaaagcgaag acgaataagc tgtgtgtaac taccgtgtac taagccccac tcacccagat   6000
catcatgaca caaaaaacta atcgttacct ctctcgcttc ctcagcccca ctgaatgatc   6060
gcgtaaccgt aattaatcta gctacattaa ggattaagaa aaaatacggg tagaattgga   6120
gtgccccaat tgtgccaaga tggactcatc taggacaatt gggctgtact ttgattctgc   6180
ccattcttct agcaacctgt tagcatttcc gatcgtccta caagacacag gagatgggaa   6240
gaagcaaatc gccccgcaat ataggatcca gcgccttgac ttgtggactg atagtaagga   6300
ggactcagta ttcatcacca cctatggatt catctttcaa gttgggaatg aagaagccac   6360
tgtcggcatg atcgatgata aacccaagcg cgagttactt tccgctgcga tgctctgcct   6420
aggaagcgtc ccaaataccg gagaccttat tgagctggca agggcctgtc tcactatgat   6480
agtcacatgc aagaagagtg caactaatgc tgagagaatg gttttctcag tagtgcaggc   6540
accccaagtg ctgcaaagct gtagggttgt ggcaaacaaa tactcatcag tgaatgcagt   6600
caagcacgtg aaagcgccag agaagattcc cgggagtgga accctagaat acaaggtgaa   6660
ctttgtctcc ttgactgtgg taccgaagaa ggatgtctac aagatccctg ctgcagtatt   6720
gaaggtttct ggctcgagtc tgtacaatct tgcgctcaat gtcactatta atgtggaggt   6780
agacccgagg agtcctttgg ttaaatctct gtctaagtct gacagcggat actatgctaa   6840
cctcttcttg catattggac ttatgaccac cgtagatagg aaggggaaga aagtgacatt   6900
tgacaagctg gaaaagaaaa taaggagcct tgatctatct gtcgggctca gtgatgtgct   6960
cgggccttcc gtgttggtaa aagcaagagg tgcacggact aagcttttgg cacctttctt   7020
ctctagcagt gggacagcct gctatcccat agcaaatgct tctcctcagg tggccaagat   7080
actctggagt caaaccgcgt gcctgcggag cgttaaaatc attatccaag caggtaccca   7140
acgcgctgtc gcagtgaccg ccgaccacga ggttacctct actaagctgg agaaggggca   7200
caccccttgcc aaatacaatc cttttaagaa ataagctgcg tctctgagat tgcgctccgc   7260
ccactcaccc agatcatcat gacacaaaaa actaatctgt cttgattatt tacagttagt   7320
taacctgtct atcaagttag aaaaaacacg ggtagaagat tctggatccc ggttggcgcc   7380
ctccaggtgc aagatgggct ccagaccttc taccaagaac ccagcaccta tgatgctgac   7440
tatccgggtt gcgctggtac tgagttgcat ctgtccggca aactccattg atggcaggcc   7500
tcttgcagct gcaggaattg tggttacagg agacaaagcc gtcaacatat acacctcatc   7560
ccagacagga tcaatcatag ttaagctcct cccgaatctg cccaaggata aggaggcatg   7620
```

```
tgcgaaagcc cccttggatg catacaacag gacattgacc actttgctca ccccccttgg   7680
tgactctatc cgtaggatac aagagtctgt gactacatct ggaggggga gacaggggcg    7740
ccttataggc gccattattg gcggtgtggc tcttggggtt gcaactgccg cacaaataac   7800
agcggccgca gctctgatac aagccaaaca aaatgctgcc aacatcctcc gacttaaaga   7860
gagcattgcc gcaaccaatg aggctgtgca tgaggtcact gacggattat cgcaactagc   7920
agtggcagtt gggaagatgc agcagtttgt taatgaccaa cttaataaaa cagctcagga   7980
attagactgc atcaaaattg cacagcaagt tggtgtagag ctcaacctgt acctaaccga   8040
attgactaca gtattcggac cacaaatcac ttcacctgct ttaaacaagc tgactattca   8100
ggcactttac aatctagctg gtggaaatat ggattactta ttgactaagt taggtgtagg   8160
gaacaatcaa ctcagctcat taatcggtag cggcttaatc accggtaacc ctattctata   8220
cgactcacag actcaactct tgggtatacg ggtaactcta ccttcagtcg ggaacctaaa   8280
taatatgcgt gccacctact tggaaacctt atccgtaagc acaaccaggg gatttgcctc   8340
ggcacttgtc cccaaagtgg tgacacaggt cggttctgtg atagaagaac ttgacacctc   8400
atactgtata gaaactgact tagatttata ttgtacaaga atagtaacgt tccctatgtc   8460
ccctggtatt tattcctgct tgagcggcaa tacgtcggcc tgtatgtact caaagaccga   8520
aggcgcactt actacaccat acatgactat caaaggttca gtcatcgcca actgcaagat   8580
gacaacatgt agatgtgtaa accccccggg tatcatatcg caaaactatg gagaagccgt   8640
gtctctaata gataaacaat catgcaatgt tttatcctta ggcgggataa ctttaaggct   8700
cagtggggaa ttcgatgtaa cttatcagaa gaatatctca atacaagatt ctcaagtaat   8760
aataacaggc aatcttgata tctcaactga gcttgggaat gtcaacaact cgatcagtaa   8820
tgctttgaat aagttagagg aaagcaacag aaaactagac aaagtcaatg tcaaactgac   8880
tagcacatct gctctcatta cctatatcgt tttgactatc atatctcttg tttttggtat   8940
acttagcctg attctagcat gctacctaat gtacaagcaa aaggcgcaac aaaagacctt   9000
attatggctt gggaataata ctctagatca gatgagagcc actacaaaaa tgtgaacaca   9060
gatgaggaac gaaggtttcc ctaatagtaa tttgtgtgaa agttctggta gtctgtcagt   9120
tcagagagtt aagaaaaaac taccggttgt agatgaccaa aggacgatat acgggtagaa   9180
cggtaagaga ggccgcccct caattgcgag ccaggcttca caacctccgt tctaccgctt   9240
caccgacaac agtcctcaat catggaccgc gccgttagcc aagttgcgtt agagaatgat   9300
gaaagagagg caaaaaatac atggcgcttg atattccgga ttgcaatctt attcttaaca   9360
gtagtgacct tggctatatc tgtagcctcc cttttatata gcatgggggc tagcacacct   9420
agcgatcttg taggcatacc gactaggaat tccagggcag aagaaaagat tacatctaca   9480
cttggttcca atcaagatgt agtagatagg atatataagc aagtggccct tgagtctccg   9540
ttggcattgt taaaaactga gaccacaatt atgaacgcaa taacatctct ctcttatcag   9600
attaatggag ctgcaaacaa cagtgggtgg ggggcactta tccatgaccc agattatata   9660
gggggatag gcaaagaact cattgtagat gatgctagtg atgtcacatc attctatccc    9720
tctgcatttc aagaacatct gaattttatc ccggcgccta ctacaggatc aggttgcact   9780
cgaatacct catttgacat gagtgctacc cattactgct acacccataa tgtaatattg    9840
tctggatgca gagatcactc acattcatat cagtatttag cacttggtgt gctccggaca   9900
tctgcaacag ggagggtatt cttttctact ctgcgttcca tcaacctgga cgacacccaa   9960
```

aatcggaagt cttgcagtgt gagtgcaact cccctgggtt gtgatatgct gtgctcgaaa 10020
gtcacggaga cagaggaaga agattataac tcagctgtcc ctacgcggat ggtacatggg 10080
aggttagggt tcgacggcca gtaccacgaa aaggacctag atgtcacaac attattcggg 10140
gactgggtgg ccaactaccc aggagtaggg ggtggatctt ttattgacag ccgcgtatgg 10200
ttctcagtct acggagggtt aaaacccaat tcacccagtg acactgtaca ggaagggaaa 10260
tatgtgatat acaagcgata caatgacaca tgcccagatg agcaagacta ccagattcga 10320
atggccaggt cttcgtataa gcctggacgg tttggtggga aacgcataca gcaggctatc 10380
ttatctatca aggtgtcaac atccttaggc gaagacccgg tactgactgt accgcccaac 10440
acagtcacac tcatgggggc cgaaggcaga attctcacag tagggacatc tcatttcttg 10500
tatcaacgag ggtcatcata cttctctccc gcgttattat atcctatgac agtcagcaac 10560
aaaacagcca ctcttcatag tccttataca ttcaatgcct tcactcggcc aggtagtatc 10620
ccttgccagg cttcagcaag atgccccaac ccgtgtgtta ctggagtcta tacagatcca 10680
catcccctaa tcttctatag aaaccacacc ttgcgagggg tattcgggac aatgcttgat 10740
ggtgtacaag caagacttaa ccctgcgtct gcagtattcg atagcacatc ccgcagtcgc 10800
attactcgag tgagttcaag cagtaccaaa gcagcataca caacatcaac ttgttttaaa 10860
gtggtcaaga ctaataagac ctattgtctc agcattgctg aaatatctaa tactctcttc 10920
ggagaattca gaatcgtccc gttactagtt gagatcctca aagatgacgg ggttagagaa 10980
gccaggtctg gctagttgag tcaattataa aggagttgga aagatggcat tgtatcacct 11040
atcttctgcg acatcaagaa tcaaaccgaa tgccggcgcg tgctcgaatt ccatgttgcc 11100
agttgaccac aatcagccag tgctcatgcg atcagattaa gccttgtcaa tagtctcttg 11160
attaagaaaa aatgtaagtg gcaatgagat acaaggcaaa acagctcatg gtaaataata 11220
cgggtagaac atggcgagct ccggtcctga aagggcagag catcagatta tcctaccaga 11280
gtcacacctg tcttcaccat tggtcaagca caaactactc tattactgga aattaactgg 11340
gctaccgctt cctgatgaat gtgacttcga ccacctcatt ctcagccgac aatggaaaaa 11400
aatacttgaa tcggcctctc ctgatactga gagaatgata gaactcggaa gggcagtaca 11460
ccaaactctt aaccacaatt ccagaataac cggagtgctc caccccaggt gtttagaaga 11520
actggctaat attgaggtcc cagattcaac caacaaattt cggaagattg agaagaagat 11580
ccaaattcac aacacgagat atggagaact gttcacaagg ctgtgtacgc atatagagaa 11640
gaaactgctg gggtcatctt ggtctaacaa tgtcccccgg tcagaggagt tcagcagcat 11700
tcgtacggat ccggcattct ggtttcactc aaaatggtcc acagccaagt ttgcatggct 11760
ccatataaaa cagatccaga ggcatctgat ggtggcagct aggacaaggt ctgcggccaa 11820
caaattggtg atgctaaccc ataaggtagg ccaagtcttt gtcactcctg aacttgtcgt 11880
tgtgacgcat acgaatgaga acaagttcac atgtcttacc caggaacttg tattgatgta 11940
tgcagatatg atggagggca gagatatggt caacataata tcaaccacgg cggtgcatct 12000
cagaagctta tcagagaaaa ttgatgacat tttgcggtta atagacgctc tggcaaaaga 12060
cttgggtaat caagtctacg atgttgtatc actaatggag ggatttgcat acggagctgt 12120
ccagctactc gagccgtcag gtacatttgc aggagatttc ttcgcattca acctgcagga 12180
gcttaaagac attctaattg gcctcctccc caatgatata gcagaatccg tgactcatgc 12240
aatcgctact gtattctctg gtttagaaca gaatcaagca gctgagatgt tgtgtctgtt 12300
gcgtctgtgg ggtcacccac tgcttgagtc ccgtattgca gcaaaggcag tcaggagcca 12360

-continued aatgtgcgca ccgaaaatgg tagactttga tatgatcctt caggtactgt ctttcttcaa 12420
gggaacaatc atcaacgggt acagaaagaa gaatgcaggt gtgtggccgc gagtcaaagt 12480
ggatacaata tatgggaagg tcattgggca actacatgca gattcagcag agatttcaca 12540
cgatatcatg ttgagagagt ataagagttt atctgcactt gaatttgagc catgtataga 12600
atatgaccct gtcaccaacc tgagcatgtt cctaaaagac aaggcaatcg cacaccccaa 12660
cgataattgg cttgcctcgt ttaggcggaa ccttctctcc gaagaccaga agaaacatgt 12720
aaaagaagca acttcgacta atcgcctctt gatagagttt ttagagtcaa atgattttga 12780
tccatataaa gagatggaat atctgacgac ccttgagtac cttagagatg acaatgtggc 12840
agtatcatac tcgctcaagg agaaggaagt gaaagttaat ggacggatct tcgctaagct 12900
gacaaagaag ttaaggaact gtcaggtgat ggcggaaggg atcctagccg atcagattgc 12960
acctttcttt cagggaaatg gagtcattca ggatagcata tccttgacca agagtatgct 13020
agcgatgagt caactgtctt ttaacagcaa taagaaacgt atcactgact gtaaagaaag 13080
agtatcttca aaccgcaatc atgatccgaa aagcaagaac cgtcggagag ttgcaacctt 13140
cataacaact gacctgcaaa agtactgtct taattggaga tatcagacga tcaaattgtt 13200
cgctcatgcc atcaatcagt tgatgggcct acctcatttc ttcgagtgga ttcacctaag 13260
actgatggac actacgatgt tcgtaggaga ccctttcaat cctccaagtg accctactga 13320
ctgtgacctc tcaagagtcc ctaatgatga catatatatt gtcagtgcca gagggggtat 13380
cgaaggatta tgccagaagc tatggacaat gatctcaatt gctgcaatcc aacttgctgc 13440
agctagatcg cattgtcgtg ttgcctgtat ggtacagggt gataatcaag taatagcagt 13500
aacgagagag gtaagatcag atgactctcc ggagatggtg ttgacacagt tgcatcaagc 13560
cagtgataat ttcttcaagg aattaatcca tgtcaatcat ttgattggcc ataatttgaa 13620
ggatcgtgaa accatcaggt cagacacatt cttcatatac agcaaacgaa tcttcaaaga 13680
tggagcaatc ctcagtcaag tcctcaaaaa ttcatctaaa ttagtgctag tgtcaggtga 13740
tctcagtgaa aacactgtaa tgtcctgtgc caacattgcc tctactgtag cacggctatg 13800
cgagaacggg cttcccaaag acttctgtta ctatttaaac tatataatga gttgtgtgca 13860
gacatacttt gactctgagt tctccatcac caacaattcg caccccgatc ttaatcagtc 13920
gtggattgag gacatctctt ttgtgcactc atatgttctg actcctgccc aattaggggg 13980
actgagtaac cttcaatact caaggctcta cactagaaat atcggtgacc cggggactac 14040
tgcttttgca gagatcaagc gactagaagc agtgggatta ctgagtccta acattatgac 14100
taatatctta actaggccgc ctgggaatgg agattgggcc agtctgtgca acgacccata 14160
ctctttcaat tttgagactg ttgcaagccc aaatattgtt cttaagaaac atacgcaaag 14220
agtcctattt gaaacttgtt caaatccctt attgtctgga gtgcacacag aggataatga 14280
ggcagaagag aaggcattgg ctgaattctt gcttaatcaa gaggtgattc atccccgcgt 14340
tgcgcatgcc atcatggagg caagctctgt aggtaggaga aagcaaattc aagggcttgt 14400
tgacacaaca aacaccgtaa ttaagattgc gcttactagg aggccattag gcatcaagag 14460
gctgatgcgg atagtcaatt attctagcat gcatgcaatg ctgtttagag acgatgtttt 14520
ttcctccagt agatccaacc accccttagt ctcttctaat atgtgttctc tgacactggc 14580
agactatgca cggaatagaa gctggtcacc tttgacggga ggcaggaaaa tactgggtgt 14640
atctaatcct gatacgatag aactcgtaga gggtgagatt cttagtgtaa gcggagggtg 14700

-continued

```
tacaagatgt gacagcggag atgaacaatt tacttggttc catcttccaa gcaatataga  14760
attgaccgat gacaccagca agaatcctcc gatgagggta ccatatctcg ggtcaaagac  14820
acaggagagg agagctgcct cacttgcaaa aatagctcat atgtcgccac atgtaaaggc  14880
tgccctaagg gcatcatccg tgttgatctg ggcttatggg gataatgaag taaattggac  14940
tgctgctctt acgattgcaa aatctcggtg caatgtaaac ttagagtatc ttcggttact  15000
gtccccttta cccacggctg ggaatcttca acatagacta gatgatggta taactcagat  15060
gacattcacc cctgcatctc tctacagggt gtcaccttac attcacatat ccaatgattc  15120
tcaaaggctg ttcactgaag aaggagtcaa agaggggaat gtggtttacc aacagatcat  15180
gctcttgggt ttatctctaa tcgaatcgat ctttccaatg acaacaacca ggacatatga  15240
tgagatcaca ctgcacctac atagtaaatt tagttgctgt atcagagaag cacctgttgc  15300
ggttcctttc gagctacttg gggtggtacc ggaactgagg acagtgacct caaataagtt  15360
tatgtatgat cctagccctg tatcggaggg agactttgcg agacttgact tagctatctt  15420
caagagttat gagcttaatc tggagtcata tcccacgata gagctaatga acattctttc  15480
aatatccagc gggaagttga ttggccagtc tgtggtttct tatgatgaag atacctccat  15540
aaagaatgat gccataatag tgtatgacaa tacccgaaat tggatcagtg aagctcagaa  15600
ttcagatgtg gtccgcctat ttgaatatgc agcacttgaa gtgctcctcg actgttctta  15660
ccaactctat tacctgagag taagaggcct agacaatatt gtcttatata tgggtgattt  15720
atacaagaat atgccaggaa ttctactttc caacattgca gctacaatat ctcatcctgt  15780
cattcattca aggttacatg cagtgggcct ggtcaaccat gacggatcac accaacttgc  15840
agatacggat tttatcgaaa tgtctgcaaa actgttagta tcttgcaccc gacgtgtgat  15900
ctccggctta tattcaggaa ataagtatga tctgctgttc ccatctgtct tagatgataa  15960
cctgaatgag aagatgcttc agctgatatc ccggttatgc tgtctgtaca cggtactctt  16020
tgctacaaca agagaaatcc cgaaaataag aggcttaact gcagaagaga aatgttcaat  16080
actcactgag tatttactgt cggatgctgt gaaaccatta cttagccccg atcaagtgag  16140
ctctatcatg tctcctaaca taattacatt cccagctaat ctgtactaca tgtctcggaa  16200
gagcctcaat ttgatcaggg aaagggagga cagggatact atcctggcgt tgttgttccc  16260
ccaagagcca ttattagagt tcccttctgt gcaagatatt ggtgctcgag tgaaagatcc  16320
attcacccga caacctgcgg catttttgca agagttagat ttgagtgctc cagcaaggta  16380
tgacgcattc acacttagtc agattcatcc tgaactcaca tctccaaatc cggaggaaga  16440
ctacttagta cgatacttgt tcagagggat agggactgca tcttcctctt ggtataaggc  16500
atcccatctc ctttctgtac ccgaggtaag atgtgcaaga cacgggaact ccttatactt  16560
ggctgaagga agcggagcca tcatgagtct tcttgaactg catgtaccac atgaaactat  16620
ctattacaat acgctctttt caaatgagat gaaccccccg caacgacatt tcgggccgac  16680
cccaactcag tttttgaatt cggttgttta taggaatcta caggcggagg taacatgcaa  16740
ggatggattt gtccaagagt tccgtccatt atggagagaa aatacagagg aaagtgacct  16800
gacctcagat aaagcagtgg ggtatattac atctgcagta ccctacagat ctgtatcatt  16860
gctgcattgt gacattgaaa ttcctccagg gtccaatcaa agcttactag atcaactagc  16920
tatcaattta tctctgattg ccatgcattc tgtaagggag ggcggggtag taatcatcaa  16980
agtgttgtat gcaatgggat actactttca tctactcatg aacttgtttg ctccgtgttc  17040
cacaaaagga tatattctct ctaatggtta tgcatgtcga ggggatatgg agtgttacct  17100
```

ggtatttgtc atgggttacc tgggcgggcc tacatttgta catgaggtgg tgaggatggc 17160
aaaaactctg gtgcagcggc acggtacgct tttgtctaaa tcagatgaga tcacactgac 17220
caggttattc acctcacagc ggcagcgtgt gacagacatc ctatccagtc ctttaccaag 17280
attaataaag tacttgagga agaatattga cactgcgctg attgaagccg gggacagcc 17340 cgtccgtcca ttctgtgcgg agagtctggt gagcacgcta gcgaacataa ctcagataac 17400
ccagatcatc gctagccaca ttgacacagt tatccggtct gtgatatata tggaagctga 17460
gggtgatctc gctgacacag tatttctatt taccccttac aatctctcta ctgacgggaa 17520
aaagaggaca tcacttaaac agtgcacgag acagatccta gaggttacaa tactaggtct 17580
tagagtcgaa aatctcaata aaataggcga tataatcagc ctagtgctta aaggcatgat 17640
ctccatggag gaccttatcc cactaaggac atacttgaag catagtacct gccctaaata 17700
tttgaaggct gtcctaggta ttaccaaact caaagaaatg tttacagaca cttctgtact 17760
gtacttgact cgtgctcaac aaaaattcta catgaaaact ataggcaatg cagtcaaagg 17820
atattacagt aactgtgact cctaacgaaa atcacatatt aataggctcc tttttggcc 17880 aattgtattc ttgttgattt aattatatta tgttagaaaa aagttgaact ctgactcctt 17940
aggactcgaa ttcgaactca aataaatgtc tttaaaaaag gttgcgcaca attattcttg 18000
agtgtagtct cgtcattcac caaatctttg tttggt 18036

<210> SEQ ID NO 15
<211> LENGTH: 18036
<212> TYPE: RNA
<213> ORGANISM: Artificial Sequence
<220> FEATURE:
<223> OTHER INFORMATION: chimeric viral genome

<400> SEQUENCE: 15
ugguuuguuu cuaaaccacu uacugcucug augugaguuc uuauuaacac gcguuggaaa 60
aaauuucugu aaauaaacuc aagcuuaagc ucaggauucc ucagucucaa guugaaaaaa 120
gauuguauua uauuaauuua guuguucuua uguuaaccgg uuuuuuccuc ggauaauuau 180
acacuaaaag caauccucag ugucaaugac auuauaggaa acugacguaa cggauaucaa 240
aaguacaucu uaaaaacaac ucgugcucag uucaugucau gucuucacag acauuuguaa 300
agaaacucaa accauuaugg auccugucgg aaguuuauaa aucccgucca ugauacgaag 360
uucauacagg aaucacccua uuccaggagg uaccucuagu acggaaauuc gugauccgac 420
uaauauagcg gauaaaauaa cucuaaaagc ugagauucug gaucauaaca uuggagaucc 480
uagacagagc acgugacaaa uucacuacag gagaaaaagg gcagucaucu cucuaacauu 540
ccccauuuau cuuuaugaca cagucgcucu agugggaguc gaagguauau auagugucug 600
gccuauugac acaguuacac cgaucgcuac uagacccaau agacucaaua caagcgaucg 660
cacgaguggu cugagaggcg ugucuuaccu gccugcccga cagggggccg aaguuagucg 720
cgucacaguu auaagaagga guucaugaaa uaauuagaac cauuuccuga ccuauccuac 780
agacagugug cgacggcgac acuccacuua uuggaccagu cacacuagag uagacuaaau 840
cuguuuucgc auggcacggc gacguggucu caaaaacggu aggaguggug gaguacaugu 900
uuacauccgg gcggguccau uggguacugu uuauggucca uugugaggua uaggggagcu 960
guacguauug guaaucucuc uuauauagga aaacaccuug ugccucguuu guucaaguac 1020
ucaucuacuu ucaucauagg guaacguaug uugugaaacu acuaaugaug gggcgggagg 1080

-continued

```
gaaugucuua cguaccguua gucucuauuu aacuaucgau caacuagauc auucgaaacu   1140
aaccugggac cuccuuaaag uuacaguguu acgucguuac uaugucuaga caucccauga   1200
cgucuacauu auauggggug acgaaauaga cuccagucca gugaaaggag acauaaaaga   1260
gagguauuac cugccuugag aaccuguuua gguaggaacg uacaauggag gcggacaucu   1320
aaggauauuu guuggcuuaa guuuuugacu caacccccagc cgggcuuuac agcaacgccc  1380
cccaaguaga guaaacuuuu cucgcauaac auuaucuauc aaaguacacc auguacguca   1440
aguucuucug aguacuaccg aggcgaagga agucgguuca uauuccucaa gggcacagaa   1500
cguguagaau ggagcccaug ucuuuccucu acccuacgga auaugguucu ccuucuacgu   1560
cagggauagg gagacuuguu cauagcauga uucaucagaa ggaggccuaa accucuacac   1620
ucaaguccua cuuagacuga uucacacuua cgcaguaugg aacgaccucg ugaguuuaga   1680
uugagaacgu uuuuacggcg uccaacagcc cacuuaccua gaaagugagc ucgugguuau   1740
agaacguguc uucccuugag auuauuaccg agaacccccu uguuguugcg guccuaucau   1800
agggacagga gggaaaggga cuaguuuaac uccgagaagg cucuguacau caugucuaau   1860
cgacccuuac auuaauacaa uccucuguac uaucucgagu gaacuagccc cgauucauua   1920
ccaaaguguc guaggcuguc auuuaugagu cacucauaac uuguaaagag aagacgucaa   1980
uucggagaau aaaagcccua aagagaacaa caucguuucu cauggcacau gucugucgua   2040
uuggcccuau agucgacuuc guagaagagu aaguccaaua guagauucug ucuacccuug   2100
ucgucuagua ugaauaaagg acuuauauuc ggccucuagu gugcagccca cguucuauga   2160
uugucaaaac gucuguaaag cuauuuuagg cauagacguu caaccacacu aggcaguacc   2220
aacugguccg ggugacguac auuggaacuu acuuacuguc cuacucuaua acaucgacgu   2280
uacaaccuuu caucuuaagg accguauaag aacauauuua gugguauau auucuguuau    2340
aacagauccg gagaaugaga guccauuauc ucaaccauuc uugucagcuc cucgugaagu   2400
ucacgacgua uaaguuuauc cgccuggugu agacuuaaga cucgaaguga cuagguuaaa   2460
gcccauaaca guaugugaua auaccguagu aagaaauacc uccauagaag uaguauucuu   2520
uggugucuga ccgguuaguu gaagggcgac cuauaacuuu cuuacaagua aucgagauag   2580
cacccuauac ugaggucuaa uucgaguauu gagaacuucu aucgauucag uucagagcgu   2640
uucagaggga ggcuaugucc cgauccuagu auguauuuga auaaacucca gugacaggag   2700
ucaaggccau gguggggguuc aucgagcuuu ccuuggcguu guccacgaag agacuauguc  2760
guugauuuaa augauacauc cacgucacac uagaguagua uacaggacca acaacaguaa   2820
ccuuucuagc uaagcuaauc ucuauuuggg uucucguacu agacaaccau uuggugauag   2880
gggagaaacu gaggaagaag ucacuugucg gaaacucuua guaaccuaua cacuuacauu   2940
ccacuguggg acaucucucu acguccccac uuacaguaga cucaauaugg uaguagauca   3000
gauacaacuu cuaagggucg gcacccauuu ccccugucau uggcuucuau gagauucaaa   3060
uguaacgugg cucuaaaacg uuagcauucu cgucgucagg uuaaaugaag uaauaggggu   3120
auucgggucu aguugugccu acuacgggaa ucccgucgga aauguacacc gcuguauacu   3180
cgauaaaaac guucacuccg ucgagaggag aggacacaga aacugggcuc uauaccaugg   3240
gaguagccuc cuaagaacga ccacaguagc caguuaagau auaacgaacc uucuaccuug   3300
guucauuuaa caaguagagg cgacagugua gaacaugugg gaggcgaaug ugauucuuag   3360
agugggagau gcucaagaua gcauaguccu aaucuaugug ggucauaaaa ggacggaggg   3420
caguuuccac uggucgaaga uaaggcacgu aucagacggu cacagucucu uguguauaau   3480
```

cuucucugau uccccaccaa ccuagaugac cuccuuuuuu guagcagaga uuugucguaa 3540
cguacguacg aucuuauuaa cugauaggcg uagucggaga acuacggauu accggaggau 3600
cauucgcguu agaauuaaug ccacaaacaa cacaguuguu cgggaacuua aacgaaagag 3660
gauggauguc ucgaacggag guacuaccgu acgcguugcg ccccuacuua guggagaacu 3720
aauucguucu uaagucgguu acggaagaga agacggagua auaggagaca cacgugaggu 3780
cuguuauucc cuaaacuugu ucaaaguuua uccugagaaa cgcauacaaa gaauucuugu 3840
uauaaacccg aacguuguca gaguuuuaac uuucucauac ccagcaacgu gucugaccgg 3900
guuagaggua aggguccgcc ggaucaauuc uauaaucagu auuacaaucc ugagucauua 3960
gggugacgaa gaucagcgaa cuagagacgu uuucgucauc aggggcccag uggcuauaaa 4020
gaucacaucu cggaacucau aacuuccaau gagucagggg gauuaacccg uccucagucu 4080
uguauacuca cguguuuucu cuacaggagu uaggugcuga cuaauucuag ccccacgcuu 4140
aacaaccacu accucuugag ucucaguuuc auacagacgu guguugagua auauaucaaa 4200
uuuaucauug ucuucagaaa cccuucgggc aagagcguau cggcacgaug ucaucuccgu 4260
uacaaccgug uccuguaaug ucacaaaagu gacucuagug gacugugauc gugauuaaau 4320
cuacuuaaaa acuccugaac ugacuccuaa cgagguagaa acuucuaagc aaacgacaua 4380
uacuucuuac acagacugga cuaccaaagu gcuaggaagu uuaauaccgg uuaguuuacu 4440
aacuguaccu aauuaaggaa cuucuuuaau agugaccgaa cuacguugac acaguugugg 4500
uagaggccuc ucaguagacu agaauggaga gagcaaugac gauaaugaac uaauaguggg 4560
acaugguaug uccguugugc uguuacgcua gaucgacguc guucaaccua acgucguuaa 4620
cucuaguaac agguaucgaa gaccguauua ggaagcuaug ggggagaccg ugacuguuau 4680
auauacagua guaaucccug agaacucucc agugucaguc aucccaguga accuccuaac 4740
uuucccagag gaugcuugua gcaucacagg uagucagaau ccacuuaggu gagcuucuuu 4800
acuccauccg gguaguugac uaacuaccgu acucgcuugu uaaacuagca gacuauagag 4860
guuaauucug ucaugaaaac guccagucaa caauacuucc aacguugaga ggcugccaag 4920
aacgaaaagc cuaguacuaa cgccaaacuu cuaugagaaa gaaaugucag ucacuaugca 4980
aagaauaacg acaauuuucu gucaacugag uagcgaucgu augagaacca guuccuauac 5040
gauaggacuu acugagguaa agggacuuuc uuuccacguu agacuagccg auccuaggga 5100
aggcgguagu ggacugucaa ggaauugaag aaacagucga aucgcuucua ggcagguaau 5160
ugaaagugaa ggaagaggaa cucgcucaua cuaugacggu guaacaguag agauuccaug 5220
aguucccagc agucuauaag guagagaaau auaccuaguu uuaguaaacu gagauuuuug 5280
agauaguucu ccgcuaauca gcuucaacga agaaaaugua caaagaagac cagaagccuc 5340
ucuuccaagg cggauuugcu ccguucgguu aauagcaacc ccacacgcua acggaacaga 5400
aaauccuugu acgaguccaa ccacuguccc aguauaagau auguaccgag uuuaaguuca 5460
cgucuauuug agaauaugag agaguuguac uauagcacac uuuagagacg acuuagacgu 5520
acaucaacgg guuacuggaa ggguauauaa cauaggugaa acugagcgcc ggugugugga 5580
cguaagaaga aagacauggg caacuacuaa caagggaacu ucuuucuguc auggacuucc 5640
uaguauaguu ucagauggua aaagccacgc guguaaaccg aggacugacg gaaacgacgu 5700
uaugcccuga guucgucacc cacuggggug ucugcguugu cuguguugua gagucgacga 5760
acuaagacaa gauuuggucu cuuaugucau cgcuaacgua cucagugccu aagacgauau 5820

-continued

```
aguaacccu ccuccgguua aucuuacaga aauucgagga cguccaacuu acgcuucuuu   5880
agaggacguu uacauggacu gccgagcuca ucgaccuguc gaggcauacg uuuagggagg   5940
uaaucacuau guuguagcau cugaacuaau ggguucagaa aacggucucg cagauaauug   6000
gcguuuuaca guaguuaaaa gagacuauuc gaagacucua cguggcggca ccaacuauaa   6060
uacaacuggu auagagacgg gagguaguau agacguaugu aguuauguuc aaggacccau   6120
ucuguacacu ugaacaagag uaagcauacg caguguugcu guucaagucc ucacuguuuc   6180
ugaaccggau ggaauaccca aucguagugg uuaaacaacc ggcgucugga acaggaucga   6240
cggugguagu cuacggagac cuagacaaaa uauaccucgg uacguuugaa ccgacaccug   6300
guaaaacuca cuuuggucuu acggccuagg caugcuuacg acgacuugag gagacuggcc   6360
cccuguaaca aucugguucu acuggggucg ucaaagaaga gauauacgca ugugucggaa   6420
cacuugucaa gagguauaga gcacaacacu uaaaccuaga agaagaguua gaaggcuuua   6480
aacaaccaac uuagacccug gaguuauaau cggucaagaa gauuugugga ccccaccucg   6540
ugaggccaau aagaccuuaa caccaauucu caaaccacau gacgggaagg cucaagauag   6600
uaagagaguc auaguccucu ccggcuaagu ucauaaaaaa agguaacagc cgacucuuac   6660
uccaccagcu ucaguguaag uaguccuucg ccaucggguc aauuaaaggu cauuaucuca   6720
ucaaacacga acugguuacc acuucugucc acacugagac cauccuauua gacuacgaga   6780
cgggaaaguc cuggccucga gcgguacaag augggcauaa uaaaugguac ucgacaaaac   6840
ggaacauaga guaacgguga auguaaaaaa gaauuaguuc ucugauaacu guuccgaauu   6900
agacuagcgu acucgugacc gacuaacacc aguugaccgu uguaccuuaa gcucgugcgc   6960
ggccguaagc caaacuaaga acuacagcgu cuucuaucca cuauguuacg guagaaaggu   7020
ugaggaaaua uuaacugagu ugaucggucu ggaccgaaga gauuggggca guagaaacuc   7080
cuagaguuga ucauugcccu gcuaagacuu aagaggcuuc ucucauaauc uauaaagucg   7140
uuacgacucu guuauccaga auaaucagaa cuggugaaau uuuguucaac uacaacacau   7200
acgacgaaac caugacgaac uugagugagc ucauuacgcu gacgcccuac acgauagcuu   7260
augacgucug cgucccaauu cagaacgaac augugguagu ucguaacagg gcuuaugggg   7320
agcguuccac accaaagaua ucuucuaauc cccuacaccu agacauaucu gaggucauug   7380
ugugcccaac cccguagaac gacuucggac cguucccuau gauggaccgg cucacuuccg   7440
uaacuuacau auuccugaua cuucucaccg acaaaacaac gacugacagu auccuauauu   7500
auugcgcccu cucuucauac uacugggagc aacuauguuc uuuacucuac agggaugaca   7560
cucuuaagac ggaagccggg gguacucaca cugacacaac ccgccauguc agucauggcc   7620
cagaagcgga uuccuacaac uguggaacua ucuauucuau cggacgacau acgcaaaggg   7680
ugguuuggca gguccgaaua ugcuucugga ccgguaagcu uagaccauca gaacgaguag   7740
acccguacac aguaacauag cgaacauaua guguauaaag ggaaggacau gucacaguga   7800
cccacuuaac ccaaaauugg gaggcaucug acucuuggua ugcgccgaca guuauuuucu   7860
agguggggga ugaggaccca ucaaccggug ggucaggggc uuauuacaac acuguagauc   7920
caggaaaagc accaugaccg gcagcuuggg auuggagggu acaugguagg cgcaucccug   7980
ucgacucaau auuagaagaa ggagacagag gcacugaaag cucgugucgu auaguguugg   8040
guccccucaa cgugagugug acguucugaa ggcuaaaacc cacagcaggu ccaacuaccu   8100
ugcgucucau cuuuucuuau gggagggaca acgucuacag gccucgugug guucacgauu   8160
uaugacuaua cuuacacuca cuagagacgu aggucuguua uaauguaaua cccacaucgu   8220
```

-continued

```
cauuacccau cgugaguaca guuuacuccc auaagcucac guuggacuag gacaucaucc   8280
gcggcccuau uuuaagucua caagaacuuu acgucucccu aucuuacuac acuguaguga   8340
ucguaguaga uguuacucaa gaaacggaua ggggggauau auuagaccca guaccuauuc   8400
acggggggug ggugacaaca aacgucgagg uaauuagacu auucucucuc uacaauaacg   8460
caaguauuaa caccagaguc aaaaauuguu acgguugccu cugaguuccc ggugaacgaa   8520
uauauaggau agaugaugua gaacuaaccu ugguucacau cuacauuaga aaagaagacg   8580
ggaccuuaag gaucagccau acggauguuc uagcgaucca cacgaucggg gguacgauau   8640
auuuucccuc cgaugucuau aucgguucca gugaugacaa uucuuauucu aacguuaggc   8700
cuuauaguuc gcgguacaua aaaaacggag agaaaguagu aagagauugc guugaaccga   8760
uugccgcgcc agguacuaac uccugacaac agccacuucg ccaucuugcc uccaacacuu   8820
cggaccgagc guuaacuccc cgccggagag aauggcaaga ugggcauaua gcaggaaacc   8880
aguagauguu ggccaucaaa aaagaauuga gagacuugac ugucugaugg ucuugaaagu   8940
guguuuaaug auaaucccuu uggaagcaag gaguagacac aaguguaaaa acaucaccga   9000
gaguagacua gaucucauaa uaaggguucg guauuauucc agaaaacaac gcggaaaacg   9060
aacauguaau ccaucguacg aucuuagucc gauucauaug guuuuuguuc ucuauacuau   9120
caguuuugcu auauccauua cucucgucua cacgaucagu caaacuguaa cugaaacaga   9180
ucaaaagaca acgaaaggag auugaauaag uuucguaaug acuagcucaa caacuguaag   9240
gguucgaguc aacucuauag uucuaacgga caauaauaau gaacucuuag aacauaacuc   9300
uauaagaaga cuauucaaug uagcuuaagg ggugacucgg aauuucaaua gggcggauuc   9360
cuauuuugua acguacuaac aaauagauaa ucucugugcc gaagagguau caaaacgcua   9420
uacuaugggc cccccaaaug uguagaugua caacaguaga acgucaaccg cuacugacuu   9480
ggaaacuauc aguacauacc acaucauuca cgcggaagcc agaaacucau guauguccgg   9540
cugcauaacg gcgaguucgu ccuuauuuau gguccccugu aucccuugca augauaagaa   9600
cauguuauau uuagauucag ucaaagauau gucauacucc acaguucaag aagauagugu   9660
cuuggcugga cacagguggug aaaccccugu ucacggcucc guuuaggggga ccaacacgaa   9720
ugccuauucc aaagguucau ccaccgugcg uauaauaaau ccaagggcug acuuccaucu   9780
caaugggcau augggguucuc aacucagaca cucagcauau cuuaucccaa uggccacuaa   9840
uucggcgaug gcuaauuacu cgacucaacu aacaagggau guggauugaa ucaguuauuc   9900
auuagguaua aagguggucg aucuaacauu ucacggacuu aucagucgaa caaauuucgu   9960
ccacuucacu aaacaccagg cuuaugacau caguuaagcc aauccauguc caacucgaga  10020
ugugguugaa cgacacguua aaacuacguc agauuaagga cucgacaaaa uaauucaacc  10080
aguaauuguu ugacgacgua gaaggguuga cggugacgau caacgcuauu aggcagucac  10140
uggaguacgu gucggaguaa ccaacgccgu uacgagagaa auucagccuc cuacaaccgu  10200
cguaaaacaa accgaacaua gucucgacgc cggcgacaau aaacacgccg ucaacguugg  10260
gguucucggu guggcgguua uuaccgcgga uauuccgcgg ggacagaggg gggagggucua  10320
caucaguguc ugagaacaua ggaugccuau cucagugguu ccccccacuc guuucaccag  10380
uuacaggaca acauacguag guucccccga aagcguguac ggaggaauag gaacccgucu  10440
aagcccuccu cgaauugaua cuaacuagga cagacccuac uccacauaua caacugccga  10500
aacagaggac auugguguua aggacgucga cguucuccgg acgguaguua ccucaaacgg  10560
```

```
ccugucuacg uugagucaug gucgcguugg gccuaucagu cguaguaucc acgacccaag  10620
aaccaucuuc cagaccucgg guagaacgug gaccuccccgc gguuggcccu aggucuuaga  10680
agaugggcac aaaaaagauu gaacuaucug uccaauugau ugacauuuau uaguucuguc  10740
uaaucaaaaa acacaguacu acuagaccca cucacccgcc ucgcguuaga gucucugcgu  10800
cgaauaaaga auuuuccuaa cauaaaccgu ucccacacgg ggaagagguc gaaucaucuc  10860
cauuggagca ccagccgcca gugacgcugu cgcgcaaccc auggacgaac cuauuacuaa  10920
aauugcgagg cguccgugcg ccaaacugag gucucauaga accgguggac uccucuucgu  10980
aaacgauacc cuaucguccg acagggugac gaucucuucu uuccacgguu uucgaaucag  11040
gcacguggag aacgaaaaug guugugccuu ccgggcucgu guagugacuc gggcugucua  11100
ucuaguuccg aggaauaaaa gaaaaggucg aacaguuuac agugaaagaa ggggaaggau  11160
agaugccacc aguauucagg uuauacguuc uucuccaauc guaucauagg cgacagucug  11220
aaucugucuc uaaauugguu uccugaggag cccagaugga gguguaauua ucacuguaac  11280
ucgcguucua acaugucuga gcucggucuu uggaaguuau gacgucgucc cuagaacauc  11340
uguaggaaga agccauggug ucaguuccuc uguuucaagu ggaacauaag aucccaaggu  11400
gagggcccuu agaagagacc gcgaaagugc acgaacugac guaagugacu acucauaaac  11460
aaacggugu u gggaugucga aacgucguga accccacgga cgugaugacu cuuuugguaa  11520
gagagucgua aucaacguga gaagaacgua cacugauagu aucacucugu ccgggaacgg  11580
ucgaguuauu ccagaggcca uaaacccugc gaaggauccg ucucguagcg ucgccuuuca  11640
uugagcgcga acccaaauag uagcuaguac ggcugucacc gaagaaguaa ggguugaacu  11700
uucuacuuag guauccacca cuacuuauga cucaggagga augauaguca gguguucagu  11760
uccgcgaccu aggauauaac gccccgcuaa acgaagaagg guagaggaca cagaacaucc  11820
ugcuagccuu uacgauuguc caacgaucuu cuuacccguc uuaguuucau gucggguuaa  11880
caggaucuac ucagguagaa ccguguuaac cccgugaggu uaagaugggc auaaaaaaga  11940
auuaggaauu acaucgaucu aauuaaugcc aaugcgcuag uaagucaccc cgacuccuuc  12000
gcucucucca uugcuaauca aaaaacacag uacuacuaga cccacucacc ccgaaucaug  12060
ugccaucaau gugugucgaa uaagcagaag cgaaagaaga cgggugcuuc ccauaagcuc  12120
guccccccauc aguagaagga accaagcccc aaaagacgcu uuauccaaag aguauaaaaa  12180
ucguuuucgu cuuuuggcgc gaaagacaga agcucgaaag acaaguagga acacaucuuc  12240
gaguuccgga aagucuugag accaccguuc auaggacagc aggaguagug auaggaggag  12300
uuggaggagu aggaacauca uugcagaucu cccagcaccu ccucaaggcc ggcccccuug  12360
acgcggaccc uugucuugga cuugacccaa acuaaagucc aaguaaugua uaaacuugcg  12420
gucgucagga uuuuauuacg aguggugug gcgauagggu uaaggcucac gccgcuugcc  12480
caaucuuucu uuacuccgcu acggucuaug acaucuuuaa ugacgacggc gccgacagua  12540
gugaugucaa ggguuacgga aaggaugaag agguucucac aacgguuuuu uuagacgaua  12600
acgagauuuc uaacguagag gggauagagg ugcauaaugu cacaguuaca gagacuugga  12660
aaacaauauu uauaaaacua uagacuggug uaguaguauc aaauuucagg gucauagaga  12720
cucaaggagc gcucacauau gaagcugccc guguuucagg uuuagaagau cauaucaccg  12780
caaguucaac uacuuacacg agugaagaag cuagagccuu cguaaaugaa cagauuguuu  12840
acauaucaga agcauuucuu ccaucaaaag aggguugucu uucauggcag acacuaacua  12900
guacguacca agauaguuua aggcgggaac auuuuaaagu aauacaagag gcucaaccgg  12960
```

-continued

```
auuauacagu ucuaacacca aaagacaacu caagcgucuu uugacacuga guccccuccu  13020
gcuuauggac uuuuauucau gaccagacca uaucguguac caacccaggg gaccguacgc  13080
guaccuuagg acguaggauu auaaaagcua accuuaaaga uauguaaaac uauggcgaug  13140
cuacagaggg uuaucggacc gcgaaugucc aacaggcuug uuucuacagu agucacucaa  13200
gcccaaauca aagaaguaga guacgguaug uuagucaacc gccaagacuu cgagugugu  13260
gcgaagguug uuuaaaggcu auucgagcaa uuguacccga accuaaaaca gcauacguuu  13320
aacauuguac cguuuacaac gucuugacac ccaucauuaa gauaguggga cuccaggucu  13380
gacgucgcug cggcacgccg cuggacgccg aaccgcugcg agagagggag agcccucuac  13440
uaaaacagaa acacggagaa gauccaugua aagucgguuc gguaccgagu acucaaagac  13500
uuuacgcuag ucuuuaggcg gugauggcuc uaucauaagc uacaggggguc uugccuguac  13560
ucagcuugau augaaagacc guuucuacgg uagauaccgg aggcuccgau accauccuug  13620
cguaagucgg uuuacuucgg acgacuacaa uuuuccaaca aaaggccugc ucuugcagua  13680
ucaguauaga aauucacuuu ucaccauuga caaaaacaug cuuugugcuu gacgaaggcc  13740
cugaaguuag guaaaugacu cucauguaug ucuaaggaaa agaagguaac guagggucgg  13800
auaucacuua acaaguagac aaucuuucaa agaaaaaaau cccccagaau aaacaggcca  13860
aagguuuagg gacugaacua uuaaacgcua aagcucuuua gauaucagag acaucuguga  13920
cacugcggaa ccaggccagc acaaaaacca uauuuuuccu cuuuaaagau gacauagugg  13980
acagcgguaa gguuucauua guaugcccau augucuagau cggacaucua uaaggugug  14040
ugucagcugg cuacaucugc aagccauagg gucccaaacu acagcgaauc auuucaauca  14100
acauacuuug cggaaccucu gucaacuaga auugucacua ccuuggucc cguuaaaaaa  14160
aagacgaagu aguaacagca uucgaaguuu uuuguacuuu aaaaauacua ugcaacgaaa  14220
ccuacucgua agagggcuag cuaguuagga cuguuaaagu acuaucagau aaccuuggga  14280
ccagugcaug aguaaacaau aaaccccaga acucuuauua cgggugcauc auugacacca  14340
auauacaaau aucauaucuc aguguaauuu cugcaugccc cguuacaaaa cgaacuucug  14400
augccguuaa ggaagucagu acaaucagcu uagccguaca gccacuguua cagcaccgac  14460
ccguucggag cguugugacc gcggucaacc ucuacucgug cguuuuuaag acaaagauua  14520
gaccccaaga aagccacggg ggcuggguua ccgaagccuc uuucucuaaa aagguuguag  14580
guacgaccga cauagugcuc ccagauaaua aggucguuaa ggcacacuua gaacucuauc  14640
ccaucuaccc uaguccuaac ggugcgugug cgucuagucg uaaaaguucg aucgguacag  14700
uuacaagugc cgcuacaucc uaacguacca ccgauguuga uaguugauuu gaguguuaac  14760
cccgugaggu uaagaugggc auaaaaaaga auuaggaauu acaucgaucu aauuaaugcc  14820
aaugcgcuag uaagucaccc cgacuucuuc gcucucuccu aacggcgaac cucucaaccu  14880
ggaacccaga cgcccccccu ugagccacgu cuaaggcaca cuacggcuca ccugucccug  14940
ggcgaugcac accgucauca uuaaucggua aaucucguuc cgcgaacuaa aaggacuaaa  15000
ggagcuagcu gggccgacgu agauugaacg aauccucgaa ccgacuucuu gagcccacgu  15060
aacccgcacu guacuaguua cgugccuguc acaggaaaag gugaggauau aguccgggcg  15120
uacgucaccg cccaaauuag uuaagucuac cuacaccgug accaacgcuu ucaaauaauu  15180
cacgguaaag cggaggaaca caguguaucc cucuccccag agguccccgga cuuugauuuu  15240
ggcccacucu agcccguuga cgggcaucua gugagucucu acuuuacaac cguguuggcc  15300
```

cuaggucuua gaaguaguaa ggguucaacc gaagguacug acguugucua caaaagucga 15360
caaccuaaag ccuggcguag uaucccuacc uccuacagac aaaguucugu ucuagaucga 15420
cuaucagcug gaaugaauga gagacacuau agcggaggua guaucuguag uagcgaacgu 15480
guuucagaug uccaccgacc uguacuaggc gucuauguuc ccauaacaga accgagacgg 15540
aacuagccuc ucguacuccc caacgugguc gacuaucaac acugaggagg guaacaggua 15600
cuauacgaca caagugcaga cacgggacca aagguccccg ccggaacuga accaagacgc 15660
cagaaaggac ugacaaaggc gcugacccaa cugaggggac gacaacucag ccugcaacca 15720
cuaaggggag aacccccgag cugguacccg ggaaaaaucg uaaccugcua aauaacgacu 15780
cgaacaguuc guaguugucg ucucucaacg aacgaggcca ggacucgaca cacagcugcc 15840
gaagcagaca ccggacccac cccccgacca gccgccuaca ccggccgccc gacaguacgc 15900
cccagcaaac gggcccacac cuaccaacaa acagucuaga caggacagcu agccccaacg 15960
gaacugaccg gccaccgacc uacgagggua cgaagagggu acgacgcgag ucguggaacc 16020
agaacggaac acccuaacgu gaggaagguu gucagagacg accaaauggg acccgacauu 16080
aauacaacag uuacugucaa ggugaacaga guuuaucgag cagcuagaga cguagacauu 16140
uccaccggua caaacaggac cagauagucc aucuccucuc ucgucucuga gcccucugaa 16200
cgggacuaga gacuuauagg gagaagaugg gcaugaaaaa agauuaaggg agccgagaca 16260
aaacuaacaa ucacucggcg uaacacggac accauagauc ccgcacgccu caacaugucg 16320
ucccccuccc uccuuucucc cccuacaaac aaacucccac accaguauau cucggcguuu 16380
agcuccccag cugaugccca cucccguaac ccuacaaaaa caccuucguc cgacccaaaa 16440
cagguaguua ugggggucag ccacagcaau agaacccuac cggguccuca acccccuccg 16500
gggcuaaccc cucacgggac acgucucaaa ccgcggaggg aguacgauaa acgauggcga 16560
gaguagucua gguccuuaac ccagaggggu aggggccgaa gaccaacggg aacgcuagau 16620
aagcuaggcg gaacaucucg aacccugggg gggagcgauu cgggucacuc cugaggcuga 16680
acaacucauc cguacagaua cgacgaccag aggagccucu gggcaacccg ucgucgacgg 16740
uccggggagg aacgacgacc ccaaucgaaa ucgagccguc gguauaggag caauuacgau 16800
gaagggacuc ggacucgcau gagaugaggu ucagaggucu uacuacacga guauuucagg 16860
gaccguuuaa ccauaaaggg ucauggaaau agauccugac uacgguaugg guaccguuuc 16920
cucauuucaa cacguaugag ccguccgcgu uucgaguaga ccagugauag ugguucauua 16980
caguacaugc cgcguaauag aggaaaguag gcuauguuug cguacucgac gaaguagaag 17040
accuacagcg gacucuccga ugauucacgu ucccgacuac agaaccacaa cuaaggcaug 17100
aacucacagu ucuucuuacg ucauucgggc cauaaggacu acauacucag augcagggga 17160
ugguccaaua uuauucaucu ccauggugga cggcacaacg ccggagagaa cucgagcgau 17220
ugguuuuucu acgccugacg uucucugaca gacuagcacu caaccuaaca cgaggacgua 17280
ugccccaucu ccuacauaaa gaaaaccugg gacggaacga cguauaugaa uaacuaagcg 17340
gaacaaaggc ugaguagacg ucagaguaug cgucaguacc gaaaacgaug acacugggua 17400
ugaacucgga ccuaucucuc cuaggagagg ucccauagcc acuacagaag accacguagu 17460
agaagccggg gccgacacug cuugccccaa ggcaacgacg uacgggcucc cucucuagga 17520
cgauaguagc guuuagagac acgagagaga agucugugag gugaggauaa caacuugacc 17580
ccgcacggca accguuucgg uaguuagagu ucgugccggu uacaccgaag uaagacaaag 17640
ggacguuccc guuguaccaa ggaguaaugg acacucaccc ucguauuuuc ucuauacucu 17700
cguggaacgg acucaccaaa caaccguaga agcgauuguc guuaggccuc cgucuuaugg 17760
uguuucgagg uagauagaag acccaguagu gacaauucuc acuuauggcc cugcagauga 17820
aaauuccaug agggaaaaag agggggaggu acucgaggua accccgcuca gacucggcgc 17880
uccucgacaa gcaugaguag uuuaugccuu cuguacaacc gucuuccgaa agagcucaaa 17940
cacgaagccc gagcgugagc ucuaagugug gaagaugggc acacugaagu uaacgagaaa 18000
gcggaaaaua gcgcugagug ccuaagagac aaacca 18036

<210> SEQ ID NO 16
<211> LENGTH: 19832
<212> TYPE: DNA
<213> ORGANISM: Artificial Sequence
<220> FEATURE:
<223> OTHER INFORMATION: plasmid

<400> SEQUENCE: 16
ggcgccggct gggcaacatt ccgaggggac cgtcccctcg gtaatggcga atgggacgcg 60
gccgatccgg ctgctaacaa agcccgaaag gaagctgagt tggctgctgc caccgctgag 120
caataactag cataacccct tggggcctct aaacgggtct tgaggggttt tttgctgaaa 180
ggaggaacta tatccggatc ggccgatccg gctgctaaca aagcccgaaa ggaagctgag 240
ttggctgctg ccaccgctga gcaataacta gcataacccc ttggggcctc taaacgggtc 300
ttgaggggtt ttttgctgaa aggaggaact atatccggat ggccgccacc ggtgggcctt 360
gcagcacatc ccccttcgc cagctggcgt aatagcgaag aggcccgcac cgatcgccct 420
tcccaacagt tgcgtagcct gaatggcgaa tgggacgcgc cctgtagcgg cgcattaagc 480
gcggcgggtg tggtggttac gcgcagcgtg accgctacac ttgccagcgc cctagcgccc 540
gctcctttcg ctttcttccc ttcctttctc gccacgttcg ccggctttcc ccgtcaagct 600
ctaaatcggg ggctcccttt agggttccga tttagtgctt tacggcacct cgaccccaaa 660
aaacttgatt agggtgatgg ttcacgtagt gggccatcgc cctgatagac ggtttttcgc 720
cctttgacgt tggagtccac gttctttaat agtggactct tgttccaaac tggaacaaca 780
ctcaacccta tctcggtcta ttcttttgat ttataaggga ttttgccgat ttcggcctat 840
tggttaaaaa atgagctgat ttaacaaaaa tttaacgcga attttaacaa aatattaacg 900
tttacaattt caggtggcac ttttcgggga aatgtgcgcg gaacccctat ttgtttattt 960
ttctaaatac attcaaatat gtatccgctc atgagacaat aaccctgata aatgcttcaa 1020
taatattgaa aaaggaagag tatgagtatt caacatttcc gtgtcgccct tattcccttt 1080
tttgcggcat tttgccttcc tgtttttgct cacccagaaa cgctggtgaa agtaaaagat 1140
gctgaagatc agttgggtgc acgagtgggt tacatcgaac tggatctcaa cagcggtaag 1200
atccttgaga gttttcgccc cgaagaacgt tttccaatga tgagcacttt taaagttctg 1260
ctatgtggcg cggtattatc ccgtattgac gccgggcaag agcaactcgg tcgccgcata 1320
cactattctc agaatgactt ggttgagtac tcaccagtca cagaaaagca tcttacggat 1380
ggcatgacag taagagaatt atgcagtgct gccataagca tgagtgataa cactgcggcc 1440
aacttacttc tgacaacgat cggaggaccg aaggagctaa ccgctttttt tcacaacatg 1500
ggggatcatg taactcgcct tgatcgttgg gaaccggagc tgaatgaagc cataccaaac 1560
gacgagcgtg acaccacgat gcctgtagca atggcaacaa cgttgcgcaa actattaact 1620
ggcgaactac ttactctagc ttcccggcaa caattaatag actggatgga ggcggataaa 1680

-continued

```
gttgcaggac cacttctgcg ctcggccctt ccggctggct ggtttattgc tgataaatct   1740
ggagccggtg agcgtgggtc tcgcggtatc attgcagcac tggggccaga tggtaagccc   1800
tcccgtatcg tagttatcta cacgacgggc agtcaggcaa ctatggatga acgaaataga   1860
cagatcgctg agataggtgc ctcactgatt aagcattggt aactgtcaga ccaagtttac   1920
tcatatatac tttagattga tttaaaactt catttttaat ttaaaaggat ctaggtgaag   1980
atcctttttg ataatctcat gaccaaaatc ccttaacgtg agttttcgtt ccactgagcg   2040
tcagaccccg tagaaaagat caaaggatct tcttgagatc ctttttttct gcgcgtaatc   2100
tgctgcttgc aaacaaaaaa accaccgcta ccagcggtgg tttgtttgcc ggatcaagag   2160
ctaccaactc tttttccgaa ggtaactggc ttcagcagag cgcagatacc aaatactgtc   2220
cttctagtgt agccgtagtt aggccaccac ttcaagaact ctgtagcacc gcctacatac   2280
ctcgctctgc taatcctgtt accagtggct gctgccagtg gcgataagtc gtgtcttacc   2340
gggttggact caagacgata gttaccggat aaggcgcagc ggtcgggctg aacggggggt   2400
tcgtgcacac agcccagctt ggagcgaacg acctacaccg aactgagata cctacagcgt   2460
gagcattgag aaagcgccac gcttcccgaa gggagaaagg cggacaggta tccggtaagc   2520
ggcagggtcg gaacaggaga gcgcacgagg gagcttccag ggggaaacgc ctggtatctt   2580
tatagtcctg tcgggtttcg ccacctctga cttgagcgtc gatttttgtg atgctcgtca   2640
ggggggcgga gcctatggaa aaacgccagc aacgcggcct ttttacggtt cctggccttt   2700
tgctggcctt ttgctcacat gttctttcct gcgttatccc ctgattctgt ggataaccgt   2760
attaccgcct ttgagtgagc tgataccgct cgccgcagcc gaacgaccga gcgcagcgag   2820
tcagtgagcg aggaagcgga agagcgccca atacgcaaac cgcctctccc cgcgcgttgg   2880
ccgattcatt aatgcagctg gcacgacagg tttcccgact ggaaagcggg cagtgagcgc   2940
aacgcaatta atgtgagtta cctcactcat taggcacccc aggctttaca ctttatgctt   3000
ccggctccta tgttgtgtgg aattgtgagc ggataacaat ttcacacagg aaacagctat   3060
gaccatgatt acgccaagct cggaagcggc cgctaatacg actcactata gggaccaaac   3120
agagaatccg tgagtcgcga taaaaggcga aagagcaatt gaagtcacac gggtagaagg   3180
tgtgaatctc gagtgcgagc ccgaagcaca aactcgagaa agccttctgc caacatgtct   3240
tccgtatttg atgagtacga acagctcctc gcggctcaga ctcgccccaa tggagctcat   3300
ggagggggag aaaaagggag taccttaaaa gtagacgtcc cggtattcac tcttaacagt   3360
gatgacccag aagatagatg gagctttgtg gtattctgcc tccggattgc tgttagcgaa   3420
gatgccaaca aaccactcag gcaaggtgct ctcatatctc ttttatgctc ccactcacag   3480
gtaatgagga accatgttgc ccttgcaggg aaacagaatg aagccacatt ggccgtgctt   3540
gagattgatg gctttgccaa cggcacgccc cagttcaaca ataggagtgg agtgtctgaa   3600
gagagagcac agagatttgc gatgatagca ggatctctcc ctcgggcatg cagcaacgga   3660
accccgttcg tcacagccgg ggccgaagat gatgcaccag aagacatcac cgataccctg   3720
gagaggatcc tctctatcca ggctcaagta tgggtcacag tagcaaaagc catgactgcg   3780
tatgagactg cagatgagtc ggaaacaagg cgaatcaata agtatatgca gcaaggcagg   3840
gtccaaaaga aatacatcct ctaccccgta tgcaggagca caatccaact cacgatcaga   3900
cagtctcttg cagtccgcat ctttttggtt agcgagctca agagaggccg caacacggca   3960
ggtggtacct ctacttatta taacctggta ggggacgtag actcatacat caggaatacc   4020
gggcttactg cattcttctt gacactcaag tacggaatca acaccaagac atcagccctt   4080
```

-continued

```
gcacttagta gcctctcagg cgacatccag aagatgaagc agctcatgcg tttgtatcgg   4140
atgaaaggag ataatgcgcc gtacatgaca ttacttggtg atagtgacca gatgagcttt   4200
gcgcctgccg agtatgcaca actttactcc tttgccatgg gtatggcatc agtcctagat   4260
aaaggtactg ggaaatacca atttgccagg gactttatga gcacatcatt ctggagactt   4320
ggagtagagt acgctcaggc tcagggaagt agcattaacg aggatatggc tgccgagcta   4380
aagctaaccc cagcagcaag gaggggcctg gcagctgctg cccaacgggt ctccgaggag   4440
accagcagca tagacatgcc tactcaacaa gtcggagtcc tcactgggct tagcgagggg   4500
gggtcccaag ctctacaagg cggatcgaat agatcgcaag ggcaaccaga agccggggat   4560
ggggagaccc aattcctgga tctgatgaga gcggtagcaa atagcatgag ggaggcgcca   4620
aactctgcac agggcactcc ccaatcgggg cctcccccaa ctcctgggcc atcccaagat   4680
aacgacaccg actgggggta ttgatggaca aaacccagcc tgcttccaca aaaacatccc   4740
aatgccctca cccgtagtcg acccctcgat ttgcggctct atatgaccac accctcaaac   4800
aaacatcccc ctctttcctc cctccccctg ctgtacaact ccgcacgccc tagataccac   4860
aggcacaatg cggctcacta acaatcaaaa cagagccgag ggaattagaa aaaagtacgg   4920
gtagaagagg gatattcaga gatcagggca agtctcccga gtctctgctc tctcctctac   4980
ctgatagacc aggacaaaca tggccacctt tacagatgca gagatcgacg agctatttga   5040
gacaagtgga actgtcattg acaacataat tacagcccag ggtaaaccag cagagactgt   5100
tggaaggagt gcaatcccac aaggcaagac caaggtgctg agcgcagcat gggagaagca   5160
tgggagcatc cagccaccgg ccagtcaagg caaccccgat cgacaggaca gatctgacaa   5220
acaaccatcc acacccgggc aaacgacccc gcatgacagc ccgccggcca catccgccga   5280
ccagcccccc acccaggcca cagacgaagc cgtcgacaca cagctcagga ccggagcaag   5340
caactctctg ctgttgatgc ttgacaagct cagcaataaa tcgtccaatg ctaaaaaggg   5400
cccatggtcg agcccccaag aggggaatca ccaacgtccg actcaacagc aggggagtca   5460
acccagtcgc ggaaacagtc aggaaagacc gcagaaccaa gtcaaggccg cccctggaaa   5520
ccagggcaca gacgtgaaca cagcatatca tggacaatgg gaggagtcac aactatcagc   5580
tggtgcaacc cctcatgctc tccgatcaag gcagagccaa gacaataccc ttgtatctgc   5640
ggatcatgtc cagccacctg tagactttgt gcaagcgatg atgtctatga tggaggcgat   5700
atcacagaga gtaagtaagg tcgactatca gctagatctt gtcttgaaac agacatcctc   5760
catccctatg atgcggtccg aaatccaaca gctgaaaaca tctgttgcag tcatggaagc   5820
caacttggga atgatgaaga ttctggatcc cggttgtgcc aacatttcat ctctgagtga   5880
tctacgggca gttgcccgat ctcacccggt tttagtttca ggccctggag acccctctcc   5940
ctatgtgaca caaggaggcg aaatggcact taataaactt tcgcaaccag tgccacatcc   6000
atctgaattg attaaacccg ccactgcatg cgggcctgat ataggagtgg aaaaggacac   6060
tgtccgtgca ttgatcatgt cacgcccaat gcacccgagt tcttcagcca agctcctaag   6120
caagttagat gcagccgggt cgatcgagga aatcaggaaa atcaagcgcc ttgctctaaa   6180
tggctaatta ctactgccac acgtagcggg tccctgtcca ctcggcatca cacggaatct   6240
gcaccgagtt cccccccgca gacccaaggt ccaactctcc aagcggcaat cctctctcgc   6300
ttcttcagcc ccactgaatg atcgcgtaac cgtaattaat ctagctacat taaggattaa   6360
gaaaaaatac gggtagaatt ggagtgcccc aattgtgagt ttagttgata gttgtagcca   6420
```

-continued

```
ccatgcaccg tcctcatctc agacggcact cgcgttacta cgcgaaagga gaggtgctta   6480
acaaacacat ggattgcggt ggaaaacggt gctgctcagg cgcagctgta ttcactcttt   6540
tctggacttg tgtcaggatt atgcgggagc atatctgctt tgtacgcaac gctatggacc   6600
gccatttatt tttgaggaat gctttttgga ctatcgtact gctttcttcc ttcgctagcc   6660
agagcaccgc cgccgtcacg tacgactaca ttttaggccg tcgcgcgctc gacgcgctaa   6720
ccataccggc ggttggcccg tataacagat acctcactag ggtatcaaga ggctgcgacg   6780
ttgtcgagct caacccgatt tctaacgtgg acgacatgat atcggcggcc aaagaaaaag   6840
agaagggggg ccctttcgag gcctccgtcg tctggttcta cgtgattaag ggcgacgacg   6900
gcgaggacaa gtactgtcca atctatagaa aagagtacag ggaatgtggc gacgtacaac   6960
tgctatctga atgcgccgtt caatctgcac agatgtgggc agtggactat gttcctagca   7020
cccttgtatc gcgaaatggc gcgggactga ctatattctc ccccactgct gcgctctctg   7080
gccaatactt gctgaccctg aaaatcggga gatttgcgca aacagctctc gtaactctag   7140
aagttaacga tcgctgttta aagatcgggt cgcagcttaa ctttttaccg tcgaaatgct   7200
ggacaacaga acagtatcag actggatttc aaggcgaaca cctttatccg atcgcagaca   7260
ccaatacacg acacgcggac gacgtatatc ggggatacga agatattctg cagcgctgga   7320
ataatttgct gaggaaaaag aatcctagcg cgccagaccc tcgtccagat agcgtcccgc   7380
aagaaattcc cgctgtaacc aagaaagcgg aagggcgcac cccggacgca gaaagcagcg   7440
aaaagaaggc ccctccagaa gactcggagg acgacatgca ggcagaggct tctggagaaa   7500
atcctgccgc cctccccgaa gacgacgaag tccccgagga caccgagcac gatgatccaa   7560
actcggatcc tgactattac aatgatatgc ccgccgtgat cccggtggag gagactacta   7620
aaagttctaa tgccgtctcc atgcccatat tcgcggcgtt cgtagcctgc gcggtcgcgc   7680
tcgtggggct actggtttgg agcatcgtaa aatgcgcgcg tagctaagct gtgtgtaact   7740
accgtgtact aagccccact cacccagatc atcatgacac aaaaaactaa tcgttacctc   7800
tctcgcttcc tcagccccac tgaatgatcg cgtaaccgta attaatctag ctacattaag   7860
gattaagaaa aaatacgggt agaattggag tgccccaatt gtgccaagat ggactcatct   7920
aggacaattg ggctgtactt tgattctgcc cattcttcta gcaacctgtt agcatttccg   7980
atcgtcctac aagacacagg agatgggaag aagcaaatcg ccccgcaata taggatccag   8040
cgccttgact tgtggactga tagtaaggag gactcagtat tcatcaccac ctatggattc   8100
atctttcaag ttgggaatga agaagccact gtcggcatga tcgatgataa acccaagcgc   8160
gagttacttt ccgctgcgat gctctgccta ggaagcgtcc caaataccgg agaccttatt   8220
gagctggcaa gggcctgtct cactatgata gtcacatgca agaagagtgc aactaatgct   8280
gagagaatgg ttttctcagt agtgcaggca ccccaagtgc tgcaaagctg tagggttgtg   8340
gcaaacaaat actcatcagt gaatgcagtc aagcacgtga aagcgccaga gaagattccc   8400
gggagtggaa ccctagaata caaggtgaac tttgtctcct tgactgtggt accgaagaag   8460
gatgtctaca agatccctgc tgcagtattg aaggtttctg gctcgagtct gtacaatctt   8520
gcgctcaatg tcactattaa tgtggaggta gacccgagga gtcctttggt taaatctctg   8580
tctaagtctg acagcggata ctatgctaac ctcttcttgc atattggact tatgaccacc   8640
gtagatagga aggggaagaa agtgacattt gacaagctgg aaaagaaaat aaggagcctt   8700
gatctatctg tcgggctcag tgatgtgctc gggccttccg tgttggtaaa agcaagaggt   8760
gcacggacta agcttttggc acctttcttc tctagcagtg ggacagcctg ctatcccata   8820
```

-continued

```
gcaaatgctt ctcctcaggt ggccaagata ctctggagtc aaaccgcgtg cctgcggagc   8880
gttaaaatca ttatccaagc aggtacccaa cgcgctgtcg cagtgaccgc cgaccacgag   8940
gttacctcta ctaagctgga gaaggggcac acccttgcca aatacaatcc ttttaagaaa   9000
taagctgcgt ctctgagatt gcgctccgcc cactcaccca gatcatcatg acacaaaaaa   9060
ctaatctgtc ttgattattt acagttagtt aacctgtcta tcaagttaga aaaaacacgg   9120
gtagaagatt ctggatcccg gttggcgccc tccaggtgca agatgggctc cagaccttct   9180
accaagaacc cagcacctat gatgctgact atccgggttg cgctggtact gagttgcatc   9240
tgtccggcaa actccattga tggcaggcct cttgcagctg caggaattgt ggttacagga   9300
gacaaagccg tcaacatata cacctcatcc cagacaggat caatcatagt taagctcctc   9360
ccgaatctgc ccaaggataa ggaggcatgt gcgaaagccc ccttggatgc atacaacagg   9420
acattgacca ctttgctcac ccccccttggt gactctatcc gtaggataca agagtctgtg   9480
actacatctg gaggggggag acaggggcgc cttataggcg ccattattgg cggtgtggct   9540
cttggggttg caactgccgc acaaataaca gcggccgcag ctctgataca agccaaacaa   9600
aatgctgcca acatcctccg acttaaagag agcattgccg caaccaatga ggctgtgcat   9660
gaggtcactg acggattatc gcaactagca gtggcagttg ggaagatgca gcagtttgtt   9720
aatgaccaac ttaataaaac agctcaggaa ttagactgca tcaaaattgc acagcaagtt   9780
ggtgtagagc tcaacctgta cctaaccgaa ttgactacag tattcggacc acaaatcact   9840
tcacctgctt taaacaagct gactattcag gcactttaca atctagctgg tggaaatatg   9900
gattacttat tgactaagtt aggtgtaggg aacaatcaac tcagctcatt aatcggtagc   9960
ggcttaatca ccggtaaccc tattctatac gactcacaga ctcaactctt gggtatacgg  10020
gtaactctac cttcagtcgg gaacctaaat aatatgcgtg ccacctactt ggaaacctta  10080
tccgtaagca caaccagggg atttgcctcg gcacttgtcc ccaaagtggt gacacaggtc  10140
ggttctgtga tagaagaact tgacacctca tactgtatag aaactgactt agatttatat  10200
tgtacaagaa tagtaacgtt ccctatgtcc cctggtattt attcctgctt gagcggcaat  10260
acgtcggcct gtatgtactc aaagaccgaa ggcgcactta ctacaccata catgactatc  10320
aaaggttcag tcatcgccaa ctgcaagatg acaacatgta gatgtgtaaa ccccccgggt  10380
atcatatcgc aaaactatgg agaagccgtg tctctaatag ataaacaatc atgcaatgtt  10440
ttatccttag gcgggataac tttaaggctc agtggggaat tcgatgtaac ttatcagaag  10500
aatatctcaa tacaagattc tcaagtaata ataacaggca atcttgatat ctcaactgag  10560
cttgggaatg tcaacaactc gatcagtaat gctttgaata agttagagga aagcaacaga  10620
aaactagaca aagtcaatgt caaactgact agcacatctg ctctcattac ctatatcgtt  10680
ttgactatca tatctcttgt ttttggtata cttagcctga ttctagcatg ctacctaatg  10740
tacaagcaaa aggcgcaaca aaagacctta ttatggcttg ggaataatac tctagatcag  10800
atgagagcca ctacaaaaat gtgaacacag atgaggaacg aaggtttccc taatagtaat  10860
ttgtgtgaaa gttctggtag tctgtcagtt cagagagtta agaaaaaact accggttgta  10920
gatgaccaaa ggacgatata cgggtagaac ggtaagagag gccgcccctc aattgcgagc  10980
caggcttcac aacctccgtt ctaccgcttc accgacaaca gtcctcaatc atggaccgcg  11040
ccgttagcca agttgcgtta gagaatgatg aaagagaggc aaaaaataca tggcgcttga  11100
tattccggat tgcaatctta ttcttaacag tagtgacctt ggctatatct gtagcctccc  11160
```

-continued

```
ttttatatag catgggggct agcacaccta gcgatcttgt aggcataccg actaggaatt  11220
ccagggcaga agaaaagatt acatctacac ttggttccaa tcaagatgta gtagatagga  11280
tatataagca agtggccctt gagtctccgt tggcattgtt aaaaactgag accacaatta  11340
tgaacgcaat aacatctctc tcttatcaga ttaatggagc tgcaaacaac agtgggtggg  11400
gggcacttat ccatgaccca gattatatag gggggatagg caaagaactc attgtagatg  11460
atgctagtga tgtcacatca ttctatccct ctgcatttca agaacatctg aattttatcc  11520
cggcgcctac tacaggatca ggttgcactc gaataccctc atttgacatg agtgctaccc  11580
attactgcta cacccataat gtaatattgt ctggatgcag agatcactca cattcatatc  11640
agtatttagc acttggtgtg ctccggacat ctgcaacagg gagggtattc ttttctactc  11700
tgcgttccat caacctggac gacacccaaa atcggaagtc ttgcagtgtg agtgcaactc  11760
ccctgggttg tgatatgctg tgctcgaaag tcacggagac agaggaagaa gattataact  11820
cagctgtccc tacgcggatg gtacatggga ggttagggtt cgacggccag taccacgaaa  11880
aggacctaga tgtcacaaca ttattcgggg actgggtggc caactaccca ggagtagggg  11940
gtggatcttt tattgacagc cgcgtatggt tctcagtcta cggagggtta aaacccaatt  12000
cacccagtga cactgtacag gaagggaaat atgtgatata caagcgatac aatgacacat  12060
gcccagatga gcaagactac cagattcgaa tggccaggtc ttcgtataag cctggacggt  12120
ttggtgggaa acgcatacag caggctatct tatctatcaa ggtgtcaaca tccttaggcg  12180
aagacccggt actgactgta ccgcccaaca cagtcacact catgggggcc gaaggcagaa  12240
ttctcacagt agggacatct catttcttgt atcaacgagg gtcatcatac ttctctcccg  12300
cgttattata tcctatgaca gtcagcaaca aaacagccac tcttcatagt ccttatacat  12360
tcaatgcctt cactcggcca ggtagtatcc cttgccaggc ttcagcaaga tgccccaacc  12420
cgtgtgttac tggagtctat acagatccac atcccctaat cttctataga aaccacacct  12480
tgcgaggggt attcgggaca atgcttgatg gtgtacaagc aagacttaac cctgcgtctg  12540
cagtattcga tagcacatcc cgcagtcgca ttactcgagt gagttcaagc agtaccaaag  12600
cagcatacac aacatcaact tgttttaaag tggtcaagac taataagacc tattgtctca  12660
gcattgctga aatatctaat actctcttcg gagaattcag aatcgtcccg ttactagttg  12720
agatcctcaa agatgacggg gttagagaag ccaggtctgg ctagttgagt caattataaa  12780
ggagttggaa agatggcatt gtatcaccta tcttctgcga catcaagaat caaaccgaat  12840
gccggcgcgt gctcgaattc catgttgcca gttgaccaca atcagccagt gctcatgcga  12900
tcagattaag ccttgtcaat agtctcttga ttaagaaaaa atgtaagtgg caatgagata  12960
caaggcaaaa cagctcatgg taaataatac gggtagaaca tggcgagctc cggtcctgaa  13020
agggcagagc atcagattat cctaccagag tcacacctgt cttcaccatt ggtcaagcac  13080
aaactactct attactggaa attaactggg ctaccgcttc ctgatgaatg tgacttcgac  13140
cacctcattc tcagccgaca atggaaaaaa atacttgaat cggcctctcc tgatactgag  13200
agaatgatag aactcggaag ggcagtacac caaactctta accacaattc cagaataacc  13260
ggagtgctcc accccaggtg tttagaagaa ctggctaata ttgaggtccc agattcaacc  13320
aacaaatttc ggaagattga gaagaagatc caaattcaca acacgagata tggagaactg  13380
ttcacaaggc tgtgtacgca tatagagaag aaactgctgg ggtcatcttg gtctaacaat  13440
gtcccccggt cagaggagtt cagcagcatt cgtacggatc cggcattctg gtttcactca  13500
aaatggtcca cagccaagtt tgcatggctc catataaaac agatccagag gcatctgatg  13560
```

gtggcagcta ggacaaggtc tgcggccaac aaattggtga tgctaaccca taaggtaggc 13620
caagtctttg tcactcctga acttgtcgtt gtgacgcata cgaatgagaa caagttcaca 13680
tgtcttaccc aggaacttgt attgatgtat gcagatatga tggagggcag agatatggtc 13740
aacataatat caaccacggc ggtgcatctc agaagcttat cagagaaaat tgatgacatt 13800
ttgcggttaa tagacgctct ggcaaaagac ttgggtaatc aagtctacga tgttgtatca 13860
ctaatggagg gatttgcata cggagctgtc cagctactcg agccgtcagg tacatttgca 13920
ggagatttct tcgcattcaa cctgcaggag cttaaagaca ttctaattgg cctcctcccc 13980
aatgatatag cagaatccgt gactcatgca atcgctactg tattctctgg tttagaacag 14040
aatcaagcag ctgagatgtt gtgtctgttg cgtctgtggg gtcacccact gcttgagtcc 14100
cgtattgcag caaaggcagt caggagccaa atgtgcgcac cgaaaatggt agactttgat 14160
atgatccttc aggtactgtc tttcttcaag ggaacaatca tcaacgggta cagaaagaag 14220
aatgcaggtg tgtggccgcg agtcaaagtg gatacaatat atgggaaggt cattgggcaa 14280
ctacatgcag attcagcaga gatttcacac gatatcatgt tgagagagta taagagttta 14340
tctgcacttg aatttgagcc atgtatagaa tatgaccctg tcaccaacct gagcatgttc 14400
ctaaaagaca aggcaatcgc acaccccaac gataattggc ttgcctcgtt taggcggaac 14460
cttctctccg aagaccagaa gaaacatgta aaagaagcaa cttcgactaa tcgcctcttg 14520
atagagtttt tagagtcaaa tgattttgat ccatataaag agatggaata tctgacgacc 14580
cttgagtacc ttagagatga caatgtggca gtatcatact cgctcaagga gaaggaagtg 14640
aaagttaatg gacggatctt cgctaagctg acaaagaagt taaggaactg tcaggtgatg 14700
gcggaaggga tcctagccga tcagattgca cctttctttc agggaaatgg agtcattcag 14760
gatagcatat ccttgaccaa gagtatgcta gcgatgagtc aactgtcttt taacagcaat 14820
aagaaacgta tcactgactg taaagaaaga gtatcttcaa accgcaatca tgatccgaaa 14880
agcaagaacc gtcggagagt tgcaaccttc ataacaactg acctgcaaaa gtactgtctt 14940
aattggagat atcagacgat caaattgttc gctcatgcca tcaatcagtt gatgggccta 15000
cctcatttct tcgagtggat tcacctaaga ctgatggaca ctacgatgtt cgtaggagac 15060
cctttcaatc ctccaagtga ccctactgac tgtgacctct caagagtccc taatgatgac 15120
atatatattg tcagtgccag agggggtatc gaaggattat gccagaagct atggacaatg 15180
atctcaattg ctgcaatcca acttgctgca gctagatcgc attgtcgtgt tgcctgtatg 15240
gtacagggtg ataatcaagt aatagcagta acgagagagg taagatcaga tgactctccg 15300
gagatggtgt tgacacagtt gcatcaagcc agtgataatt tcttcaagga attaatccat 15360
gtcaatcatt tgattggcca taatttgaag gatcgtgaaa ccatcaggtc agacacattc 15420
ttcatataca gcaaacgaat cttcaaagat ggagcaatcc tcagtcaagt cctcaaaaat 15480
tcatctaaat tagtgctagt gtcaggtgat ctcagtgaaa acactgtaat gtcctgtgcc 15540
aacattgcct ctactgtagc acggctatgc gagaacgggc ttcccaaaga cttctgttac 15600
tatttaaact atataatgag ttgtgtgcag acatactttg actctgagtt ctccatcacc 15660
aacaattcgc accccgatct taatcagtcg tggattgagg acatctcttt tgtgcactca 15720
tatgttctga ctcctgccca attaggggga ctgagtaacc ttcaatactc aaggctctac 15780
actagaaata tcggtgaccc ggggactact gcttttgcag agatcaagcg actagaagca 15840
gtgggattac tgagtcctaa cattatgact aatatcttaa ctaggccgcc tgggaatgga 15900

```
gattgggcca gtctgtgcaa cgacccatac tctttcaatt ttgagactgt tgcaagccca  15960
aatattgttc ttaagaaaca tacgcaaaga gtcctatttg aaacttgttc aaatccctta  16020
ttgtctggag tgcacacaga ggataatgag gcagaagaga aggcattggc tgaattcttg  16080
cttaatcaag aggtgattca tccccgcgtt gcgcatgcca tcatggaggc aagctctgta  16140
ggtaggagaa agcaaattca agggcttgtt gacacaacaa acaccgtaat taagattgcg  16200
cttactagga ggccattagg catcaagagg ctgatgcgga tagtcaatta ttctagcatg  16260
catgcaatgc tgtttagaga cgatgttttt tcctccagta gatccaacca ccccttagtc  16320
tcttctaata tgtgttctct gacactggca gactatgcac ggaatagaag ctggtcacct  16380
ttgacgggag gcaggaaaat actgggtgta tctaatcctg atacgataga actcgtagag  16440
ggtgagattc ttagtgtaag cggagggtgt acaagatgtg acagcggaga tgaacaattt  16500
acttggttcc atcttccaag caatatagaa ttgaccgatg acaccagcaa gaatcctccg  16560
atgagggtac catatctcgg gtcaaagaca caggagagga gagctgcctc acttgcaaaa  16620
atagctcata tgtcgccaca tgtaaaggct gccctaaggg catcatccgt gttgatctgg  16680
gcttatgggg ataatgaagt aaattggact gctgctctta cgattgcaaa atctcggtgc  16740
aatgtaaact tagagtatct tcggttactg tcccctttac ccacggctgg gaatcttcaa  16800
catagactag atgatggtat aactcagatg acattcaccc ctgcatctct ctacagggtg  16860
tcaccttaca ttcacatatc caatgattct caaaggctgt tcactgaaga aggagtcaaa  16920
gaggggaatg tggtttacca acagatcatg ctcttgggtt tatctctaat cgaatcgatc  16980
tttccaatga caacaaccag gacatatgat gagatcacac tgcacctaca tagtaaattt  17040
agttgctgta tcagagaagc acctgttgcg gttcctttcg agctacttgg ggtggtaccg  17100
gaactgagga cagtgacctc aaataagttt atgtatgatc ctagccctgt atcggaggga  17160
gactttgcga gacttgactt agctatcttc aagagttatg agcttaatct ggagtcatat  17220
cccacgatag agctaatgaa cattctttca atatccagcg ggaagttgat tggccagtct  17280
gtggtttctt atgatgaaga tacctccata aagaatgatg ccataatagt gtatgacaat  17340
acccgaaatt ggatcagtga agctcagaat tcagatgtgg tccgcctatt tgaatatgca  17400
gcacttgaag tgctcctcga ctgttcttac caactctatt acctgagagt aagaggccta  17460
gacaatattg tcttatatat gggtgattta tacaagaata tgccaggaat tctactttcc  17520
aacattgcag ctacaatatc tcatcctgtc attcattcaa ggttacatgc agtgggcctg  17580
gtcaaccatg acggatcaca ccaacttgca gatacggatt ttatcgaaat gtctgcaaaa  17640
ctgttagtat cttgcacccg acgtgtgatc tccggcttat attcaggaaa taagtatgat  17700
ctgctgttcc catctgtctt agatgataac ctgaatgaga agatgcttca gctgatatcc  17760
cggttatgct gtctgtacac ggtactcttt gctacaacaa gagaaatccc gaaaataaga  17820
ggcttaactg cagaagagaa atgttcaata ctcactgagt atttactgtc ggatgctgtg  17880
aaaccattac ttagccccga tcaagtgagc tctatcatgt ctcctaacat aattacattc  17940
ccagctaatc tgtactacat gtctcggaag agcctcaatt tgatcaggga aagggaggac  18000
agggatacta tcctggcgtt gttgttcccc caagagccat tattagagtt cccttctgtg  18060
caagatattg gtgctcgagt gaaagatcca ttcacccgac aacctgcggc atttttgcaa  18120
gagttagatt tgagtgctcc agcaaggtat gacgcattca cacttagtca gattcatcct  18180
gaactcacat ctccaaatcc ggaggaagac tacttagtac gatacttgtt cagagggata  18240
gggactgcat cttcctcttg gtataaggca tcccatctcc tttctgtacc cgaggtaaga  18300
```

| | |
|---|---:|
| tgtgcaagac acgggaactc cttatacttg gctgaaggaa gcggagccat catgagtctt | 18360 |
| cttgaactgc atgtaccaca tgaaactatc tattacaata cgctcttttc aaatgagatg | 18420 |
| aaccccccgc aacgacattt cgggccgacc ccaactcagt ttttgaattc ggttgtttat | 18480 |
| aggaatctac aggcggaggt aacatgcaag gatggatttg tccaagagtt ccgtccatta | 18540 |
| tggagagaaa atacagagga aagtgacctg acctcagata aagcagtggg gtatattaca | 18600 |
| tctgcagtac cctacagatc tgtatcattg ctgcattgtg acattgaaat tcctccaggg | 18660 |
| tccaatcaaa gcttactaga tcaactagct atcaatttat ctctgattgc catgcattct | 18720 |
| gtaagggagg gcggggtagt aatcatcaaa gtgttgtatg caatgggata ctactttcat | 18780 |
| ctactcatga acttgtttgc tccgtgttcc acaaaggat atattctctc taatggttat | 18840 |
| gcatgtcgag gggatatgga gtgttacctg gtatttgtca tgggttacct gggcgggcct | 18900 |
| acatttgtac atgaggtggt gaggatggca aaaactctgg tgcagcggca cggtacgctt | 18960 |
| ttgtctaaat cagatgagat cacactgacc aggttattca cctcacagcg gcagcgtgtg | 19020 |
| acagacatcc tatccagtcc tttaccaaga ttaataaagt acttgaggaa gaatattgac | 19080 |
| actgcgctga ttgaagccgg gggacagccc gtccgtccat tctgtgcgga gagtctggtg | 19140 |
| agcacgctag cgaacataac tcagataacc cagatcatcg ctagccacat tgacacagtt | 19200 |
| atccggtctg tgatatatat ggaagctgag ggtgatctcg ctgacacagt atttctattt | 19260 |
| accccttaca atctctctac tgacgggaaa aagaggacat cacttaaaca gtgcacgaga | 19320 |
| cagatcctag aggttacaat actaggtctt agagtcgaaa atctcaataa aataggcgat | 19380 |
| ataatcagcc tagtgcttaa aggcatgatc tccatggagg accttatccc actaaggaca | 19440 |
| tacttgaagc atagtacctg ccctaaatat ttgaaggctg tcctaggtat taccaaactc | 19500 |
| aaagaaatgt ttacagacac ttctgtactg tacttgactc gtgctcaaca aaaattctac | 19560 |
| atgaaaacta taggcaatgc agtcaaagga tattacagta actgtgactc ctaacgaaaa | 19620 |
| tcacatatta ataggctcct tttttggcca attgtattct tgttgattta attatattat | 19680 |
| gttagaaaaa agttgaactc tgactcctta ggactcgaat tcgaactcaa ataaatgtct | 19740 |
| ttaaaaaagg ttgcgcacaa ttattcttga gtgtagtctc gtcattcacc aaatctttgt | 19800 |
| ttggtggccg gcatggtccc agcctcctcg ct | 19832 |

<210> SEQ ID NO 17
<211> LENGTH: 16692
<212> TYPE: DNA
<213> ORGANISM: Artificial Sequence
<220> FEATURE:
<223> OTHER INFORMATION: chimeric virus

<400> SEQUENCE: 17

| | |
|---|---:|
| accaaacaga gaatccgtga gtcgcgataa aaggcgaaag agcaattgaa gtcacacggg | 60 |
| tagaaggtgt gaatctcgag tgcgagcccg aagcacaaac tcgagaaagc cttctgccaa | 120 |
| catgtcttcc gtatttgatg agtacgaaca gctcctcgcg gctcagactc gccccaatgg | 180 |
| agctcatgga gggggagaaa aagggagtac cttaaaagta gacgtcccgg tattcactct | 240 |
| taacagtgat gacccagaag atagatggag ctttgtggta ttctgcctcc ggattgctgt | 300 |
| tagcgaagat gccaacaaac cactcaggca aggtgctctc atatctcttt tatgctccca | 360 |
| ctcacaggta atgaggaacc atgttgccct tgcaggaaaa cagaatgaag ccacattggc | 420 |
| cgtgcttgag attgatggct ttgccaacgg cacgcccag ttcaacaata ggagtggagt | 480 |

```
gtctgaagag agagcacaga gatttgcgat gatagcagga tctctccctc gggcatgcag    540
caacggaacc ccgttcgtca cagccggggc cgaagatgat gcaccagaag acatcaccga    600
taccctggag aggatcctct ctatccaggc tcaagtatgg gtcacagtag caaaagccat    660
gactgcgtat gagactgcag atgagtcgga aacaaggcga atcaataagt atatgcagca    720
aggcagggtc caaaagaaat acatcctcta ccccgtatgc aggagcacaa tccaactcac    780
gatcagacag tctcttgcag tccgcatctt tttggttagc gagctcaaga gaggccgcaa    840
cacggcaggt ggtacctcta cttattataa cctggtaggg gacgtagact catacatcag    900
gaataccggg cttactgcat tcttcttgac actcaagtac ggaatcaaca ccaagacatc    960
agcccttgca cttagtagcc tctcaggcga catccagaag atgaagcagc tcatgcgttt   1020
gtatcggatg aaaggagata atgcgccgta catgacatta cttggtgata gtgaccagat   1080
gagctttgcg cctgccgagt atgcacaact ttactccttt gccatgggta tggcatcagt   1140
cctagataaa ggtactggga aataccaatt tgccagggac tttatgagca catcattctg   1200
gagacttgga gtagagtacg ctcaggctca gggaagtagc attaacgagg atatggctgc   1260
cgagctaaag ctaaccccag cagcaaggag gggcctggca gctgctgccc aacgggtctc   1320
cgaggagacc agcagcatag acatgcctac tcaacaagtc ggagtcctca ctgggcttag   1380
cgaggggggg tcccaagctc tacaaggcgg atcgaataga tcgcaagggc aaccagaagc   1440
cggggatggg gagacccaat tcctggatct gatgagagcg gtagcaaata gcatgaggga   1500
ggcgccaaac tctgcacagg gcactcccca atcggggcct cccccaactc ctgggccatc   1560
ccaagataac gacaccgact gggggtattg atggacaaaa cccagcctgc ttccacaaaa   1620
acatcccaat gccctcaccc gtagtcgacc cctcgatttg cggctctata tgaccacacc   1680
ctcaaacaaa catcccccctc tttcctccct cccccctgctg tacaactccg cacgccctag   1740
ataccacagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaaggcaa ccccgatcga caggacagat   2100
ctgacaaaca accatccaca cccgggcaaa cgaccccgca tgacagcccg ccggccacat   2160
ccgccgacca gccccccacc caggccacag acgaagccgt cgacacacag ctcaggaccg   2220
gagcaagcaa ctctctgctg ttgatgcttg acaagctcag caataaatcg tccaatgcta   2280
aaaagggccc atggtcgagc cccaagagg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aatacccttg   2520
tatctgcgga tcatgtccag ccacctgtag actttgtgca agcgatgatg tctatgatgg   2580
aggcgatatc acagagagta agtaaggtcg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
cctctcccta tgtgacacaa ggaggcgaaa tggcacttaa taaactttcg caaccagtgc   2880
```

```
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc ccccgcagac ccaaggtcca actctccaag cggcaatcct   3180
ctctcgcttc ttcagcccca ctgaatgatc gcgtaaccgt aattaatcta gctacattaa   3240
ggattaagaa aaaatacggg tagaattgga gtgccccaat tgtgagttta gttgatagtt   3300
gtagccacca tgcaccgtcc tcatctcaga cggcactcgc gttactacgc gaaaggagag   3360
gtgcttaaca aacacatgga ttgcggtgga aaacggtgct gctcaggcgc agctgtattc   3420
actcttttct ggacttgtgt caggattatg cgggagcata tctgctttgt acgcaacgct   3480
atggaccgcc atttattttt gaggaatgct ttttggacta tcgtactgct ttcttccttc   3540
gctagccaga gcaccgccgc cgtcacgtac gactacattt taggccgtcg cgcgctcgac   3600
gcgctaacca taccggcggt tggcccgtat aacagatacc tcactagggt atcaagaggc   3660
tgcgacgttg tcgagctcaa cccgatttct aacgtggacg acatgatatc ggcggccaaa   3720
gaaaaagaga aggggggccc tttcgaggcc tccgtcgtct ggttctacgt gattaagggc   3780
gacgacggcg aggacaagta ctgtccaatc tatagaaaag agtacaggga atgtggcgac   3840
gtacaactgc tatctgaatg cgccgttcaa tctgcacaga tgtgggcagt ggactatgtt   3900
cctagcaccc ttgtatcgcg aaatggcgcg ggactgacta tattctcccc cactgctgcg   3960
ctctctggcc aatacttgct gaccctgaaa atcgggagat ttgcgcaaac agctctcgta   4020
actctagaag ttaacgatcg ctgtttaaag atcgggtcgc agcttaactt tttaccgtcg   4080
aaatgctgga caacagaaca gtatcagact ggatttcaag gcgaacacct ttatccgatc   4140
gcagacacca atacacgaca cgcggacgac gtatatcggg gatacgaaga tattctgcag   4200
cgctggaata atttgctgag gaaaaagaat cctagcgcgc cagaccctcg tccagatagc   4260
gtcccgcaag aaattcccgc tgtaaccaag aaagcggaag ggcgcacccc ggacgcagaa   4320
agcagcgaaa agaaggcccc tccagaagac tcggaggacg acatgcaggc agaggcttct   4380
ggagaaaatc ctgccgccct ccccgaagac gacgaagtcc ccgaggacac cgagcacgat   4440
gatccaaact cggatcctga ctattacaat gatatgcccg ccgtgatccc ggtggaggag   4500
actactaaaa gttctaatgc cgtctccatg cccatattcg cggcgttcgt agcctgcgcg   4560
gtcgcgctcg tggggctact ggtttggagc atcgtaaaat gcgcgcgtag ctaagctgtg   4620
tgtaactacc gtgtactaag ccccactcac ccagatcatc atgacacaaa aaactaatcg   4680
ttacctctct cgcttcctca gccccactga atgatcgcgt aaccgtaatt aatctagcta   4740
cattaaggat taagaaaaaa tacgggtaga attggagtgc cccaattgtg ccaagatgga   4800
ctcatctagg acaattgggc tgtactttga ttctgcccat tcttctagca acctgttagc   4860
atttccgatc gtcctacaag acacaggaga tgggaagaag caaatcgccc cgcaatatag   4920
gatccagcgc cttgacttgt ggactgatag taaggaggac tcagtattca tcaccaccta   4980
tggattcatc tttcaagttg ggaatgaaga agccactgtc ggcatgatcg atgataaacc   5040
caagcgcgag ttactttccg ctgcgatgct ctgcctagga agcgtcccaa ataccggaga   5100
ccttattgag ctggcaaggg cctgtctcac tatgatagtc acatgcaaga agagtgcaac   5160
taatgctgag agaatggttt tctcagtagt gcaggcaccc caagtgctgc aaagctgtag   5220
```

-continued ggttgtggca aacaaatact catcagtgaa tgcagtcaag cacgtgaaag cgccagagaa 5280
gattcccggg agtggaaccc tagaatacaa ggtgaacttt gtctccttga ctgtggtacc 5340
gaagaaggat gtctacaaga tccctgctgc agtattgaag gtttctggct cgagtctgta 5400
caatcttgcg ctcaatgtca ctattaatgt ggaggtagac ccgaggagtc ctttggttaa 5460
atctctgtct aagtctgaca gcggatacta tgctaacctc ttcttgcata ttggacttat 5520
gaccaccgta gataggaagg ggaagaaagt gacatttgac aagctggaaa agaaaataag 5580
gagccttgat ctatctgtcg ggctcagtga tgtgctcggg ccttccgtgt tggtaaaagc 5640
aagaggtgca cggactaagc ttttggcacc tttcttctct agcagtggga cagcctgcta 5700
tcccatagca aatgcttctc ctcaggtggc caagatactc tggagtcaaa ccgcgtgcct 5760
gcggagcgtt aaaatcatta tccaagcagg tacccaacgc gctgtcgcag tgaccgccga 5820
ccacgaggtt acctctacta agctggagaa ggggcacacc cttgccaaat acaatccttt 5880
taagaaataa gctgcgtctc tgagattgcg ctccgcccac tcacccagat catcatgaca 5940
caaaaaacta atctgtcttg attatttaca gttagttaac ctgtctatca agttagaaaa 6000
aacacgggta gaagattctg gatcccggtt ggcgccctcc aggtgcaaga tgggctccag 6060
accttctacc aagaacccag cacctatgat gctgactatc cgggttgcgc tggtactgag 6120
ttgcatctgt ccggcaaact ccattgatgg caggcctctt gcagctgcag gaattgtggt 6180
tacaggagac aaagccgtca acatatacac ctcatcccag acaggatcaa tcatagttaa 6240
gctcctcccg aatctgccca aggataagga ggcatgtgcg aaagccccct tggatgcata 6300
caacaggaca ttgaccactt tgctcacccc ccttggtgac tctatccgta ggatacaaga 6360
gtctgtgact acatctggag gggggagaca ggggcgcctt ataggcgcca ttattggcgg 6420
tgtggctctt ggggttgcaa ctgccgcaca aataacagcg gccgcagctc tgatacaagc 6480
caaacaaaat gctgccaaca tcctccgact taaagagagc attgccgcaa ccaatgaggc 6540
tgtgcatgag gtcactgacg gattatcgca actagcagtg gcagttggga agatgcagca 6600
gtttgttaat gaccaactta ataaaacagc tcaggaatta gactgcatca aaattgcaca 6660
gcaagttggt gtagagctca acctgtacct aaccgaattg actacagtat tcggaccaca 6720
aatcacttca cctgctttaa acaagctgac tattcaggca ctttacaatc tagctggtgg 6780
aaatatggat tacttattga ctaagttagg tgtagggaac aatcaactca gctcattaat 6840
cggtagcggc ttaatcaccg gtaaccctat tctatacgac tcacagactc aactcttggg 6900
tatacgggta actctacctt cagtcgggaa cctaaataat atgcgtgcca cctacttgga 6960
aaccttatcc gtaagcacaa ccaggggatt tgcctcggca cttgtcccca aagtggtgac 7020
acaggtcggt tctgtgatag aagaacttga cacctcatac tgtatagaaa ctgacttaga 7080
tttatattgt acaagaatag taacgttccc tatgtcccct ggtatttatt cctgcttgag 7140
cggcaatacg tcggcctgta tgtactcaaa gaccgaaggc gcacttacta caccatacat 7200
gactatcaaa ggttcagtca tcgccaactg caagatgaca acatgtagat gtgtaaaccc 7260
cccgggtatc atatcgcaaa actatggaga agccgtgtct ctaatagata aacaatcatg 7320
caatgtttta tccttaggcg ggataacttt aaggctcagt ggggaattcg atgtaactta 7380
tcagaagaat atctcaatac aagattctca agtaataata acaggcaatc ttgatatctc 7440
aactgagctt gggaatgtca acaactcgat cagtaatgct ttgaataagt tagaggaaag 7500
caacagaaaa ctagacaaag tcaatgtcaa actgactagc acatctgctc tcattaccta 7560
tatcgttttg actatcatat ctcttgtttt tggtatactt agcctgattc tagcatgcta 7620

-continued

```
cctaatgtac aagcaaaagg cgcaacaaaa gaccttatta tggcttggga ataatactct   7680
agatcagatg agagccacta caaaaatgtg aacacagatg aggaacgaag gtttccctaa   7740
tagtaatttg tgtgaaagtt ctggtagtct gtcagttcag agagttaaga aaaaactacc   7800
ggttgtagat gaccaaagga cgatatacgg gtagaacggt aagagaggcc gcccctcaat   7860
tgcgagccag gcttcacaac ctccgttcta ccgcttcacc gacaacagtc ctcaatcatg   7920
gaccgcgccg ttagccaagt tgcgttagag aatgatgaaa gagaggcaaa aaatacatgg   7980
cgcttgatat tccggattgc aatcttattc ttaacagtag tgaccttggc tatatctgta   8040
gcctcccttt tatatagcat gggggctagc acacctagcg atcttgtagg cataccgact   8100
aggaattcca gggcagaaga aaagattaca tctacacttg gttccaatca agatgtagta   8160
gataggatat ataagcaagt ggcccttgag tctccgttgg cattgttaaa aactgagacc   8220
acaattatga acgcaataac atctctctct tatcagatta atggagctgc aaacaacagt   8280
gggtgggggg cacttatcca tgacccagat tatatagggg ggataggcaa agaactcatt   8340
gtagatgatg ctagtgatgt cacatcattc tatccctctg catttcaaga acatctgaat   8400
tttatcccgg cgcctactac aggatcaggt tgcactcgaa taccctcatt tgacatgagt   8460
gctacccatt actgctacac ccataatgta atattgtctg gatgcagaga tcactcacat   8520
tcatatcagt atttagcact tggtgtgctc cggacatctg caacagggag ggtattcttt   8580
tctactctgc gttccatcaa cctggacgac acccaaaatc ggaagtcttg cagtgtgagt   8640
gcaactcccc tgggttgtga tatgctgtgc tcgaaagtca cggagacaga ggaagaagat   8700
tataactcag ctgtccctac gcggatggta catgggaggt tagggttcga cggccagtac   8760
cacgaaaagg acctagatgt cacaacatta ttcggggact gggtggccaa ctacccagga   8820
gtagggggtg gatcttttat tgacagccgc gtatggttct cagtctacgg agggttaaaa   8880
cccaattcac ccagtgacac tgtacaggaa gggaaatatg tgatatacaa gcgatacaat   8940
gacacatgcc cagatgagca agactaccag attcgaatgg ccaggtcttc gtataagcct   9000
ggacggtttg gtgggaaacg catacagcag gctatcttat ctatcaaggt gtcaacatcc   9060
ttaggcgaag acccggtact gactgtaccg cccaacacag tcacactcat gggggccgaa   9120
ggcagaattc tcacagtagg gacatctcat ttcttgtatc aacgagggtc atcatacttc   9180
tctcccgcgt tattatatcc tatgacagtc agcaacaaaa cagccactct tcatagtcct   9240
tatacattca atgccttcac tcggccaggt agtatccctt gccaggcttc agcaagatgc   9300
cccaacccgt gtgttactgg agtctataca gatccacatc ccctaatctt ctatagaaac   9360
cacaccttgc gaggggtatt cgggacaatg cttgatggtg tacaagcaag acttaaccct   9420
gcgtctgcag tattcgatag cacatcccgc agtcgcatta ctcgagtgag ttcaagcagt   9480
accaaagcag catacacaac atcaacttgt tttaaagtgg tcaagactaa taagacctat   9540
tgtctcagca ttgctgaaat atctaatact ctcttcggag aattcagaat cgtcccgtta   9600
ctagttgaga tcctcaaaga tgacggggtt agagaagcca ggtctggcta gttgagtcaa   9660
ttataaagga gttggaaaga tggcattgta tcacctatct tctgcgacat caagaatcaa   9720
accgaatgcc ggcgcgtgct cgaattccat gttgccagtt gaccacaatc agccagtgct   9780
catgcgatca gattaagcct tgtcaatagt ctcttgatta agaaaaaatg taagtggcaa   9840
tgagatacaa ggcaaaacag ctcatggtaa ataatacggg tagaacatgg cgagctccgg   9900
tcctgaaagg gcagagcatc agattatcct accagagtca cacctgtctt caccattggt   9960
```

-continued

```
caagcacaaa ctactctatt actggaaatt aactgggcta ccgcttcctg atgaatgtga  10020
cttcgaccac ctcattctca gccgacaatg gaaaaaaata cttgaatcgg cctctcctga  10080
tactgagaga atgatagaac tcggaagggc agtacaccaa actcttaacc acaattccag  10140
aataaccgga gtgctccacc ccaggtgttt agaagaactg gctaatattg aggtcccaga  10200
ttcaaccaac aaatttcgga agattgagaa gaagatccaa attcacaaca cgagatatgg  10260
agaactgttc acaaggctgt gtacgcatat agagaagaaa ctgctggggt catcttggtc  10320
taacaatgtc ccccggtcag aggagttcag cagcattcgt acggatccgg cattctggtt  10380
tcactcaaaa tggtccacag ccaagtttgc atggctccat ataaaacaga tccagaggca  10440
tctgatggtg gcagctagga caaggtctgc ggccaacaaa ttggtgatgc taacccataa  10500
ggtaggccaa gtctttgtca ctcctgaact tgtcgttgtg acgcatacga atgagaacaa  10560
gttcacatgt cttacccagg aacttgtatt gatgtatgca gatatgatgg agggcagaga  10620
tatggtcaac ataatatcaa ccacggcggt gcatctcaga agcttatcag agaaaattga  10680
tgacattttg cggttaatag acgctctggc aaaagacttg ggtaatcaag tctacgatgt  10740
tgtatcacta atggagggat ttgcatacgg agctgtccag ctactcgagc cgtcaggtac  10800
atttgcagga gatttcttcg cattcaacct gcaggagctt aaagacattc taattggcct  10860
cctccccaat gatatagcag aatccgtgac tcatgcaatc gctactgtat tctctggttt  10920
agaacagaat caagcagctg agatgttgtg tctgttgcgt ctgtggggtc acccactgct  10980
tgagtcccgt attgcagcaa aggcagtcag gagccaaatg tgcgcaccga aaatggtaga  11040
ctttgatatg atccttcagg tactgtcttt cttcaaggga acaatcatca acgggtacag  11100
aaagaagaat gcaggtgtgt ggccgcgagt caaagtggat acaatatatg ggaaggtcat  11160
tgggcaacta catgcagatt cagcagagat ttcacacgat atcatgttga gagagtataa  11220
gagtttatct gcacttgaat ttgagccatg tatagaatat gaccctgtca ccaacctgag  11280
catgttccta aaagacaagg caatcgcaca ccccaacgat aattggcttg cctcgtttag  11340
gcggaacctt ctctccgaag accagaagaa acatgtaaaa gaagcaactt cgactaatcg  11400
cctcttgata gagtttttag agtcaaatga ttttgatcca tataaagaga tggaatatct  11460
gacgaccctt gagtacctta gagatgacaa tgtggcagta tcatactcgc tcaaggagaa  11520
ggaagtgaaa gttaatggac ggatcttcgc taagctgaca aagaagttaa ggaactgtca  11580
ggtgatggcg gaagggatcc tagccgatca gattgcacct ttctttcagg gaaatggagt  11640
cattcaggat agcatatcct tgaccaagag tatgctagcg atgagtcaac tgtcttttaa  11700
cagcaataag aaacgtatca ctgactgtaa agaaagagta tcttcaaacc gcaatcatga  11760
tccgaaaagc aagaaccgtc ggagagttgc aaccttcata acaactgacc tgcaaaagta  11820
ctgtcttaat tggagatatc agacgatcaa attgttcgct catgccatca atcagttgat  11880
gggcctacct catttcttcg agtggattca cctaagactg atggacacta cgatgttcgt  11940
aggagaccct ttcaatcctc caagtgaccc tactgactgt gacctctcaa gagtccctaa  12000
tgatgacata tatattgtca gtgccagagg gggtatcgaa ggattatgcc agaagctatg  12060
gacaatgatc tcaattgctg caatccaact tgctgcagct agatcgcatt gtcgtgttgc  12120
ctgtatggta cagggtgata atcaagtaat agcagtaacg agagaggtaa gatcagatga  12180
ctctccggag atggtgttga cacagttgca tcaagccagt gataatttct tcaaggaatt  12240
aatccatgtc aatcatttga ttggccataa tttgaaggat cgtgaaacca tcaggtcaga  12300
cacattcttc atatacagca aacgaatctt caaagatgga gcaatcctca gtcaagtcct  12360
```

```
caaaaattca tctaaattag tgctagtgtc aggtgatctc agtgaaaaca ctgtaatgtc  12420
ctgtgccaac attgcctcta ctgtagcacg gctatgcgag aacgggcttc ccaaagactt  12480
ctgttactat ttaaactata taatgagttg tgtgcagaca tactttgact ctgagttctc  12540
catcaccaac aattcgcacc ccgatcttaa tcagtcgtgg attgaggaca tctcttttgt  12600
gcactcatat gttctgactc ctgcccaatt agggggactg agtaaccttc aatactcaag  12660
gctctacact agaaatatcg gtgacccggg gactactgct tttgcagaga tcaagcgact  12720
agaagcagtg ggattactga gtcctaacat tatgactaat atcttaacta ggccgcctgg  12780
gaatggagat tgggccagtc tgtgcaacga cccatactct ttcaattttg agactgttgc  12840
aagcccaaat attgttctta agaaacatac gcaaagagtc ctatttgaaa cttgttcaaa  12900
tcccttattg tctggagtgc acacagagga taatgaggca gaagagaagg cattggctga  12960
attcttgctt aatcaagagg tgattcatcc ccgcgttgcg catgccatca tggaggcaag  13020
ctctgtaggt aggagaaagc aaattcaagg gcttgttgac acaacaaaca ccgtaattaa  13080
gattgcgctt actaggaggc cattaggcat caagaggctg atgcggatag tcaattattc  13140
tagcatgcat gcaatgctgt ttagagacga tgttttttcc tccagtagat ccaaccaccc  13200
cttagtctct tctaatatgt gttctctgac actggcagac tatgcacgga atagaagctg  13260
gtcacctttg acgggaggca ggaaaatact gggtgtatct aatcctgata cgatagaact  13320
cgtagagggt gagattctta gtgtaagcgg agggtgtaca agatgtgaca gcggagatga  13380
acaatttact tggttccatc ttccaagcaa tatagaattg accgatgaca ccagcaagaa  13440
tcctccgatg agggtaccat atctcgggtc aaagacacag gagaggagag ctgcctcact  13500
tgcaaaaata gctcatatgt cgccacatgt aaaggctgcc ctaagggcat catccgtgtt  13560
gatctgggct tatggggata atgaagtaaa ttggactgct gctcttacga ttgcaaaatc  13620
tcggtgcaat gtaaacttag agtatcttcg gttactgtcc cctttaccca cggctgggaa  13680
tcttcaacat agactagatg atggtataac tcagatgaca ttcacccctg catctctcta  13740
cagggtgtca ccttacattc acatatccaa tgattctcaa aggctgttca ctgaagaagg  13800
agtcaaagag gggaatgtgg tttaccaaca gatcatgctc ttgggtttat ctctaatcga  13860
atcgatcttt ccaatgacaa caaccaggac atatgatgag atcacactgc acctacatag  13920
taaatttagt tgctgtatca gagaagcacc tgttgcggtt cctttcgagc tacttggggt  13980
ggtaccggaa ctgaggacag tgacctcaaa taagtttatg tatgatccta gccctgtatc  14040
ggagggagac tttgcgagac ttgacttagc tatcttcaag agttatgagc ttaatctgga  14100
gtcatatccc acgatagagc taatgaacat tctttcaata tccagcggga agttgattgg  14160
ccagtctgtg gtttcttatg atgaagatac ctccataaag aatgatgcca taatagtgta  14220
tgacaatacc cgaaattgga tcagtgaagc tcagaattca gatgtggtcc gcctatttga  14280
atatgcagca cttgaagtgc tcctcgactg ttcttaccaa ctctattacc tgagagtaag  14340
aggcctagac aatattgtct tatatatggg tgatttatac aagaatatgc caggaattct  14400
actttccaac attgcagcta caatatctca tcctgtcatt cattcaaggt tacatgcagt  14460
gggcctggtc aaccatgacg gatcacacca acttgcagat acggatttta tcgaaatgtc  14520
tgcaaaactg ttagtatctt gcacccgacg tgtgatctcc ggcttatatt caggaaataa  14580
gtatgatctg ctgttcccat ctgtcttaga tgataacctg aatgagaaga tgcttcagct  14640
gatatcccgg ttatgctgtc tgtacacggt actctttgct acaacaagag aaatcccgaa  14700
```

```
aataagaggc ttaactgcag aagagaaatg ttcaatactc actgagtatt tactgtcgga  14760
tgctgtgaaa ccattactta gccccgatca agtgagctct atcatgtctc ctaacataat  14820
tacattccca gctaatctgt actacatgtc tcggaagagc ctcaatttga tcagggaaag  14880
ggaggacagg gatactatcc tggcgttgtt gttcccccaa gagccattat tagagttccc  14940
ttctgtgcaa gatattggtg ctcgagtgaa agatccattc acccgacaac ctgcggcatt  15000
tttgcaagag ttagatttga gtgctccagc aaggtatgac gcattcacac ttagtcagat  15060
tcatcctgaa ctcacatctc caaatccgga ggaagactac ttagtacgat acttgttcag  15120
agggataggg actgcatctt cctcttggta taaggcatcc catctccttt ctgtacccga  15180
ggtaagatgt gcaagacacg ggaactcctt atacttggct gaaggaagcg gagccatcat  15240
gagtcttctt gaactgcatg taccacatga aactatctat tacaatacgc tcttttcaaa  15300
tgagatgaac cccccgcaac gacatttcgg gccgacccca actcagtttt tgaattcggt  15360
tgtttatagg aatctacagg cggaggtaac atgcaaggat ggatttgtcc aagagttccg  15420
tccattatgg agagaaaata cagaggaaag tgacctgacc tcagataaag cagtggggta  15480
tattacatct gcagtaccct acagatctgt atcattgctg cattgtgaca ttgaaattcc  15540
tccagggtcc aatcaaagct tactagatca actagctatc aatttatctc tgattgccat  15600
gcattctgta agggagggcg ggtagtaat catcaaagtg ttgtatgcaa tgggatacta  15660
ctttcatcta ctcatgaact tgtttgctcc gtgttccaca aaaggatata ttctctctaa  15720
tggttatgca tgtcgagggg atatggagtg ttacctggta tttgtcatgg gttacctggg  15780
cgggcctaca tttgtacatg aggtggtgag gatggcaaaa actctggtgc agcggcacgg  15840
tacgcttttg tctaaatcag atgagatcac actgaccagg ttattcacct cacagcggca  15900
gcgtgtgaca gacatcctat ccagtccttt accaagatta ataaagtact tgaggaagaa  15960
tattgacact gcgctgattg aagccggggg acagcccgtc cgtccattct gtgcggagag  16020
tctggtgagc acgctagcga acataactca gataacccag atcatcgcta gccacattga  16080
cacagttatc cggtctgtga tatatatgga agctgagggt gatctcgctg acacagtatt  16140
tctatttacc ccttacaatc tctctactga cgggaaaaag aggacatcac ttaaacagtg  16200
cacgagacag atcctagagg ttacaatact aggtcttaga gtcgaaaatc tcaataaaat  16260
aggcgatata atcagcctag tgcttaaagg catgatctcc atggaggacc ttatcccact  16320
aaggacatac ttgaagcata gtacctgccc taaatatttg aaggctgtcc taggtattac  16380
caaactcaaa gaaatgttta cagacacttc tgtactgtac ttgactcgtg ctcaacaaaa  16440
attctacatg aaaactatag gcaatgcagt caaaggatat tacagtaact gtgactccta  16500
acgaaaatca catattaata ggctcctttt ttggccaatt gtattcttgt tgatttaatt  16560
atattatgtt agaaaaaagt tgaactctga ctccttagga ctcgaattcg aactcaaata  16620
aatgtcttta aaaaaggttg cgcacaatta ttcttgagtg tagtctcgtc attcaccaaa  16680
tctttgtttg gt                                                      16692
```

<210> SEQ ID NO 18
<211> LENGTH: 16692
<212> TYPE: RNA
<213> ORGANISM: Artificial Sequence
<220> FEATURE:
<223> OTHER INFORMATION: chimeric viral genome

<400> SEQUENCE: 18

```
ugguuugucu cuuaggcacu cagcgcuauu uuccgcuuuc ucguuaacuu cagugugccc     60
```

-continued

```
aucuuccaca cuuagagcuc acgcucgggc uucguguuug agcucuuucg gaagacgguu    120
guacagaagg cauaaacuac ucaugcuugu cgaggagcgc cgagucugag cgggguuacc    180
ucgaguaccu cccccucuuu uucccucaug gaauuuucau cugcagggcc auaagugaga    240
auugucacua cugggucuuc uaucuaccuc gaaacaccau aagacggagg ccuaacgaca    300
aucgcuucua cgguuguuug gugaguccgu uccacgagag uauagagaaa auacgagggu    360
gaguguccau uacuccuugg uacaacggga acgucccuuu gucuuacuuc gguguaaccg    420
gcacgaacuc uaacuaccga aacgguugcc gugcggggguc aaguuguuau ccucaccuca    480
cagacuucuc ucucgugucu cuaaacgcua cuaucguccu agagagggag cccguacguc    540
guugccuugg ggcaagcagu gucggccccg gcuucuacua cgugguucuc uguaguggcu    600
augggaccuc uccuaggaga gauagguccg aguucauacc cagugucauc guuuucggua    660
cugacgcaua cucugacguc uacucagccu uuguuccgcu uaguuauuca uauacgucgu    720
uccgucccag guuuucuuua uguaggagau ggggcauacg ucccucguguu agguugagug    780
cuagucuguc agagaacguc aggcguagaa aaaccaaucg cucgaguucu cuccggcguu    840
gugccgucca ccauggagau gaauaaauau ggaccauccc cugcaucuga guauguaguc    900
cuuauggccc gaaugacgua agaagaacug ugaguucaug ccuuaguugu gguucuguag    960
ucgggaacgu gaaucaucgg agaguccgcu guaggucuuc uacuucgucg aguacgcaaa   1020
cauagccuac uuuccucuau uacgcggcau guacuguaau gaaccacuau cacuggucua   1080
cucgaaacgc ggacggcuca uacguguuga aaugaggaaa cgguacccau accguaguca   1140
ggaucuauuu ccaugacccu uuaugguuaa acggucccug aaauacucgu guaguaagac   1200
cucugaaccu caucucaugc gaguccgagu cccuucaucg uaauugcucc uauaccgacg   1260
gcucgauuuc gauuggggguc gucguuccuc cccggaccgu cgacgacggg uugcccagag   1320
gcuccucugg ucgucguauc uguacggaug aguuguucag ccucaggagu gacccgaauc   1380
gcucccccccc aggguucgag auguuccgcc uagcuuaucu agcguucccg uuggucuucg   1440
gccccuaccc cucuggguua aggaccuaga cuacucucgc caucguuuau cguacucccu   1500
ccgcgguuug agacguguccc cgugaggggu uagccccgga gggggguugag gacccgguag   1560
gguucuauug cuguggcuga cccccauaac uaccuguuuu gggucggacg aagguguuuu   1620
uguaggguua cgggaguggg caucagcugg ggagcuaaac gccgagauau acuggugugg   1680
gaguuuguuu guagggggag aaaggaggga gggggacgac auguugaggc gugcgggauc   1740
uauggugucc guguuacgcc gagugauugu uaguuuuguc ucggcucccu uaaucuuuuu   1800
ucaugcccau cuucucccua uaagucucua gucccguuca gagggcucag agacgagaga   1860
ggagauggac uaucuggucc uguuuguacc gguggaaaug ucuacgucuc uagcugcucg   1920
auaaacucug uucaccuuga caguaacugu uguauuaaug ucgggucccca uuuggucguc   1980
ucugacaacc uuccucacgu uaggguguuc cguucugguu ccacgacucg cgucguaccc   2040
ucuucguacc cucguagguc gguggccggu caguuccguu ggggcuagcu guccugucua   2100
gacuguuugu ugguaggugu gggcccguuu gcuggggcgu acugucgggc ggccggugua   2160
ggcggcuggu cggggggugg guccggugucc ugcuucggca gcugugugucc gaguccuggc   2220
cucguucguu gagagacgac aacuacgaac uguucgaguc guuauuuagc agguuacgau   2280
uuuucccggg uaccagcucg gggguucucc ccuuaguggu ugcaggcuga guugucgucc   2340
ccucaguugg gucagcgccu uugucagucc uuucuggcgu cuugguucag uuccggcggg   2400
```

gaccuuuggu cccgugucug cacuugugucguauaguacc uguuacccuc cucaguguug 2460
auagucgacc acguugggga guacgagagg cuaguuccgu cucgguucug uuaugggaac 2520
auagacgccu aguacagguc gguggacauc ugaaacacgu ucgcuacuac agauacuacc 2580
uccgcuauag ugucucucau ucauuccagc ugauagucga ucuagaacag aacuuugucu 2640
guaggaggua gggauacuac gccaggcuuu agguugucga cuuuuguaga caacgucagu 2700
accuucgguu gaacccuuac uacuucuaag accuagggcc aacacgguug uaaaguagag 2760
acucacuaga ugcccgucaa cgggcuagag ugggccaaaa ucaaaguccg ggaccucugg 2820
ggagagggau acacuguguu ccucccgcuuu accgugaauu auuugaaagc guuggucacg 2880
guguagguag acuuaacuaa uuugggcggu gacguacgcc cggacuauau ccucaccuuu 2940
uccugugaca ggcacguaac uaguacagug cggguuacgu gggcucaaga agucgguucg 3000
aggauucguu caaucuacgu cggcccagcu agcuccuuua guccuuuuag uucgcggaac 3060
gagauuuacc gauuaaugau gacggugugc aucgcccagg gacaggugag ccguagugug 3120
ccuuagacgu ggcucaaggg ggggcgucug gguuccaggu ugagagguuc gccguuagga 3180
gagagcgaag aagucggggu gacuuacuag cgcauuggca uuaauuagau cgauguaauu 3240
ccuaauucuu uuuuaugccc aucuuaaccu cacgggguua acacucaaau caacuaucaa 3300 caucggugguacguggcagg aguagagucu gccgugagcg caaugaugcg cuuuccucuc 3360
cacgaauugu uuguguaccu aacgccaccu uuugccacga cgaguccgcg ucgacauaag 3420
ugagaaaaga ccugaacaca guccuaauac gcccucguau agacgaaaca ugcguugcga 3480
uaccuggcgg uaaauaaaaa cuccuuacga aaaaccugau agcaugacga aagaaggaag 3540
cgaucggucu cguggcggcg gcagugcaug cugauguaaa auccggcagc gcgcgagcug 3600
cgcgauuggu auggccgcca accgggcaua uugucuaugg agugauccca uaguucuccg 3660
acgcugcaac agcucgaguu gggcuaaaga uugcaccugc uguacuauag ccgccgguuu 3720
cuuuuucucu uccccccggg aaagcuccgg aggcagcaga ccaagaugca cuaauucccg 3780
cugcugccgc uccuguucau gacagguuag auaucuuuuc ucaugucccu uacaccgcug 3840
cauguugacg auagacuuac gcggcaaguu agacgugucu acacccguca ccugauacaa 3900
ggaucguggg aacauagcgc uuuaccgcgc ccugacugau auaagagggg gugacgacgc 3960
gagagaccgg uuaugaacga cugggacuuu uagcccucua aacgcguuug ucgagagcau 4020
ugagaucuuc aauugcuagc gacaaauuuc uagcccagcg ucgaauugaa aaauggcagc 4080
uuuacgaccu guugucuugu cauagucuga ccuaaaguuc cgcuugugga aauaggcuag 4140
cgucuguggu uaugugcugu gcgccugcug cauauagccc cuaugcuucu auaagacguc 4200
gcgaccuuau uaaacgacuc cuuuuucuua ggaucgcgcg gucugggagc aggucuaucg 4260
cagggcguuc uuuaagggcg acauugguuc uuucgccuuc ccgcgugggg ccugcgucuu 4320
ucgucgcuuu ucuuccgggg aggucuucug agccuccugc uguacguccg ucuccgaaga 4380
ccucuuuuag gacggcggga ggggcuucug cugcuucagg ggcuccugug gcucgugcua 4440
cuagguuuga gccuaggacu gauaauguua cuauacgggc ggcacuaggg ccaccuccuc 4500
ugaugauuuu caagauuacg gcagagguac ggguauaagc gccgcaagca ucggacgcgc 4560
cagcgcgagc accccgauga ccaaaccucg uagcauuuua cgcgcgcauc gauucgacac 4620
acauugaugg cacaugauuc ggggugagug ggucuaguag uacuguguuu uuugauuagc 4680
aauggagaga gcgaaggagu cggggugacu uacuagcgca uuggcauuaa uuagaucgau 4740
guaauuccua auucuuuuuu augcccaucu uaaccucacg ggguuaacac gguucuaccu 4800

-continued gaguagaucc uguuaacccg acaugaaacu aagacgggua agaagaucgu uggacaaucg 4860
uaaaggcuag caggauguuc ugugucccucu acccuucuuc guuuagcggg gcguuauauc 4920
cuaggucgcg gaacugaaca ccugacuauc auuccuccug agucauaagu aguggguggau 4980 accuaaguag aaaguucaac ccuuacuucu ucggugacag ccguacuagc uacuauuugg 5040
guucgcgcuc aaugaaaggc gacgcuacga gacggauccu ucgcaggguu uauggccucu 5100
ggaauaacuc gaccguuccc ggacagagug auacuaucag uguacguucu ucucacguug 5160
auuacgacuc ucuuaccaaa agagucauca cguccguggg guucacgacg uuucgacauc 5220
ccaacaccgu uuguuuauga guagucacuu acgucaguuc gugcacuuuc gcggucucuu 5280
cuaagggccc ucaccuuggg aucuuauguu ccacuugaaa cagaggaacu gacaccaugg 5340
cuucuuccua cagauguucu agggacgacg ucauaacuuc caaagaccga gcucagacau 5400
guuagaacgc gaguuacagu gauaauuaca ccuccaucug ggcuccucag gaaaccaauu 5460
uagagacaga uucagacugu cgccuaugau acgauuggag aagaacguau aaccugaaua 5520
cugguggcau cuauccuucc ccuucuuuca cuguaaacug uucgaccuuu ucuuuuauuc 5580
cucggaacua gauagacagc ccgagucacu acacgagccc ggaaggcaca accauuuucg 5640
uucuccacgu gccugauucg aaaaccgugg aaagaagaga ucgucacccu gucggacgau 5700
aggguaucgu uuacgaagag gaguccaccg guucuaugag accucaguuu ggcgcacgga 5760 cgcccucgcaa uuuuaguaau agguucgucc augggguugcg cgacagcguc acuggcggcu 5820
ggugcuccaa uggagaugau ucgaccucuu ccccgugugg gaacgguuua uguuaggaaa 5880
auucuuuauu cgacgcagag acucuaacgc gaggcgggug agugggucua guaguacugu 5940
guuuuuugau uagacagaac uaauaaaugu caaucaauug gacagauagu ucaaucuuuu 6000
uugugcccau cuucuaagac cuagggccaa ccgcgggagg uccacguucu acccgagguc 6060
uggaagaugg uucuugggguc guggauacua cgacugauag gcccaacgcg accaugacuc 6120
aacguagaca ggccguuuga gguaacuacc guccggagaa cgucgacguc cuuaacacca 6180
auguccucug uuucggcagu uguauaugug gaguagggguc uguccuaguu aguaucaauu 6240
cgaggagggc uuagacgggu uccuauuccu ccguacacgc uuucgggggga accuacguau 6300 guuguccugu aacuggugaa acgagugggg ggaaccacug agauaggcau ccuauguucu 6360
cagacacuga uguagaccuc cccccucugu ccccgcggaa uauccgcggu aauaaccgcc 6420
acaccgagaa ccccaacguu gacggcgugu uuauugucgc cggcgucgag acuauguucg 6480
guuuguuuua cgacgguugu aggaggcuga auuucucucg uaacggcguu gguuacuccg 6540
acacguacuc cagugacugc cuaauagcgu ugaucgucac cgucaacccu ucuacgucgu 6600
caaacaauua cugguugaau uauuuugucg aguccuuaau cugacguagu uuuaacgugu 6660
cguucaacca caucucgagu uggacaugga uuggcuuaac ugaugucaua agccuggugu 6720
uuagugaagu ggacgaaauu uguucgacug auaaguccgu gaaauguuag aucgaccacc 6780
uuuauaccua augaauaacu gauucaaucc acaucccuug uuaguugagu cgaguaauua 6840
gccaucgccg aauuaguggc cauugggaua agauaugcug agugucugag uugagaaccc 6900
auaugcccau ugagauggaa gucagcccuu ggauuuauua uacgcacggu ggaugaaccu 6960
uuggaauagg cauucguguu ggucccccuaa acggagccgu gaacaggggu uucaccacug 7020
uguccagcca agacacuauc uucuugaacu guggaguaug acauaucuuu gacugaaucu 7080
aaauauaaca uguucuuauc auugcaaggg auacagggga ccauaaauaa ggacgaacuc 7140

-continued gccguuaugc agccggacau acaugaguuu cuggcuuccg cgugaaugau gugguaugua 7200
cugauaguuu ccaagucagu agcgguugac guucuacugu uguacaucua cacauuuggg 7260
gggcccauag uauagcguuu ugauaccucu ucggcacaga gauuaucuau uuguuaguac 7320
guuacaaaau aggaauccgc ccuauugaaa uuccgaguca ccccuuaagc uacauugaau 7380
agucuucuua uagaguuaug uucuaagagu ucauuauuau uguccguuag aacuauagag 7440
uugacucgaa cccuuacagu uguugagcua gucauuacga aacuuauuca aucuccuuuc 7500
guugucuuuu gaucuguuuc aguuacaguu ugacugaucg uguagacgag aguaaaugau 7560
auagcaaaac ugauaguaua gagaacaaaa accauaugaa ucggacuaag aucguacgau 7620
ggauuacaug uucguuuucc gcguuguuuu cuggaauaau accgaacccu uauuaugaga 7680
ucuagucuac ucucggugau guuuuuacac uugugucuac ucuugcuuc caaagggauu 7740
aucauuaaac acacuuucaa gaccaucaga cagucaaguc ucucaauucu uuuuugaugg 7800
ccaacaucua cugguuuccu gcuauaugcc caucuugcca uucucuccgg cggggaguua 7860
acgcucgguc cgaaguguug gaggcaagau ggcgaagugg cuguugucag gaguuaguac 7920
cuggcgcggc aaucgguuca acgcaaucuc uuacuacuuu cucuccguuu uuuauguacc 7980
gcgaacuaua aggccuaacg uuagaauaag aauugucauc acuggaaccg auauagacau 8040
cggagggaaa auauaucgua cccccgaucg uguggaucgc uagaacaucc guauggcuga 8100
ucccuuaaggu cccgucuucu uuucuaaugu agaugugaac caagguuagu ucuacaucau 8160
cuauccuaua uauucguuca ccgggaacuc agaggcaacc guaacaauuu uugacucugg 8220
uguuaauacu ugcguuauug uagagagaga auagucuaau uaccucgacg uuuguuguca 8280
cccaccccccc gugaauaggu acugggucua auauaucccc ccuauccguu ucuugaguaa 8340
caucuacuac gaucacuaca guguaguaag auagggagac guaaaguucu uguagacuua 8400
aaauagggcc gcggaugaug uccuagucca acgugagcuu augggaguaa acuguacuca 8460
cgaugggguaa ugacgaugug gguauuacau uauaacagac cuacgucucu agugagugua 8520
aguauaguca uaaaucguga accacacgag gccuguagac guugucccuc ccauaagaaa 8580
agaugagacg caagguaguu ggaccugcug uggguuuuag ccuucagaac gucacacuca 8640
cguugagggg acccaacacu auacgacacg agcuuucagu gccucugucu ccuucuucua 8700
auauugaguc gacagggaug cgccuaccau guacccucca aucccaagcu gccggucaug 8760
gugcuuuucc uggaucuaca guguuguaau aagccccuga cccaccgguu gaugggguccu 8820
cauccccccac cuagaaaaua acugucggcg cauaccaaga gucagaugcc ucccaauuuu 8880
ggguuaagug ggucacugug acauguccuu cccuuuauac acuauauguu cgcuauguua 8940
cuguguacgg gucuacucgu ucugaugguc uaagcuuacc gguccagaag cauauucgga 9000
ccugccaaac cacccuuugc guaugucguc cgauagaaua gauaguucca caguuguagg 9060
aauccgcuuc ugggccauga cugacauggc ggguuguguc agugugagua cccccggcuu 9120
ccgucuuaag agugucaucc cuguagagua aagaacauag uugcucccag uaguaugaag 9180
agagggcgca auaaauaugg auacugucag ucguuguuuu gucggugaga aguaucagga 9240
auauguaagu uacggaagug agccggucca ucauagggaa cgguccgaag ucguucuacg 9300
ggguugggca cacaaugacc ucagauaugu cuaggugaag gggauuagaa gauaucuuug 9360
guguggaacg cuccccauaa gcccuguuac gaacuaccac auguucguuc ugaauuggga 9420
cgcagacguc auaagcuauc guguagggcg ucagcguaau gagcucacuc aaguucguca 9480
ugguuucguc guauguguug uaguugaaca aaauuucacc aguucugauu auucuggaua 9540

-continued acagagucgu aacgacuuua uagauuauga gagaagccuc uuaagucuua gcagggcaau 9600
gaucaacucu aggaguuucu acugccccaa ucucuucggu ccagaccgau caacucaguu 9660
aauauuuccu caaccuuucu accguaacau aguggauaga agacgcugua guucuuaguu 9720
uggcuuacgg ccgcgcacga gcuuaaggua caacggucaa cugguguuag ucggucacga 9780
guacgcuagu cuaauucgga acaguuauca gagaacuaau ucuuuuuuac auucaccguu 9840
acucuauguu ccguuuuguc gaguaccauu uauuaugccc aucuuguacc gcucgaggcc 9900
aggacuuucc cgucucguag ucuaauagga uggucucagu guggacagaa gugguaacca 9960
guucguguuu gaugagauaa ugaccuuuaa uugacccgau ggcgaaggac uacuuacacu 10020
gaagcuggug gaguaagagu cggcuguuac cuuuuuuuau gaacuuagcc ggagaggacu 10080
augacucucu uacuaucuug agccuucccg ucaugugguu ugagaauugg uguuaagguc 10140
uuauuggccu cacgaggugg gguccacaaa ucuucuugac cgauuauaac uccagggucu 10200
aaguugguug uuuaaagccu ucuaacucuu cuucuagguu uaaguguugu gcucuauacc 10260
ucuugacaag uguuccgaca caugcguaua ucucuucuuu gacgacccca guagaaccag 10320
auuguuacag ggggccaguc uccucaaguc gucguaagca ugccuaggcc guaagaccaa 10380
agugaguuuu accaggugu c gguucaaacg uaccgaggua uauuuugucu aggucuccgu 10440
agacuaccac cgucgauccu guuccagacg ccgguuguuu aaccacuacg auuggguauu 10500
ccauccgguu cagaaacagu gaggacuuga acagcaacac ugcguaugcu uacucuuguu 10560
caaguguaca gaaugggucc uugaacauaa cuacauacgu cuauacuacc ucccgucucu 10620
auaccaguug uauuauaguu ggugccgcca cguagagucu ucgaauaguc ucuuuuaacu 10680
acuguaaaac gccaauuauc ugcgagaccg uuuucugaac ccauuaguuc agaugcuaca 10740
acauagugau uaccucccua aacguaugcc ucgacagguc gaugagcucg gcaguccaug 10800
uaaacguccu cuaaagaagc guaaguugga cguccucgaa uuucuguaag auuaaccgga 10860
ggagggguua cuauaucguc uuaggcacug aguacguuag cgaugacaua agagaccaaa 10920
ucuugucuua guucgucgac ucuacaacac agacaacgca gacaccccag ugggugacga 10980
acucagggca uaacgucguu uccgucaguc cucgguuuac acgcguggcu uuuaccaucu 11040
gaaacuauac uaggaagucc augacagaaa gaaguucccu uguuaguagu ugcccauguc 11100
uuucuucuua cguccacaca ccggcgcuca guuucaccua uguuauauac ccuuccagua 11160
acccguugau guacgucuaa gucgucucua aagugugcua uaguacaacu cucucauauu 11220
cucaaauaga cgugaacuua aacucgguac auaucuuaua cugggacagu gguuggacuc 11280
guacaaggau uuucuguucc guuagcgugu gggguugcua uuaaccgaac ggagcaaauc 11340
cgccuuggaa gagaggcuuc uggucuucuu uguacauuuu cuucguugaa gcugauuagc 11400
ggagaacuau cucaaaaauc ucaguuuacu aaaacuaggu auauuucucu accuuauaga 11460
cugcugggaa cucauggaau cucuacuguu acaccgucau aguaugagcg aguuccucuu 11520
ccuucacuuu caauuaccug ccuagaagcg auucgacugu uucuucaauu ccuugacagu 11580
ccacuaccgc cuucccuagg aucggcuagu cuaacgugga aagaaagucc cuuuaccuca 11640
guaaguccua ucguauagga acugguucuc auacgaucgc uacucaguug acagaaaauu 11700
gucguuauuc uuugcauagu gacugacauu ucuuucucau agaaguuugg cguuaguacu 11760
aggcuuuucg uucuuggcag ccucucaacg uuggaaguau uguugacugg acguuuucau 11820
gacagaauua accucuauag ucugcuaguu uaacaagcga guacgguagu uagucaacua 11880

-continued

```
cccggaugga guaaagaagc ucaccuaagu ggauucugac uaccugugau gcuacaagca  11940
uccucuggga aaguuaggag guucacuggg augacugaca cuggagaguu cucagggauu  12000
acuacuguau auauaacagu cacggucucc cccauagcuu ccuaauacgg ucuucgauac  12060
cuguuacuag aguuaacgac guuagguuga acgacgucga ucuagcguaa cagcacaacg  12120
gacauaccau gucccacuau uaguucauua ucgucauugc ucucuccauu cuagucuacu  12180
gagaggccuc uaccacaacu gugucaacgu aguucgguca cuauuaaaga aguuccuuaa  12240
uuagguacag uuaguaaacu aaccgguauu aaacuuccua gcacuuuggu aguccagucu  12300
guguaagaag uauaugucgu uugcuuagaa guuucuaccu cguuaggagu caguucagga  12360
guuuuuaagu agauuuaauc acgaucacag uccacuagag ucacuuuugu gacauuacag  12420
gacacgguug uaacggagau gacaucgugc cgauacgcuc uugcccgaag gguuucugaa  12480
gacaaugaua aauuugauau auuacucaac acacgucugu augaaacuga gacucaagag  12540
guagugguug uuaagcgugg ggcuagaauu agucagcacc uaacuccugu agagaaaaca  12600
cgugaguaua caagacugag gacggguuaa ucccccugac ucauuggaag uuaugaguuc  12660
cgagauguga ucuuuauagc cacugggccc cugaugacga aaacgucucu aguucgcuga  12720
ucuucgucac ccuaaugacu caggauugua auacugauua uagaauugau ccggcggacc  12780
cuuaccucua acccggucag acacguugcu ggguaugaga aaguuaaaac ucugacaacg  12840
uucggguuua uaacaagaau ucuuuguaug cguuucucag gauaaacuuu gaacaaguuu  12900
agggaauaac agaccucacg ugugucuccu auuacuccgu cuucucuucc guaaccgacu  12960
uaagaacgaa uuaguucucc acuaaguagg ggcgcaacgc guacgguagu accuccguuc  13020
gagacaucca uccucuuucg uuuaaguucc cgaacaacug uguuguuugu ggcauuaauu  13080
cuaacgcgaa ugauccuccg guaauccgua guucuccgac uacgccuauc aguuaauaag  13140
aucguacgua cguuacgaca aaucucugcu acaaaaaagg aggucaucua gguugguggg  13200
gaaucagaga agauuauaca caagagacug ugaccgucug auacgugccu uaucuucgac  13260
caguggaaac ugcccuccgu ccuuuuauga cccacauaga uuaggacuau gcuaucuuga  13320
gcaucuccca cucuaagaau cacauucgcc ucccacaugu ucuacacugu cgccucuacu  13380
uguuaaauga accaagguag aagguucguu auaucuuaac uggcuacugu ggucguucuu  13440
aggaggcuac ucccauggua uagagcccag uuucuguguc cucuccucuc gacggaguga  13500
acguuuuuau cgaguauaca gcgguguaca uuuccgacgg gauucccgua guaggcacaa  13560
cuagacccga auaccccuau uacuucauuu aaccugacga cgagaaugcu aacguuuuag  13620
agccacguua cauuugaauc ucauagaagc caaugacagg ggaaaugggu gccgacccuu  13680
agaaguugua ucugaucuac uaccauauug agucuacugu aagugggac guagagagau  13740
gucccacagu ggaauguaag uguauagguu acuaagaguu uccgacaagu gacuucuucc  13800
ucaguuucuc cccuuacacc aaaugguugu cuaguacgag aacccaaaua gagauuagcu  13860
uagcuagaaa gguuacuguu guugguccug uauacuacuc uagugugacg uggauguauc  13920
auuuaaauca acgacauagu cucuucgugg acaacgccaa ggaaagcucg augaacccca  13980
ccauggccuu gacuccuguc acuggaguuu auucaaauac auacuaggau cgggacauag  14040
ccucccucug aaacgcucug aacugaaucg auagaaguuc ucaauacucg aauuagaccu  14100
caguauaggg ugcuaucucg auuacuugua agaaaguuau aggucgcccu ucaacuaacc  14160
ggucagacac caaagaauac uacuucuaug gagguauuuc uuacuacggu auuaucacau  14220
acuguuaugg gcuuuaaccu agucacuucg agucuuaagu cuacaccagg cggauaaacu  14280
```

uauacgucgu gaacuucacg aggagcugac aagaaugguu gagauaaugg acucucauuc 14340
uccggaucug uuauaacaga auauauaccc acuaaauaug uucuuauacg guccuuaaga 14400
ugaaagguug uaacgucgau guuauagagu aggacaguaa guaaguucca auguacguca 14460
cccggaccag uugguacugc cuagugugu ugaacgucua ugccuaaaau agcuuuacag 14520
acguuuugac aaucauagaa cgugggcugc acacuagagg ccgaauauaa guccuuuauu 14580
cauacuagac gacaagggua gacagaaucu acuauuggac uuacucuucu acgaagucga 14640
cuauagggcc aauacgacag acaugugcca ugagaaacga uguuguucuc uuuagggcuu 14700
uuauucuccg aauugacguc uucucuuuac aaguuaugag ugacucauaa augacagccu 14760
acgacacuuu gguaaugaau cggggcuagu ucacucgaga uaguacagag gauuguauua 14820
auguaagggu cgauuagaca ugauguacag agccuucucg gaguuaaacu agucccuuuc 14880
ccuccugucc cuaugauagg accgcaacaa caaggggguu cucgguaaua aucucaaggg 14940
aagacacguu cuauaaccac gagcucacuu ucuagguaag ugggcuguug gacgccguaa 15000
aaacguucuc aaucuaaacu cacgaggucg uuccauacug cguaagugug aaucagucua 15060
aguaggacuu gaguguagag guuuaggccu ccuucugaug aaucaugcua ugaacaaguc 15120
ucccuauccc ugacguagaa ggagaaccau auuccguagg guagaggaaa gacaugggcu 15180
ccauucuaca cguucugugc ccuugaggaa uaugaaccga cuuccuucgc cucgguagua 15240
cucagaagaa cuugacguac augguguacu uugauagaua auguuaugcg agaaaaguuu 15300
acucuacuug gggggcguug cuguaaagcc cggcuggggu ugagucaaaa acuuaagcca 15360
acaaauaucc uuagaugucc gccuccauug uacguuccua ccuaaacagg uucucaaggc 15420
agguaauacc ucucuuuuau gucuccuuuc acuggacugg agucuauuuc gucaccccau 15480
auaauguaga cgucauggga ugucuagaca uaguaacgac guaacacugu aacuuuaagg 15540
agguccca gg uuaguuucga augaucuagu ugaucgauag uuaaauagag acuaacggua 15600
cguaagacau ucccucccgc cccaucauua guaguuucac aacauacguu acccuaugau 15660
gaaaguagau gaguacuuga acaaacgagg cacaaggugu uuuccuauau aagagagauu 15720
accaauacgu acagcucccc uauaccucac aauggaccau aaacaguacc caauggaccc 15780
gcccggaugu aaacauguac ucccaccacuc cuaccguuuu ugagaccacg ucgccgugcc 15840
augcgaaaac agauuuaguc uacucuagug ugacuggucc aauaagugga gugucgccgu 15900
cgcacacugu cuguaggaua ggucaggaaa ugguucuaau uauuucauga acuccuucuu 15960
auaacuguga cgcgacuaac uucggccccc ugucgggcag gcagguaaga cacgccucuc 16020
agaccacucg ugcgaucgcu uguauugagu cuauugggguc uaguagcgau cgguguaacu 16080
gugucaauag gccagacacu auauauaccu ucgacuccca cuagagcgac ugugucauaa 16140
agauaaaugg ggaauguuag agagaugacu gcccuuuuuc uccuguagug aauuugucac 16200
gugcucuguc uaggaucucc aauguuauga uccagaaucu cagcuuuuag aguuauuuua 16260
uccgcuauau uagucggauc acgaauuucc guacuagagg uaccuccugg aauagggguga 16320
uuccuguaug aacuucguau cauggacggg auuuauaaac uuccgacagg auccauaaug 16380
guuugaguuu cuuuacaaau gucugugaag acaugacaug aacugagcac gaguuguuuu 16440
uaagauguac uuuugauauc cguuacguca guuuccuaua augucauuga cacugaggau 16500
ugcuuuuagu guauaauuau ccgaggaaaa aaccgguuaa cauaagaaca acuaaauuaa 16560
uauaauacaa ucuuuuuuca acuugagacu gaggaauccu gagcuuaagc uugaguuuau 16620
uuacagaaau uuuuuccaac gcguguuaau aagaacucac aucagagcag uaagugguuu 16680
agaaacaaac ca 16692

<210> SEQ ID NO 19
<211> LENGTH: 22
<212> TYPE: DNA
<213> ORGANISM: Infectious laryngotracheitis virus (ILTV)

<400> SEQUENCE: 19
ccttgcgttt gaatttttct gt 22

<210> SEQ ID NO 20
<211> LENGTH: 20
<212> TYPE: DNA
<213> ORGANISM: Infectious laryngotracheitis virus (ILTV)

<400> SEQUENCE: 20
ttcgtgggtt agaggtctgt 20

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
cagctcggtg accccattct a 21

<210> SEQ ID NO 22
<211> LENGTH: 103
<212> TYPE: DNA
<213> ORGANISM: Infectious laryngotracheitis virus (ILTV)

<400> SEQUENCE: 22
ccttgcgttt gaatttttct gtgatccgcc acacgttttt cgagggcagc tcggtgaccc 60
cattctattg caatgcttca gcgacagacc tctaacccac gaa 103

<210> SEQ ID NO 23
<211> LENGTH: 22
<212> TYPE: DNA
<213> ORGANISM: chicken

<400> SEQUENCE: 23
gggaactgga gaacccaatt tt 22

<210> SEQ ID NO 24
<211> LENGTH: 20
<212> TYPE: DNA
<213> ORGANISM: chicken

<400> SEQUENCE: 24
cgtgccgctg tctctaccat 20

<210> SEQ ID NO 25
<211> LENGTH: 29
<212> TYPE: DNA
<213> ORGANISM: Artificial Sequence
<220> FEATURE:
<223> OTHER INFORMATION: Primer

<400> SEQUENCE: 25
cccttaactg agttccccag ctactgcag 29

-continued

```
<210> SEQ ID NO 26
<211> LENGTH: 76
<212> TYPE: DNA
<213> ORGANISM: chicken

<400> SEQUENCE: 26

gggaactgga gaacccaatt tttcccttaa ctgagttccc cagctactgc agaccaatgg      60

tagagacagc ggcacg                                                       76
```